United States Patent
Hemminki et al.

(10) Patent No.: US 11,485,791 B2
(45) Date of Patent: Nov. 1, 2022

(54) ONCOLYTIC ADENOVIRUSES CODING FOR BI-SPECIFIC ANTIBODIES

(71) Applicant: TILT Biotherapeutics Oy, Helsinki (FI)

(72) Inventors: Akseli Hemminki, Helsinki (FI); Suvi Parviainen, Helsinki (FI); Siri Tähtinen, Helsinki (FI); Ilkka Liikanen, Helsinki (FI); Mikko Siurala, Helsinki (FI)

(73) Assignee: TILT Biotherapeutics Oy, Helsinki (FI)

( * ) Notice: Subject to any disclaimer, the term of this patent is extended or adjusted under 35 U.S.C. 154(b) by 997 days.

(21) Appl. No.: 15/559,080

(22) PCT Filed: Mar. 17, 2016

(86) PCT No.: PCT/FI2016/050164
§ 371 (c)(1),
(2) Date: Sep. 18, 2017

(87) PCT Pub. No.: WO2016/146894
PCT Pub. Date: Sep. 22, 2016

(65) Prior Publication Data
US 2018/0072809 A1   Mar. 15, 2018

(30) Foreign Application Priority Data
Mar. 17, 2015 (FI) ..................... 20155182

(51) Int. Cl.
| | |
|---|---|
| C12N 15/86 | (2006.01) |
| C07K 16/30 | (2006.01) |
| C07K 16/28 | (2006.01) |
| A61K 39/00 | (2006.01) |

(52) U.S. Cl.
CPC .............. *C07K 16/30* (2013.01); *C07K 16/28* (2013.01); *C07K 16/2809* (2013.01); *C07K 16/2821* (2013.01); *C07K 16/3092* (2013.01); *C12N 15/86* (2013.01); *A61K 2039/585* (2013.01); *C07K 2317/31* (2013.01); *C07K 2317/622* (2013.01); *C12N 2710/00044* (2013.01); *C12N 2710/00045* (2013.01); *C12N 2710/10033* (2013.01); *C12N 2710/10332* (2013.01)

(58) Field of Classification Search
CPC .............. C07K 16/2809; C07K 16/28; C07K 2317/31; C07K 2317/622; C07K 16/2821; C07K 16/3092; C07K 16/30; A61P 35/00; A61P 35/02; A61P 43/00; C12N 2710/10033; C12N 2710/00044; C12N 2710/10332; C12N 2710/00045; C12N 15/86; A61K 2039/585
See application file for complete search history.

(56) References Cited

U.S. PATENT DOCUMENTS

2013/0243731 A1   9/2013   Dias et al.

FOREIGN PATENT DOCUMENTS

| CN | 1381562 A | 11/2002 | |
| CN | 101437538 A | 5/2009 | |
| CN | 103221423 A | 7/2013 | |
| CN | 103221544 A | 7/2013 | |
| WO | WO2009106096 A1 | 9/2009 | |
| WO | WO-2012038606 A1 * | 3/2012 | ............. A61K 45/06 |
| WO | WO-2012038607 A1 * | 3/2012 | ......... A61K 48/0058 |
| WO | WO2013114367 A9 | 8/2013 | |
| WO | WO-2014138314 A1 * | 9/2014 | ..... A61K 39/001106 |
| WO | WO2014138314 A1 | 9/2014 | |
| WO | WO-2014170389 A1 * | 10/2014 | ............. A61P 43/00 |
| WO | WO2014170389 A1 | 10/2014 | |
| WO | WO2016146894 A1 | 9/2016 | |

OTHER PUBLICATIONS

Yu et al Molecular Therapy,, 1-10 (Year: 2013).*
Koski et al Molecular Therapy, 218, 10, 1874-1884 (Year: 2010).*
Carlos et al Human Gene Therapy, 26, A13-A14 (Year: 2015).*
Lichtenstein et al Journal of Virology, 12297-12307 (Year: 2004).*
Blair et al: Restricted replication of human adenovirus type 5 in mouse cell lines. Virus Res., Dec. 1989, vol. 14, No. 4, pp. 339-346.
Ekkens et al: Th1 and Th2 Cells Help CD8 T-Cell Responses. Infection and Immunity, May 2007, vol. 75, No. 5, pp. 2291-2296.
Fajardo et al: Bi-specific T-cell engager-armed oncolytic adenoviruses as a strategy to improve antitumor efficacy. Human Gene Therapy, Sep. 2015, vol. 26, No. 9, pp. A13-A14.
Feng et al: T-cell engager-armed oncolytic vaccinia virus significantly enhances antitumor therapy. Molecular Therapy Jan. 2014, vol. 22, No. 1, pp. 102-111.
Hemminki et al: Armed oncolytic adenovirus can overcome critical obstacles in adoptive T-cell therapy of solid tumors. Database Biosis, Nov. 2014.
Hemminki et al: Immunological data from cancer patients treated with Ad5/3-E2F-Delta 24-GMCSF suggests utility for tumor immunotherapy. Oncotarget, Feb. 28, 2015, vol. 6, No. 6, pp. 4467-4481.
Kanerva et al: Antiviral and antitumor T-cell immunity in patients treated with GM-CSF-coding oncolytic adenivirus. Clinical Cancer Research, May 15, 2013, vol. 19, No. 10, pp. 2734-2744.
Kanerva et al: Noninvasive dual modality in vivo monitoring of the persistence and potency of a tumor targeted conditionally replicating adenovirus. Gene Therapy, 2005, vol. 12, pp. 87-94.

(Continued)

*Primary Examiner* — Anoop K Singh
(74) *Attorney, Agent, or Firm* — Laine IP Oy; Mark W. Scott

(57) ABSTRACT

The present invention relates to the fields of life sciences and medicine. Specifically, the invention relates to cancer therapies of humans. More specifically, the present invention relates to an oncolytic adenoviral vector encoding a bispecific monoclonal antibody. Furthermore, the present invention relates to methods and uses utilizing the oncolytic adenoviral vectors, also together with adoptive cell therapies.

6 Claims, 11 Drawing Sheets
Specification includes a Sequence Listing.

(56) References Cited

OTHER PUBLICATIONS

Koski et al: Treatment of Cancer Patients With a Serotype 5/3 Chimeric Oncolytic Adenovirus Expressing GMCSF. The American Society of Gene & Cell Therapy, Oct. 2010, vol. 18, No. 10, pp. 1874-1884.

Kratky et al: Direct activation of antigen-presenting cells is required for CD8+ T-cell priming and tumor vaccination. PNAS, Oct. 18, 2011, vol. 108, No. 42, pp. 17414-17419.

Lugade et al: Radiation-Induced IFN-g Production within the Tumor Microenvironment Influences Antitumor Immunity The Journal of Immunology, 2008, vol. 180, pp. 3132-3139.

Park et al: Characteristics of Cell Lines Established from Human Gastric Carcinoma. Cancer Research, May 1, 1990, vol. 50, pp. 2773-2780.

Parviainen et al: CD40 ligand and tdTomato-armed vaccinia virus for induction of antitumor immune response and tumor imaging. Gene Therapy, Dec. 5, 2013, pp. 1-10.

Propper et al: Low-Dose IFN-Induces Tumor MHC Expression in Metastatic Malignant Melanoma. Clinical Cancer Research. Jan. 2003, vol. 9, pp. 84-92.

Schroder et al: Interferon-?: an overview of signals, mechanisms and functions. Journal of Leukocyte Biology, Feb. 2004, vol. 75, pp. 163-189.

Street et al: Interferon-? Enhances Susceptibility of Cervical Cancer Cells to Lysis by Tumor-Specific Cytotoxic T Cells. Gynecologic Oncology, May 1997, vol. 65, No. 2, pp. 265-272.

Taipale et al: Chronic Activation of Innate Immunity Correlates With Poor Prognosis in Cancer Patients Treated With Oncolytic Adenovirus. Molecular Therapy, Jan. 2016, vol. 24, No. 1, pp. 175-183.

Tähtinen et al: Adenovirus Improves the Efficacy of Adoptive T-cell Therapy by Recruiting Immune Cells to and Promoting Their Activity at the Tumor. Cancer Immunology Research, Aug. 2015, vol. 3, No. 8, pp. 915-925.

Tähtinen et al: Favorable Alteration of Tumor Microenvironment by Immunomodulatory Cytokines for Efficient T-Cell Therapy in Solid Tumors. PLOS ONE, Jun. 24, 2015, pp. 1-20.

Yu et al: T-cell Engager-armed Oncolytic Vaccinia Virus Significantly Enhances Antitumor Therapy. Molecular Therapy, Dec. 10, 2013, pp. 1-10.

Teigler: Differential Innate Immune Stimulation Elicited by Adenovirus and Poxvirus Vaccine Vectors. Doctoral dissertation, Harvard University, 2014.

\* cited by examiner

SEQUENCE LISTING

<160> NUMBER OF SEQ ID NOS: 9

<210> SEQ ID NO 1
<211> LENGTH: 358
<212> TYPE: DNA
<213> ORGANISM: adenovirus

<400> SEQUENCE: 1

```
catcatcaat aatataccct attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgtttttg   180
gtgtgcgccg gtgtacacag gaagtgacaa ttttcgcgcg gttttaggcg gatgttgtag   240
taaatttggg cgtaaccgag taagatttgg ccattttcgc gggaaaactg aataagagga   300
agtgaaatct gaataatttt gtgttactca tagcgcgtaa tactggtacc gcggccgc     358
```

<210> SEQ ID NO 2
<211> LENGTH: 680
<212> TYPE: DNA
<213> ORGANISM: adenovirus

<400> SEQUENCE: 2

```
tggtaccatc cggacaaagc ctgcgcgcgc cccgccccgc cattggccgt accgccccgc    60
gccgccgccc catcccgccc ctcgccgccg ggtccggcgc gttaaagcca ataggaaccg   120
ccgccgttgt tcccgtcacg gccggggcag ccaattgtgg cggcgctcgg cggctcgtgg   180
ctctttcgcg gcaaaaagga tttggcgcgt aaaagtggcc gggactttgc aggcagcggc   240
ggccgggggc ggagcgggat cgagccctcg ccctcgagct agaagcttgt tttctcctcc   300
gagccgctcc gacaccggga ctgaaaatga gacatattat ctgccacgga ggtgttatta   360
ccgaagaaat ggccgccagt cttttggacc agctgatcga agaggtactg gctgataatc   420
ttccacctcc tagccatttt gaaccaccta cccttcacga actgtatgat ttagacgtga   480
cggcccccga agatcccaac gaggaggcgg tttcgcagat ttttcccgac tctgtaatgt   540
tggcggtgca ggaagggatt gacttactca ctttttccgcc ggcgcccggt tctccggagc   600
cgcctcacct ttcccggcag cccgagcagc cggagcagag agccttgggt ccggtttcta   660
tgccaaacct tgtaccggag                                                680
```

<210> SEQ ID NO 3
<211> LENGTH: 27458
<212> TYPE: DNA
<213> ORGANISM: adenovirus

<400> SEQUENCE: 3

```
gtgatcgatc cacccagtga cgacgaggat gaagagggtg aggagtttgt gttagattat    60
gtggagcacc ccgggcacgg ttgcaggtct tgtcattatc accggaggaa tacgggggac   120
ccagatatta tgtgttcgct ttgctatatg aggacctgtg gcatgtttgt ctacagtaag   180
```

```
tgaaaattat gggcagtggg tgatagagtg gtgggtttgg tgtggtaatt ttttttttaa        240
tttttacagt tttgtggttt aaagaatttt gtattgtgat tttttttaaaa ggtcctgtgt       300 ctgaacctga gcctgagccc gagccagaac cggagcctgc aagacctacc cgccgtccta       360
aaatggcgcc tgctatcctg agacgcccga catcacctgt gtctagagaa tgcaatagta       420
gtacggatag ctgtgactcc ggtccttcta acacacctcc tgagatacac ccggtggtcc       480
cgctgtgccc cattaaacca gttgccgtga gagttggtgg gcgtcgccag gctgtggaat       540
gtatcgagga cttgcttaac gagcctgggc aacctttgga cttgagctgt aaacgcccca       600
ggccataagg tgtaaacctg tgattgcgtg tgtggttaac gcctttgttt gctgaatgag       660
ttgatgtaag tttaataaag ggtgagataa tgtttaactt gcatggcgtg ttaaatgggg       720
cggggcttaa agggtatata atgcgccgtg ggctaatctt ggttacatct gacctcatgg       780
aggcttggga gtgtttggaa gattttttctg ctgtgcgtaa cttgctggaa cagagctcta       840
acagtacctc ttggttttgg aggttttctgt ggggctcatc ccaggcaaag ttagtctgca       900
gaattaagga ggattacaag tgggaatttg aagagctttt gaaatcctgt ggtgagctgt       960
ttgattcttt gaatctgggt caccaggcgc ttttccaaga gaaggtcatc aagactttgg      1020
atttttccac accggggcgc gctgcggctg ctgttgcttt tttgagtttt ataaggata       1080 aatggagcga agaaacccat ctgagcgggg ggtacctgct ggattttctg gccatgcatc      1140
tgtggagagc ggttgtgaga cacaagaatc gcctgctact gttgtcttcc gtccgccgg       1200 cgataatacc gacggaggag cagcagcagc agcaggagga agccaggcgg cggcggcagg      1260
agcagagccc atggaacccg agagccggcc tggaccctcg ggaatgaatg ttgtacaggt      1320
ggctgaactg tatccagaac tgagacgcat tttgacaatt acagaggatg ggcaggggct      1380 aaaggggta aagagggagc gggggggcttg tgaggctaca gaggaggcta ggaatctagc      1440
ttttagctta atgaccagac accgtcctga gtgtattact tttcaacaga tcaaggataa      1500
ttgcgctaat gagcttgatc tgctggcgca gaagtattcc atagagcagc tgaccactta      1560
ctggctgcag ccaggggatg attttgagga ggctattagg gtatatgcaa aggtggcact      1620
taggccagat tgcaagtaca agatcagcaa acttgtaaat atcaggaatt gttgctacat      1680
ttctgggaac ggggccgagg tggagataga tacggaggat agggtggcct ttagatgtag      1740
catgataaat atgtggccgg gggtgcttgg catggacggg gtggttatta tgaatgtaag      1800
gtttactggc cccaattttta gcggtacggt tttcctggcc aataccaacc ttatcctaca      1860
cggtgtaagc ttctatgggt ttaacaatac ctgtgtggaa gcctggaccg atgtaagggt      1920
tcggggctgt gcctttttact gctgctggaa gggggtggtg tgtcgcccca aaagcagggc      1980
ttcaattaag aaatgcctct ttgaaaggtg taccttgggt atcctgtctg agggtaactc      2040
cagggtgcgc cacaatgtgg cctccgactg tggttgcttc atgctagtga aaagcgtggc      2100
tgtgattaag cataacatgg tatgtggcaa ctgcgaggac agggcctctc agatgctgac      2160
ctgctcggac ggcaactgtc acctgctgaa gaccattcac gtagccagcc actctcgcaa      2220
ggcctggcca gtgtttgagc ataacatact gacccgctgt ccttgcatt tgggtaacag      2280 gagggggtg ttcctacctt accaatgcaa tttgagtcac actaagatat tgcttgagcc      2340
cgagagcatg tccaaggtga acctgaacgg ggtgtttgac atgaccatga agatctggaa      2400
ggtgctgagg tacgatgaga cccgcaccag gtgcagaccc tgcgagtgtg gcggtaaaca      2460
tattaggaac cagcctgtga tgctggatgt gaccgaggag ctgaggcccg atcacttggt      2520
gctggcctgc acccgcgctg agtttggctc tagcgatgaa gatacagatt gaggtactga      2580
```

```
aatgtgtggg cgtggcttaa gggtgggaaa gaatatataa ggtgggggtc ttatgtagtt    2640
ttgtatctgt tttgcagcag ccgccgccgc catgagcacc aactcgtttg atggaagcat    2700
tgtgagctca tatttgacaa cgcgcatgcc cccatgggcc ggggtgcgtc agaatgtgat    2760
gggctccagc attgatggtc gccccgtcct gcccgcaaac tctactacct tgacctacga    2820
gaccgtgtct ggaacgccgt tggagactgc agcctccgcc gccgcttcag ccgctgcagc    2880
caccgcccgc gggattgtga ctgactttgc tttcctgagc ccgcttgcaa gcagtgcagc    2940
ttcccgttca tccgcccgcg atgacaagtt gacggctctt ttggcacaat tggattcttt    3000
gacccgggaa cttaatgtcg tttctcagca gctgttggat ctgcgccagc aggtttctgc    3060
cctgaaggct tcctcccctc ccaatgcggt ttaaaacata aataaaaaac cagactctgt    3120
ttggatttgg atcaagcaag tgtcttgctg tctttattta ggggttttgc gcgcgcggta    3180
ggcccgggac cagcggtctc ggtcgttgag ggtcctgtgt attttttcca ggacgtggta    3240
aaggtgactc tggatgttca gatacatggg cataagcccg tctctggggt ggaggtagca    3300
ccactgcaga gcttcatgct gcggggtggt gttgtagatg atccagtcgt agcaggagcg    3360
ctgggcgtgt tgcctaaaaa tgtctttcag tagcaagctg attgccaggg gcaggccctt    3420
ggtgtaagtg tttacaaagc ggttaagctg ggatgggtgc atacgtgggg atatgagatg    3480
catcttggac tgtattttta ggttggctat gttcccagcc atatccctcc ggggattcat    3540
gttgtgcaga accaccagca cagtgtatcc ggtgcacttg ggaaatttgt catgtagctt    3600
agaaggaaat gcgtggaaga acttggagac gcccttgtga cctccaagat tttccatgca    3660
ttcgtccata atgatggcaa tgggcccacg ggcggcggcc tgggcgaaga tatttctggg    3720
atcactaacg tcatagttgt gttccaggat gagatcgtca taggccattt ttacaaagcg    3780
cgggcggagg gtgccagact gcggtataat ggttccatcc ggcccagggg cgtagttacc    3840
ctcacagatt tgcatttccc acgctttgag ttcagatggg gggatcatgt ctacctgcgg    3900
ggcgatgaag aaaacggttt ccggggtagg ggagatcagc tgggaagaaa gcaggttcct    3960
gagcagctgc gacttaccgc agccggtggg cccgtaaatc acacctatta ccgggtgcaa    4020
ctggtagtta agagagctgc agctgccgtc atccctgagc aggggggcca cttcgttaag    4080
catgtccctg actcgcatgt tttccctgac caaatccgcc agaaggcgct cgccgcccag    4140
cgatagcagt tcttgcaagg aagcaaagtt tttcaacggt ttgagaccgt ccgccgtagg    4200
catgcttttg agcgtttgac caagcagttc caggcggtcc cacagctcgg tcacctgctc    4260
tacggcatct cgatccagca tatctcctcg tttcgcgggt tgggcgcgct tcgctgtac    4320 ggcagtagtc ggtgctcgtc cagacgggcc agggtcatgt ctttccacgg gcgcagggtc    4380
ctcgtcagcg tagtctgggt cacggtgaag gggtgcgctc cggctgcgc gctgccagg    4440 gtgcgcttga ggctggtcct gctggtgctg aagcgctgcc ggtcttcgcc ctgcgcgtcg    4500
gccaggtagc atttgaccat ggtgtcatag tccagcccct ccgcggcgtg gcccttggcg    4560
cgcagcttgc ccttggagga ggcgccgcac gaggggcagt gcagactttt gagggcgtag    4620
agcttgggcg cgagaaatac cgattccggg gagtaggcat ccgcgccgca ggccccgcag    4680
acggtctcgc attccacgag ccaggtgagc tctggccgtt cggggtcaaa aaccaggttt    4740
cccccatgct ttttgatgcg tttcttacct ctggtttcca tgagccggtg tccacgctcg    4800
gtgacgaaaa ggctgtccgt gtccccgtat acagacttga gaggcctgtc ctcgagcggt    4860
gttccgcggt cctcctcgta tagaaactcg gaccactctg agacaaaggc tcgcgtccag    4920
```

-continued

```
gccagcacga aggaggctaa gtgggagggg tagcggtcgt tgtccactag ggggtccact    4980
cgctccaggg tgtgaagaca catgtcgccc tcttcggcat caaggaaggt gattggtttg    5040
taggtgtagg ccacgtgacc gggtgttcct gaagggggc tataaaaggg ggtgggggcg     5100
cgttcgtcct cactctcttc cgcatcgctg tctgcgaggg ccagctgttg gggtgagtac    5160
tccctctgaa aagcgggcat gacttctgcg ctaagattgt cagtttccaa aaacgaggag    5220
gatttgatat tcacctggcc cgcggtgatg ccttt gaggg tggccgcatc catctggtca   5280
gaaaagacaa tcttttttgtt gtcaagcttg gtggcaaacg acccgtagag ggcgttggac   5340
agcaacttgg cgatggagcg cagggtttgg ttttttgtcgc gatcggcgcg ctccttggcc   5400
gcgatgttta gctgcacgta ttcgcgcgca acgcaccgcc attcgggaaa gacggtggtg    5460
cgctcgtcgg gcaccaggtg cacgcgccaa ccgcggttgt gcagggtgac aaggtcaacg    5520
ctggtggcta cctctccgcg taggcgctcg ttggtccagc agaggcggcc gcccttgcgc    5580
gagcagaatg gcggtagggg gtctagctgc gtctcgtccg gggggtctgc gtccacggta    5640
aagaccccgg gcagcaggcg cgcgtcgaag tagtctatct tgcatccttg caagtctagc    5700
gcctgctgcc atgcgcgggc ggcaagcgcg cgctcgtatg ggttgagtgg gggaccccat    5760
ggcatggggt gggtgagcgc ggaggcgtac atgccgcaaa tgtcgtaaac gtagaggggc    5820
tctctgagta ttccaagata tgtagggtag catcttccac cgcggatgct ggcgcgcacg    5880
taatcgtata gttcgtgcga gggagcgagg aggtcgggac cgaggttgct acgggcgggc    5940
tgctctgctc ggaagactat ctgcctgaag atggcatgtg agttggatga tatggttgga    6000
cgctggaaga cgttgaagct ggcgtctgtg agacctaccg cgtcacgcac gaaggaggcg    6060
taggagtcgc gcagcttgtt gaccagctcg gcggtgacct gcacgtctag ggcgcagtag    6120
tccagggttt ccttgatgat gtcatactta tcctgtccct tttttttcca cagctcgcgg    6180
ttgaggacaa actcttcgcg gtctttccag tactcttgga tcggaaaccc gtcggcctcc    6240
gaacggtaag agcctagcat gtagaactgg ttgacggcct ggtaggcgca gcatccctt     6300
tctacgggta gcgcgtatgc ctgcgcggcc ttccggagcg aggtgtgggt gagcgcaaag    6360
gtgtccctga ccatgacttt gaggtactgg tatttgaagt cagtgtcgtc gcatccgccc    6420
tgctcccaga gcaaaaagtc cgtgcgcttt ttggaacgcg gatttggcag ggcgaaggtg    6480
acatcgttga agagtatctt tcccgcgcga ggcataaagt tgcgtgtgat gcggaagggt    6540
cccggcacct cggaacggtt gttaattacc tgggcggcga gcacgatctc gtcaaagccg    6600
ttgatgttgt ggcccacaat gtaaagttcc aagaagcgcg ggatgccctt gatgaaggc     6660
aattttttaa gttcctcgta ggtgagctct tcaggggagc tgagcccgtg ctctgaaagg    6720
gcccagtctg caagatgagg gttggaagcg acgaatgagc tccacaggtc acgggccatt    6780
agcatttgca ggtggtcgcg aaaggtccta aactggcgac ctatggccat tttttctggg    6840
gtgatgcagt agaaggtaag cgggtcttgt tcccagcggt cccatccaag gttcgcggct    6900
aggtctcgcg cggcagtcac tagaggctca tctccgccga acttcatgac cagcatgaag    6960
ggcacgagct gcttcccaaa ggcccccatc caagtatagg tctctacatc gtaggtgaca    7020
aagagacgct cggtgcgagg atgcgagccg atcgggaaga actggatctc ccgccaccaa    7080
ttggaggagt ggctattgat gtggtgaaag tagaagtccc tgcgacgggc cgaacactcg    7140
tgctggcttt tgtaaaaacg tgcgcagtac tggcagcggt gcacgggctg tacatcctgc    7200
acgaggttga cctgacgacc gcgcacaagg aagcagagtg ggaatttgag cccctcgcct    7260
ggcgggtttg gctggtggtc ttctacttcg gctgcttgtc cttgaccgtc tggctgctcg    7320
```

```
aggggagtta cggtggatcg gaccaccacg ccgcgcgagc ccaaagtcca gatgtccgcg      7380
cgcggcggtc ggagcttgat gacaacatcg cgcagatggg agctgtccat ggtctggagc      7440
tcccgcggcg tcaggtcagg cgggagctcc tgcaggttta cctcgcatag acgggtcagg      7500
gcgcgggcta gatccagctg atacctaatt tccaggggct ggttggtggc ggcgtcgatg      7560
gcttgcaaga ggccgcatcc ccgcggcgcg actacggtac cgcgcggcgg cggtgggcc       7620 gcggggggtgt ccttggatga tgcatctaaa agcggtgacg cgggcgagcc cccgaggta      7680 gggggggctc cggacccgcc gggagagggg gcaggggcac gtcggcgccg cgcgcgggca      7740
ggagctggtc ctgcgcgcgt aggttgctgg cgaacgcgac gacgcggcgg ttgatctcct      7800
gaatctggcg cctctgcgtg aagacgacgg gcccggtgag cttgagcctg aaagagagtt      7860
cgacagaatc aatttcggtg tcgttgacgg cggcctggcg caaaatctcc tgcacgtctc      7920
ctgagttgtc ttgataggcg atctcggcca tgaactgctc gatctcttcc tcctggagat      7980
ctccgcgtcc ggctcgctcc acggtggcgg cgaggtcgtt ggaaatgcgg gccatgagct      8040
gcgagaaggc gttgaggcct ccctcgttcc agacgcggct gtagaccacg cccccttcgg      8100
catcgcgggc gcgcatgacc acctgcgcga gattgagctc cacgtgccgg gcgaagacgg      8160
cgtagtttcg caggcgctga aagaggtagt tgagggtggt ggcggtgtgt tctgccacga      8220
agaagtacat aacccagcgt cgcaacgtgg attcgttgat atcccccaag gcctcaaggc      8280
gctccatggc ctcgtagaag tccacggcga agttgaaaaa ctgggagttg cgcgccgaca      8340
cggttaactc ctcctccaga agacggatga gctcggcgac agtgtcgcgc acctcgcgct      8400
caaaggctac aggggcctct tcttcttctt caatctcctc ttccataagg gcctcccctt      8460
cttcttcttc tggcgcggt gggggagggg ggacacggcg gcgacgacgg cgcaccggga      8520
ggcggtcgac aaagcgctcg atcatctccc cgcggcgacg gcgcatggtc tcggtgacgg      8580
cgcggccgtt ctcgcggggg cgcagttgga agacgccgcc cgtcatgtcc cggttatggg      8640
ttggcggggg gctgccatgc ggcagggata cggcgctaac gatgcatctc aacaattgtt      8700
gtgtaggtac tccgccgccg agggacctga gcgagtccgc atcgaccgga tcggaaaacc      8760
tctcgagaaa ggcgtctaac cagtcacagt cgcaaggtag gctgagcacc gtggcgggcg      8820
gcagcgggcg gcggtcgggg ttgttttctgg cggaggtgct gctgatgatg taattaaagt      8880
aggcggtctt gagacggcgg atggtcgaca gaagcaccat gtccttgggt ccggcctgct      8940
gaatgcgcag gcggtcggcc atgccccagg cttcgttttg acatcggcgc aggtctttgt      9000
agtagtcttg catgagcctt tctaccggca cttcttcttc tccttcctct tgtcctgcat      9060
ctcttgcatc tatcgctgcg gcggcggcgg agtttggccg taggtggcgc cctcttcctc      9120
ccatgcgtgt gaccccgaag cccctcatcg gctgaagcag ggctaggtcg cgacaacgc      9180 gctcggctaa tatggcctgc tgcacctgcg tgagggtaga ctggaagtca tccatgtcca      9240
caaagcggtg gtatgcgccc gtgttgatgg tgtaagtgca gttggccata acggaccagt      9300
taacggtctg gtgacccggc tgcgagagct cggtgtacct gagacgcgag taagccctcg      9360
agtcaaatac gtagtcgttg caagtccgca ccaggtactg gtatcccacc aaaaagtgcg      9420
gcggcggctg gcggtagagg ggccagcgta gggtggccgg ggctccgggg gcgagatctt      9480
ccaacataag gcgatgatat ccgtagatgt acctggacat ccaggtgatg ccggcggcgg      9540
tggtggaggc gcgcggaaag tcgcggacgc ggttccagat gttgcgcagc ggcaaaaagt      9600
gctccatggt cgggacgctc tggccggtca ggcgcgcgca atcgttgacg ctctagaccg      9660
```

```
tgcaaaagga gagcctgtaa gcgggcactc ttccgtggtc tggtggataa attcgcaagg    9720
gtatcatggc ggacgaccgg ggttcgagcc ccgtatccgg ccgtccgccg tgatccatgc    9780
ggttaccgcc cgcgtgtcga acccaggtgt gcgacgtcag acaacggggg agtgctcctt    9840
ttggcttcct tccaggcgcg gcggctgctg cgctagcttt tttggccact ggccgcgcgc    9900
agcgtaagcg gttaggctgg aaagcgaaag cattaagtgg ctcgctccct gtagccggag    9960
ggttattttc caagggttga gtcgcgggac ccccggttcg agtctcggac cggccggact   10020
gcggcgaacg ggggtttgcc tccccgtcat gcaagacccc gcttgcaaat tcctccggaa   10080
acagggacga gcccctttt tgcttttccc agatgcatcc ggtgctgcgg cagatgcgcc    10140
cccctcctca gcagcggcaa gagcaagagc agcggcagac atgcagggca ccctcccctc   10200
ctcctaccgc gtcaggaggg gcgacatccg cggttgacgc ggcagcagat ggtgattacg   10260 aaccccgcg gcgccgggcc cggcactacc tggacttgga ggagggcgag ggcctggcgc    10320
ggctaggagc gccctctcct gagcggtacc caagggtgca gctgaagcgt gatacgcgtg   10380
aggcgtacgt gccgcggcag aacctgtttc gcgaccgcga gggagaggag cccgaggaga   10440
tgcgggatcg aaagttccac gcagggcgcg agctgcggca tggcctgaat cgcgagcggt   10500
tgctgcgcga ggaggacttt gagcccgacg cgcgaaccgg gattagtccc gcgcgcgcac   10560
acgtggcggc cgccgacctg gtaaccgcat acgagcagac ggtgaaccag gagattaact   10620
ttcaaaaaag ctttaacaac cacgtgcgta cgcttgtggc gcgcgaggag gtggctatag   10680
gactgatgca tctgtgggac tttgtaagcg cgctggagca aaacccaaat agcaagccgc   10740
tcatggcgca gctgttcctt atagtgcagc acagcaggga caacgaggca ttcagggatg   10800
cgctgctaaa catagtagag cccgagggcc gctggctgct cgatttgata aacatcctgc   10860
agagcatagt ggtgcaggag cgcagcttga gcctggctga caaggtggcc gccatcaact   10920
attccatgct tagcctgggc aagttttacg cccgcaagat ataccatacc ccttacgttc   10980
ccatagacaa ggaggtaaag atcgagggt tctacatgcg catggcgctg aaggtgctta   11040
ccttgagcga cgacctgggc gtttatcgca acgagcgcat ccacaaggcc gtgagcgtga   11100
gccggcggcg cgagctcagc gaccgcgagc tgatgcacag cctgcaaagg gccctggctg   11160
gcacgggcag cggcgataga gaggccgagt cctactttga cgcgggcgct gacctgcgct   11220 gggcccaag ccgacgcgcc ctggaggcag ctggggccgg acctgggctg gcggtggcac    11280
ccgcgcgcgc tggcaacgtc ggcggcgtgg aggaatatga cgaggacgat gagtacgagc   11340
cagaggacgg cgagtactaa gcggtgatgt ttctgatcag atgatgcaag acgcaacgga   11400
cccggcggtg cgggcggcgc tgcagagcca gccgtccggc cttaactcca cggacgactg   11460
gcgccaggtc atggaccgca tcatgtcgct gactgcgcgc aatcctgacg cgttccggca   11520
gcagccgcag gccaaccggc tctccgcaat tctggaagcg gtggtcccgg cgcgcgcaaa   11580
ccccacgcac gagaaggtgc tggcgatcgt aaacgcgctg gccgaaaaca gggccatccg   11640
gcccgacgag gccggcctgg tctacgacgc gctgcttcag cgcgtggctc gttacaacag   11700
cggcaacgtg cagaccaacc tggaccggct ggtgggggat gtgcgcgagg ccgtggcgca   11760
gcgtgagcgc gcgcagcagc agggcaacct gggctccatg gttgcactaa cgccttcct    11820 gagtacacag cccgccaacg tgccgcgggg acaggaggac tacaccaact tgtgagcgc    11880 actgcggcta atggtgactg agacaccgca aagtgaggtg taccagtctg gccagacta    11940 tttttttccag accagtagac aaggcctgca gaccgtaaac ctgagccagg cttttcaaaaa  12000 cttgcagggg ctgtgggggg tgcgggctcc cacaggcgac cgcgcgaccg tgtctagctt   12060
```

```
gctgacgccc aactcgcgcc tgttgctgct gctaatagcg cccttcacgg acagtggcag   12120
cgtgtcccgg gacacatacc taggtcactt gctgacactg taccgcgagg ccataggtca   12180
ggcgcatgtg gacgagcata ctttccagga gattacaagt gtcagccgcg cgctggggca   12240
ggaggacacg ggcagcctgg aggcaaccct aaactacctg ctgaccaacc ggcggcagaa   12300
gatcccctcg ttgcacagtt taaacagcga ggaggagcgc attttgcgct acgtgcagca   12360
gagcgtgagc cttaacctga tgcgcgacgg ggtaacgccc agcgtggcgc tggacatgac   12420
cgcgcgcaac atggaaccgg gcatgtatgc ctcaaaccgg ccgtttatca accgcctaat   12480
ggactacttg catcgcgcgg ccgccgtgaa ccccgagtat ttcaccaatg ccatcttgaa   12540
cccgcactgg ctaccgcccc ctggtttcta caccggggga ttcgaggtgc ccgagggtaa   12600
cgatggattc ctctgggacg acatagacga cagcgtgttt tccccgcaac cgcagaccct   12660
gctagagttg caacagcgcg agcaggcaga ggcggcgctg cgaaaggaaa gcttccgcag   12720
gccaagcagc ttgtccgatc taggcgctgc ggccccgcgg tcagatgcta gtagcccatt   12780
tccaagcttg atagggtctc ttaccagcac tcgcaccacc cgcccgcgcc tgctgggcga   12840
ggaggagtac ctaaacaact cgctgctgca gccgcagcgc gaaaaaaacc tgcctccggc   12900
atttcccaac aacgggatag agagcctagt ggacaagatg agtagatgga agacgtacgc   12960
gcaggagcac agggacgtgc caggcccgcg cccgcccacc cgtcgtcaaa ggcacgaccg   13020
tcagcggggt ctggtgtggg aggacgatga ctcggcagac gacagcagcg tcctggattt   13080
gggagggagt ggcaacccgt ttgcgcacct tcgccccagg ctggggagaa tgttttaaaa   13140 aaaaaaagc atgatgcaaa ataaaaaact caccaaggcc atggcaccga gcgttggttt   13200
tcttgtattc cccttagtat gcggcgcgcg gcgatgtatg aggaaggtcc tcctccctcc   13260
tacgagagtg tggtgagcgc ggcgccagtg gcggcggcgc tgggttctcc cttcgatgct   13320
cccctggacc cgccgtttgt gcctccgcgg tacctgcggc ctaccggggg gagaaacagc   13380
atccgttact ctgagttggc acccctattc gacaccaccc gtgtgtacct ggtggacaac   13440
aagtcaacgg atgtggcatc cctgaactac cagaacgacc acagcaactt tctgaccacg   13500
gtcattcaaa acaatgacta cagcccgggg gaggcaagca cacagaccat caatcttgac   13560
gaccggtcgc actggggcgg cgacctgaaa accatcctgc ataccaacat gccaaatgtg   13620
aacgagttca tgtttaccaa taagtttaag gcgcgggtga tggtgtcgcg cttgcctact   13680
aaggacaatc aggtggagct gaaatacgag tgggtggagt tcacgctgcc cgagggcaac   13740
tactccgaga ccatgaccat agaccttatg aacaacgcga tcgtggagca ctacttgaaa   13800
gtgggcagac agaacggggt tctggaaagc gacatcgggg taaagtttga cacccgcaac   13860
ttcagactgg ggtttgaccc cgtcactggt cttgtcatgc ctgggggtata tacaaacgaa   13920 gccttccatc cagacatcat tttgctgcca ggatgcgggg tggacttcac ccacagccgc   13980
ctgagcaact tgttgggcat ccgcaagcgg caacccttcc aggagggctt taggatcacc   14040
tacgatgatc tggagggtgg taacattccc gcactgttgg atgtggacgc ctaccaggcg   14100
agcttgaaag atgacaccga acagggcggg ggtggcgcag gcggcagcaa cagcagtggc   14160
agcggcgcgg aagagaactc caacgcggca gccgcggcaa tgcagccggt ggaggacatg   14220
aacgatcatg ccattcgcgg cgacaccttt gccacacggg ctgaggagaa gcgcgctgag   14280
gccgaagcag cggccgaagc tgccgccccc gctgcgcaac ccgaggtcga gaagcctcag   14340
aagaaaccgg tgatcaaacc cctgacagag gacagcaaga aacgcagtta caacctaata   14400
```

```
agcaatgaca gcaccttcac ccagtaccgc agctggtacc ttgcatacaa ctacggcgac   14460
cctcagaccg gaatccgctc atggaccctg ctttgcactc ctgacgtaac ctgcggctcg   14520
gagcaggtct actggtcgtt gccagacatg atgcaagacc ccgtgacctt ccgctccacg   14580
cgccagatca gcaactttcc ggtggtgggc gccgagctgt tgcccgtgca ctccaagagc   14640
ttctacaacg accaggccgt ctactcccaa ctcatccgcc agtttacctc tctgacccac   14700
gtgttcaatc gctttcccga gaaccagatt ttggcgcgcc cgccagcccc caccatcacc   14760
accgtcagtg aaaacgttcc tgctctcaca gatcacggga cgctaccgct gcgcaacagc   14820
atcggaggag tccagcgagt gaccattact gacgccagac gccgcacctg cccctacgtt   14880
tacaaggccc tgggcatagt ctcgccgcgc gtcctatcga gccgcacttt ttgagcaagc   14940
atgtccatcc ttatatcgcc cagcaataac acaggctggg gcctgcgctt cccaagcaag   15000
atgtttggcg gggccaagaa cgctccgac caacacccag tgcgcgtgcg cgggcactac   15060
cgcgcgccct ggggcgcgca caaacgcggc cgcactgggc gcaccaccgt cgatgacgcc   15120
atcgacgcgg tggtggagga ggcgcgcaac tacacgccca cgccgccacc agtgtccaca   15180
gtggacgcgg ccattcagac cgtggtgcgc ggagcccggc gctatgctaa aatgaagaga   15240
cggcggaggc gcgtagcacg tcgccaccgc cgccgacccg cgactgccgc caacgcgcg    15300 gcggcggccc tgcttaaccg cgcacgtcgc accggccgac gggcggccat gcgggccgct   15360
cgaaggctgg ccgcgggtat tgtcactgtg cccccaggt ccaggcgacg agcggccgcc    15420
gcagcagccg cggccattag tgctatgact cagggtcgca ggggcaacgt gtattgggtg   15480
cgcgactcgg ttagcggcct gcgcgtgccc gtgcgcaccc gccccccgcg caactagatt   15540
gcaagaaaaa actacttaga ctcgtactgt tgtatgtatc cagcggcggc ggcgcgcaac   15600
gaagctatgt ccaagcgcaa aatcaaagaa gagatgctcc aggtcatcgc gccggagatc   15660
tatggccccc cgaagaagga agagcaggat tacaagcccc gaaagctaaa gcgggtcaaa   15720
aagaaaaaga aagatgatga tgatgaactt gacgacgagg tggaactgct gcacgctacc   15780
gcgcccaggc gacgggtaca gtggaaaggt cgacgcgtaa aacgtgtttt gcgacccggc   15840
accaccgtag tctttacgcc cggtgagcgc tccacccgca cctacaagcg cgtgtatgat   15900
gaggtgtacg gcgacgagga cctgcttgag caggccaacg agcgcctcgg ggagtttgcc   15960
tacgaaaagc ggcataagga catgctggcg ttgccgctgg acgagggcaa cccaacacct   16020
agcctaaagc ccgtaacact gcagcaggtg ctgcccgcgc ttgcaccgtc cgaagaaaag   16080
cgcggcctaa agcgcgagtc tggtgacttg gcacccaccg tgcagctgat ggtacccaag   16140
cgccagcgac tggaagatgt cttggaaaaa atgaccgtgg aacctgggct ggagcccgag   16200
gtccgcgtgc ggccaatcaa gcaggtggcg ccgggactgg gcgtgcagac cgtggacgtt   16260
cagataccca ctaccagtag caccagtatt gccaccgcca cagagggcat ggagacacaa   16320
acgtccccgg ttgcctcagc ggtggcggat gccgcggtgc aggcggtcgc tgcggccgcg   16380
tccaagacct ctacggaggt gcaaacggac ccgtggatgt ttcgcgtttc agccccccgg   16440
cgcccgcgcg gttcgaggaa gtacggcgcc gccagcgcgc tactgcccga atatgcccta   16500
catccttcca ttgcgcctac ccccggctat cgtggctaca cctaccgccc cagaagacga   16560
gcaactaccc gacgccgaac caccactgga acccgccgcc gcgtcgccg  tcgccagccc   16620 gtgctggccc cgatttccgt gcgcagggtg gctcgcgaag gaggcaggac cctggtgctg   16680
ccaacagcgc gctaccaccc cagcatcgtt taaaagccgg tctttgtggt tcttgcagat   16740
atggccctca cctgccgcct ccgtttcccg gtgccgggat tccgaggaag aatgcaccgt   16800
```

```
aggaggggca tggccggcca cggcctgacg ggcggcatgc gtcgtgcgca ccaccggcgg   16860
cggcgcgcgt cgcaccgtcg catgcgcggc ggtatcctgc ccctccttat tccactgatc   16920
gccgcggcga ttggcgccgt gcccggaatt gcatccgtgg ccttgcaggc gcagagacac   16980
tgattaaaaa caagttgcat gtggaaaaat caaaataaaa agtctggact ctcacgctcg   17040
cttggtcctg taactatttt gtagaatgga agacatcaac tttgcgtctc tggccccgcg   17100
acacggctcg cgcccgttca tgggaaactg caagatatc ggcaccagca atatgagcgg    17160
tggcgccttc agctggggct cgctgtggag cggcattaaa aatttcggtt ccaccgttaa   17220
gaactatggc agcaaggcct ggaacagcag cacaggccag atgctgaggg ataagttgaa   17280
agagcaaaat ttccaacaaa aggtggtaga tggcctggcc tctggcatta gcggggtggt   17340
ggacctggcc aaccaggcag tgcaaaataa gattaacagt aagcttgatc cccgccctcc   17400
cgtagaggag cctccaccgg ccgtggagac agtgtctcca gaggggcgtg gcgaaaagcg   17460
tccgcgcccc gacagggaag aaactctggt gacgcaaata gacgagcctc cctcgtacga   17520
ggaggcacta aagcaaggcc tgcccaccac ccgtcccatc gcgcccatgg ctaccggagt   17580
gctgggccag cacacacccg taacgctgga cctgcctccc cccgccgaca cccagcagaa   17640
acctgtgctg ccaggcccga ccgccgttgt tgtaacccgt cctagccgcg cgtccctgcg   17700
ccgcgccgcc agcggtccgc gatcgttgcg gcccgtagcc agtggcaact ggcaaagcac   17760
actgaacagc atcgtgggtc tgggggtgca atccctgaag cgccgacgat gcttctgaat   17820
agctaacgtg tcgtatgtgt gtcatgtatg cgtccatgtc gccgcagag gagctgctga    17880 gccgccgcgc gcccgctttc caagatggct acccctcga tgatgccgca gtggtcttac    17940
atgcacatct cgggccagga cgcctcggag tacctgagcc ccgggctggt gcagtttgcc   18000
cgcgccaccg agacgtactt cagcctgaat aacaagttta gaaaccccac ggtggcgcct   18060
acgcacgacg tgaccacaga ccggtcccag cgtttgacgc tgcggttcat ccctgtggac   18120
cgtgaggata ctgcgtactc gtacaaggcg cggttcaccc tagctgtggg tgataaccgt   18180
gtgctgacag tggcttccac gtactttgac atccgcggcg tgctggacag gggccctact   18240
tttaagccct actctggcac tgcctacaac gccctggctc ccaagggtgc cccaaatcct   18300
tgcgaatggg atgaagctgc tactgctctt gaaataaacc tagaagaaga ggacgatgac   18360
aacgaagacg aagtagacga gcaagctgag cagcaaaaaa ctcacgtatt tgggcaggcg   18420
ccttattctg gtataaatat tacaaaggag ggtattcaaa taggtgtcga aggtcaaaca   18480
cctaaatatg ccgataaaac atttcaacct gaacctcaaa taggagaatc tcagtggtac   18540
gaaactgaaa ttaatcatgc agctgggaga gtccttaaaa agactacccc aatgaaacca   18600
tgttacggtt catatgcaaa acccacaaat gaaaatggag gcaaggcat tcttgtaaag     18660 caacaaaatg gaaagctaga aagtcaagtg gaaatgcaat ttttctcaac tactgaggcg   18720
accgcaggca atggtgataa cttgactcct aaagtggtat tgtacagtga agatgtagat   18780
atagaaaccc cagacactca tatttcttac atgcccacta ttaaggaagg taactcacga   18840
gaactaatgg gccaacaatc tatgcccaac aggcctaatt acattgcttt tagggacaat   18900
tttattggtc taatgtatta caacagcacg ggtaatatgg gtgttctggc gggccaagca   18960
tcgcagttga atgctgttgt agatttgcaa gacagaaaca cagagctttc ataccagctt   19020
ttgcttgatt ccattggtga tagaaccagg tactttttcta tgtggaatca ggctgttgac   19080
agctatgatc cagatgttag aattattgaa aatcatggaa ctgaagatga acttccaaat   19140
```

```
tactgctttc cactgggagg tgtgattaat acagagactc ttaccaaggt aaaacctaaa    19200
acaggtcagg aaaatggatg ggaaaaagat gctacagaat tttcagataa aaatgaaata    19260
agagttggaa ataattttgc catggaaatc aatctaaatg ccaacctgtg gagaaatttc    19320
ctgtactcca acatagcgct gtatttgccc gacaagctaa agtacagtcc ttccaacgta    19380
aaaatttctg ataacccaaa cacctacgac tacatgaaca agcgagtggt ggctcccggg    19440
ttagtggact gctacattaa ccttggagca cgctggtccc ttgactatat ggacaacgtc    19500
aacccattta accaccaccg caatgctggc ctgcgctacc gctcaatgtt gctgggcaat    19560
ggtcgctatg tgcccttcca catccaggtg cctcagaagt tctttgccat taaaaacctc    19620
cttctcctgc cgggctcata cacctacgag tggaacttca ggaaggatgt taacatggtt    19680
ctgcagagct ccctaggaaa tgacctaagg gttgacggag ccagcattaa gtttgatagc    19740
atttgccttt acgccacctt cttccccatg gcccacaaca ccgcctccac gcttgaggcc    19800
atgcttagaa acgacaccaa cgaccagtcc tttaacgact atctctccgc cgccaacatg    19860 ctctaccctaa tacccgccaa cgctaccaac gtgcccatat ccatcccctc ccgcaactgg    19920
gcggctttcc gcggctgggc cttcacgcgc cttaagacta aggaaacccc atcactgggc    19980
tcgggctacg acccttatta cacctactct ggctctatac cctacctaga tggaaccttt    20040
tacctcaacc acacctttaa gaaggtggcc attacctttg actcttctgt cagctggcct    20100
ggcaatgacc gcctgcttac ccccaacgag tttgaaatta gcgctcagt tgacggggag    20160 ggttacaacg ttgcccagtg taacatgacc aaagactggt tcctggtaca aatgctagct    20220
aactacaaca ttggctacca gggcttctat atcccagaga gctacaagga ccgcatgtac    20280
tccttcttta gaaacttcca gcccatgagc cgtcaggtgg tggatgatac taaatacaag    20340
gactaccaac aggtgggcat cctacaccaa cacaacaact ctggatttgt tggctaccttt    20400 gcccccacca tgcgcgaagg acaggcctac cctgctaact tcccctatcc gcttataggc    20460
aagaccgcag ttgacagcat tacccagaaa agttctttt gcgatcgcac cctttggcgc    20520
atcccattct ccagtaactt tatgtccatg ggcgcactca cagacctggg ccaaaacctt    20580
ctctacgcca actccgccca cgcgctagac atgacttttg aggtggatcc catggacgag    20640
cccacccttc tttatgtttt gtttgaagtc tttgacgtgg tccgtgtgca ccggccgcac    20700
cgcggcgtca tcgaaaccgt gtacctgcgc acgcccttct cggccggcaa cgccacaaca    20760
taaagaagca agcaacatca acaacagctg ccgccatggg ctccagtgag caggaactga    20820
aagccattgt caaagatctt ggttgtgggc cattttttt gggcacctat gacaagcgct    20880
ttccaggctt tgtttctcca cacaagctcg cctgcgccat agtcaatacg gccggtcgcg    20940
agactggggg cgtacactgg atggcctttg cctggaaccc gcactcaaaa acatgctacc    21000
tctttgagcc cttttggcttt tctgaccagc gactcaagca ggtttaccag tttgagtacg    21060
agtcactcct gcgccgtagc gccattgctt cttcccccga ccgctgtata acgctggaaa    21120
agtccaccca aagcgtacag gggcccaact cggccgcctg tggactattc tgctgcatgt    21180
ttctccacgc ctttgccaac tggccccaaa ctcccatgga tcacaacccc accatgaacc    21240
ttattaccgg ggtacccaac tccatgctca acagtcccca ggtacagccc accctgcgtc    21300
gcaaccagga acagctctac agcttcctgg agcgccactc gccctacttc cgcagccaca    21360
gtgcgcagat taggagcgcc acttcttttt gtcacttgaa aaacatgtaa aaataatgta    21420
ctagagacac tttcaataaa ggcaaatgct tttatttgta cactctcggg tgattattta    21480 ccccaccct tgccgtctgc gccgtttaaa aatcaaaggg gttctgccgc gcatcgctat    21540
```

```
gcgccactgg cagggacacg ttgcgatact ggtgtttagt gctccactta aactcaggca   21600
caaccatccg cggcagctcg gtgaagtttt cactccacag gctgcgcacc atcaccaacg   21660
cgtttagcag gtcgggcgcc gatatcttga agtcgcagtt ggggcctccg ccctgcgcgc   21720
gcgagttgcg atacacaggg ttgcagcact ggaacactat cagcgccggg tggtgcacgc   21780
tggccagcac gctcttgtcg gagatcagat ccgcgtccag gtcctccgcg ttgctcaggg   21840
cgaacggagt caactttggt agctgccttc ccaaaaaggg cgcgtgccca ggctttgagt   21900
tgcactcgca ccgtagtggc atcaaaaggt gaccgtgccc ggtctgggcg ttaggataca   21960
gcgcctgcat aaaagccttg atctgcttaa aagccacctg agcctttgcg ccttcagaga   22020
agaacatgcc gcaagacttg ccggaaaact gattggccgg acaggccgcg tcgtgcacgc   22080
agcaccttgc gtcggtgttg gagatctgca ccacatttcg gccccaccgg ttcttcacga   22140
tcttggcctt gctagactgc tccttcagcg cgcgctgccc gttttcgctc gtcacatcca   22200
tttcaatcac gtgctcctta tttatcataa tgcttccgtg tagacactta agctcgcctt   22260
cgatctcagc gcagcggtgc agccacaacg cgcagcccgt gggctcgtga tgcttgtagg   22320
tcacctctgc aaacgactgc aggtacgcct gcaggaatcg ccccatcatc gtcacaaagg   22380
tcttgttgct ggtgaaggtc agctgcaacc cgcggtgctc ctcgttcagc caggtcttgc   22440
atacggccgc cagagcttcc acttggtcag gcagtagttt gaagttcgcc tttagatcgt   22500
tatccacgtg gtacttgtcc atcagcgcgc gcgcagcctc catgcccttc tcccacgcag   22560
acacgatcgg cacactcagc gggttcatca ccgtaatttc actttccgct tcgctgggct   22620
cttcctcttc ctcttgcgtc cgcataccac gcgccactgg gtcgtcttca ttcagccgcc   22680
gcactgtgcg cttacctcct ttgccatgct tgattagcac cggtgggttg ctgaaaccca   22740
ccatttgtag cgccacatct tctctttctt cctcgctgtc cacgattacc tctggtgatg   22800
gcgggcgctc gggcttggga aagggcgct tcttttctt cttgggcgca atggccaaat   22860
ccgccgccga ggtcgatggc cgcgggctgg gtgtgcgcgg caccagcgcg tcttgtgatg   22920
agtcttcctc gtcctcggac tcgatacgcc gcctcatccg ctttttggg ggcgcccggg   22980 gaggcggcgg cgacggggac ggggacgaca cgtcctccat ggttggggga cgtcgcgccg   23040
caccgcgtcc gcgctcgggg gtggtttcgc gctgctcctc ttcccgactg gccatttcct   23100
tctcctatag gcagaaaaag atcatggagt cagtcgagaa gaaggacagc ctaaccgccc   23160
cctctgagtt cgccaccacc gcctccaccg atgccgccaa cgcgcctacc accttccccg   23220
tcgaggcacc cccgcttgag gaggaggaag tgattatcga gcaggaccca ggttttgtaa   23280
gcgaagacga cgaggaccgc tcagtaccaa cagaggataa aaagcaagac caggacaacg   23340
cagaggcaaa cgaggaacaa gtcgggcggg gggacgaaag gcatggcgac tacctagatg   23400
tgggagacga cgtgctgttg aagcatctgc agcgccagtg cgccattatc tgcgacgcgt   23460
tgcaagagcg cagcgatgtg cccctcgcca tagcggatgt cagccttgcc tacgaacgcc   23520
acctattctc accgcgcgta ccccccaaac gccaagaaaa cggcacatgc gagcccaacc   23580
cgcgcctcaa cttctacccc gtatttgccg tgccagaggt gcttgccacc tatcacatct   23640 tttccaaaa ctgcaagata cccctatcct gccgtgccaa ccgcagccga gcggacagc   23700 agctggcctt gcggcagggc gctgtcatac ctgatatcgc ctcgctcaac gaagtgccaa   23760
aaatctttga gggtcttgga cgcgacgaga agcgcgcggc aaacgctctg caacaggaaa   23820
acagcgaaaa tgaaagtcac tctggagtgt tggtggaact cgagggtgac aacgcgcgcc   23880
```

```
tagccgtact aaaacgcagc atcgaggtca cccactttgc ctacccggca cttaacctac    23940
cccccaaggt catgagcaca gtcatgagtg agctgatcgt gcgccgtgcg cagcccctgg    24000
agagggatgc aaatttgcaa gaacaaacag aggagggcct acccgcagtt ggcgacgagc    24060
agctagcgcg ctggcttcaa acgcgcgagc ctgccgactt ggaggagcga cgcaaactaa    24120
tgatggccgc agtgctcgtt accgtggagc ttgagtgcat gcagcggttc tttgctgacc    24180
cggagatgca gcgcaagcta gaggaaacat tgcactacac ctttcgacag ggctacgtac    24240
gccaggcctg caagatctcc aacgtggagc tctgcaacct ggtctcctac cttggaattt    24300
tgcacgaaaa ccgccttggg caaaacgtgc ttcattccac gctcaagggc gaggcgcgcc    24360
gcgactacgt ccgcgactgc gtttacttat ttctatgcta cacctggcag acggccatgg    24420
gcgtttggca gcagtgcttg gaggagtgca acctcaagga gctgcagaaa ctgctaaagc    24480
aaaacttgaa ggacctatgg acggccttca acgagcgctc cgtggccgcg cacctggcgg    24540
acatcatttt ccccgaacgc ctgcttaaaa ccctgcaaca gggtctgcca gacttcacca    24600
gtcaaagcat gttgcagaac tttaggaact ttatcctaga gcgctcagga atcttgcccg    24660
ccacctgctg tgcacttcct agcgactttg tgcccattaa gtaccgcgaa tgccctccgc    24720
cgctttgggg ccactgctac cttctgcagc tagccaacta ccttgcctac cactctgaca    24780
taatggaaga cgtgagcggt gacggtctac tggagtgtca ctgtcgctgc aacctatgca    24840
ccccgcaccg ctccctggtt tgcaattcgc agctgcttaa cgaaagtcaa attatcggta    24900
cctttgagct gcagggtccc tcgcctgacg aaaagtccgc ggctccgggg ttgaaactca    24960
ctccgggget gtggacgtcg gcttaccttc gcaaatttgt acctgaggac taccacgccc    25020
acgagattag gttctacgaa gaccaatccc gcccgccaaa tgcggagctt accgcctgcg    25080
tcattaccca gggccacatt cttggccaat tgcaagccat caacaaagcc cgccaagagt    25140
ttctgctacg aaagggacgg gggttttact tggacccccca gtccggcgag gagctcaacc    25200
caatccccc gccgccgcag ccctatcagc agcagccgcg ggcccttgct tcccaggatg    25260
gcacccaaaa agaagctgca gctgccgccg ccacccacgg acgaggagga atactgggac    25320
agtcaggcag aggaggtttt ggacgaggag gaggaggaca tgatggaaga ctgggagagc    25380
ctagacgagg aagcttccga ggtcgaagag gtgtcagacg aaacaccgtc accctcggtc    25440
gcattcccct cgccggcgcc ccagaaatcg gcaaccggtt ccagcatggc tacaacctcc    25500
gctcctcagg cgccgccggc actgcccgtt cgccgaccca accgtagatg ggacaccact    25560
ggaaccaggg ccggtaagtc caagcagccg ccgccgttag cccaagagca acaacagcgc    25620
caaggctacc gctcatggcg cgggcacaag aacgccatag ttgcttgctt gcaagactgt    25680
gggggcaaca tctccttcgc ccgccgcttt cttctctacc atcacggcgt ggccttcccc    25740
cgtaacatcc tgcattacta ccgtcatctc tacagcccat actgcaccgg cggcagcggc    25800
agcggcagca acagcagcgg ccacacagaa gcaaaggcga ccggatagca agactctgac    25860
aaagcccaag aaatccacag cggcggcagc agcaggagga ggagcgctgc gtctggcgcc    25920
caacgaaccc gtatcgaccc gcgagcttag aaacaggatt tttcccactc tgtatgctat    25980
atttcaacag agcaggggcc aagaacaaga gctgaaaata aaaaacaggt ctctgcgatc    26040
cctcacccgc agctgcctgt atcacaaaag cgaagatcag cttcggcgca cgctggaaga    26100
cgcggaggct ctcttcagta aatactgcgc gctgactctt aaggactagt tcgcgccct    26160
ttctcaaatt taagcgcgaa aactacgtca tctccagcgg ccacacccgg cgccagcacc    26220
tgtcgtcagc gccattatga gcaaggaaat tcccacgccc tacatgtgga gttaccagcc    26280
```

-continued

| | | | | | |
|---|---|---|---|---|---|
| acaaatggga | cttgcggctg | gagctgccca | agactactca | acccgaataa | actacatgag | 26340 |
| cgcgggaccc | cacatgatat | cccgggtcaa | cggaatccgc | gcccaccgaa | accgaattct | 26400 |
| cttggaacag | gcggctatta | ccaccacacc | tcgtaataac | cttaatcccc | gtagttggcc | 26460 |
| cgctgccctg | gtgtaccagg | aaagtccgc | tcccaccact | gtggtacttc | ccagagacgc | 26520 |
| ccaggccgaa | gttcagatga | ctaactcagg | ggcgcagctt | gcgggcggct | tcgtcacag | 26580 |
| ggtgcggtcg | cccgggcagg | gtataactca | cctgacaatc | agagggcgag | gtattcagct | 26640 |
| caacgacgag | tcggtgagct | cctcgcttgg | tctccgtccg | gacgggacat | ttcagatcgg | 26700 |
| cggcgccggc | cgctcttcat | tcacgcctcg | tcaggcaatc | ctaactctgc | agacctcgtc | 26760 |
| ctctgagccg | cgctctggag | gcattggaac | tctgcaattt | attgaggagt | ttgtgccatc | 26820 |
| ggtctacttt | aacccttct | cgggacctcc | cggccactat | ccggatcaat | ttattcctaa | 26880 |
| cttttgacgcg | gtaaaggact | cggcggatgg | ctacgactga | atgttaagtg | gagaggcaga | 26940 |
| gcaactgcgc | ctgaaacacc | tggtccactg | tcgccgccac | aagtgctttg | cccgcgactc | 27000 |
| cggtgagttt | tgctactttg | aattgcccga | ggatcatatc | gagggcccgg | cgcacggcgt | 27060 |
| ccggcttacc | gcccagggag | agcttgcccg | tagcctgatt | cggagtttta | cccagcgccc | 27120 |
| cctgctagtt | gagcgggaca | ggggaccctg | tgttctcact | gtgatttgca | actgtcctaa | 27180 |
| ccctggatta | catcaagatc | tttgttgcca | tctctgtgct | gagtataata | aatacagaaa | 27240 |
| ttaaaatata | ctggggctcc | tatcgccatc | ctgtaaacgc | caccgtcttc | acccgcccaa | 27300 |
| gcaaaccaag | gcgaacctta | cctggtactt | ttaacatctc | tccctctgtg | atttacaaca | 27360 |
| gtttcaaccc | agacggagtg | agtctacgag | agaacctctc | cgagctcagc | tactccatca | 27420 |
| gaaaaaacac | caccctcctt | acctgccggg | aacgtacg | | | 27458 |

<210> SEQ ID NO 4
<211> LENGTH: 7258
<212> TYPE: DNA
<213> ORGANISM: adenovirus

<400> SEQUENCE: 4

| | | | | | |
|---|---|---|---|---|---|
| atggagactg | ggttgtatac | tcgcccgagt | gaaaggtgtt | actcactgat | cgagttgata | 60 |
| gaactggagc | cccacgaact | agaagtggca | ctcgctcttg | cgacccaccg | tgctttggcc | 120 |
| actcatcgag | gcctttacgt | tgcactccat | atctccagtg | agcgtgggct | cctggaagtc | 180 |
| gcactgatgg | agaccaccca | cagagggatt | aattccgaac | gacctagaag | tgagagatct | 240 |
| gagcggttag | agactcacag | agtagctttg | acacatcgtg | ctctggcggg | gctatatggg | 300 |
| ttactttatt | ccgtagcgtt | gacccatagg | atggaaacat | ccgaacgctg | ctattcctta | 360 |
| tacagttctg | agcggtctga | gcgcggtata | aatagtgaac | ggctggagtt | ggaagcttcc | 420 |
| aactcggaga | gggggcttta | cgcttcgaac | gggataaacc | tttactcggc | atctaatact | 480 |
| tacagactcg | agactcaccg | tacaaggccc | acctacaggg | gtatcaatgg | tatcaacctg | 540 |
| tattcgccaa | ggggtctcta | tggcataaat | ccccgaccgc | gattatattc | gcttgaattg | 600 |
| gagctcatag | aaacctacag | aacgcgtcca | gccttagcca | gtgagcgtac | gcaccgagca | 660 |
| aggggggggcc | tgtctgaacg | aggcctttac | gtggctctac | cccgagcttc | acccgcgaga | 720 |
| ggccctcatg | aaacccatcg | tggattatac | tcggaaagag | gactttattc | tgagcggggt | 780 |
| ctatacacac | atcgtgcgtc | cccccccccat | gaaacacatc | gactgagac | gcatagacta | 840 |
| atagaatcgg | agagaagtga | gcgagttgca | ttggggatca | atgcgttggc | cggtctcgct | 900 |

```
tccccgctcg aagccttagc ggttgcgctg acctatcgga cttatcgctg ttatagcgga    960
attaatgcgt ctaacgcctc ccctacgtat cggagcgaaa gaacctatag accccggttg   1020
gagacacatc gcccgcatga ggggttatac gctttagcgg ggctttatac tcatcgactc   1080
tattcgcttg agggtttaca cgaactctac agcggattat acggtctcta cggcctttac   1140
ggcttataca gtgaaagagg tctctatggc ttgtacggtt tgtacggtct gtactcagag   1200
cggggcttgt acggcttgta tggtctctac gggctgtaca gtgagagggg actagtggct   1260
ctagggatta acctagagct tgaggggctt ggaatcaaca gtgagcgagg cctctatgcg   1320
ttggcgggc  tgttggaggt tgcactggcg cgaggaccga gaggtctata cacacatcga   1380
tcggaacgtg ttgccctact ttatagccat gaaagcgagc ggtgctactc gttgtactcg   1440
gcattagcct cagagcgagg tctttataca tacagagcac tggcacctca cgaaacacac   1500
cgagcgtcaa atacctatag aacgcgaccc cttgaaggac tttacactcg gcccgtcgct   1560
ttactgtact ctggaataaa cgcacgaggt cctcgtggcc tttaccatat ctctggccta   1620
tatctagaag ggctcactag gcctcatgag gggttgtacg cgagccccca tgaacccat    1680
gagccaaggg gattgtatag cgagcgaggg ctttacgcat ctaaccacga acatataagc   1740
acttatcgag cgagcaacgg tctgctctat tcgccccacg aactctattc cggactttac   1800
ttatattcgg ctttggctac tcataggtta gaaacacata gagccctcgc agcctctcct   1860
ttatatagct ccgaaaggtc agagcgatca gagagaacgc acagggctct ggccacttat   1920
aggatggaga ctgggattaa ccttgaatcg gagcgctcgg agcgactcga aacgcaccga   1980
ccacacgaag gactggcgag ccctagtgag agagctctag cggtggcttt gacatacaga   2040
cctcatgagt gttacagcgc cctagcagca cgcggactgg aggcgagggg cgcgagtaat   2100
acaagaccgg cctcgcctgg acttccacga atggagacgg cttctccaac gtacaggacc   2160
agaccggggc tctacggtat caatggcttg tatacccaca gaacccatcg tgttgcgctt   2220
acccatcgcg ttgctctttc ggagcgttca gaaagaggcc tgtatgggtt atacggcctt   2280
tatggcctat acgcttcccc cgtcgccttg ggaataaatc tggaggtcgc cttgggaata   2340
aattcagaac gaggattata cgcacttgcg gggctagtgg cgttattata ttcacttttac  2400
tctccgaggg gttttgtatgc cctagctagc gaacgagtcg cgcttctgta cagtgtggca   2460
ctcagtgaac ggtgctatag cttatacagc gctctagcgt ctgagcgtgg cctttacaca   2520
tatcgtacgc accgtcccca cgagactcat cgcgcgcgtg gcacctacag gacccacagg   2580
atggaaacac atatttcaac tcggccagtt gctttagccc gcggggcat  caatgctcta   2640
gcgcctcggg gattatacgg aatcaacggc ctctacttag agggcctaac taggccgcat   2700
gaaggtctgt acacatatag acatgaagcg tctaatccac gttccgagag gcacgtgggg   2760
ggactataca cttacagaac tcatcgggcc agtaacacct atcgagcatt agcggcgagc   2820
ccgtctgagc gtgttgcact cttatatagt gggttatatg cgcgtgggcc acatgaaacc   2880
caccgtcatg agacacaccg gacacatcga gcatcaccct tgtactcgag cgaaagaacc   2940
cacagatcag aacggacaca tcgcgcgctc gcaacataca gaatggaaac cggtctgctt   3000
gagagcgaga ggtcggagcg tttggaggcg cgaggttcgg agcgcgggct ggcatcacca   3060
actcacagag cattagcaac ccaccgcaca tataggacct accggtgtta ttcggcctta   3120
gctgccagag ggacatacag gacctatcgc gcgtcccccg caagtcccca tattagcaca   3180
taccgatgct attccttgga ggcgagccca acgtatcgca cgaggccggg actttacggg   3240
atcaatggtt tgtatacaca ccgcacccat agggtggcgt taactcacag agtagcactc   3300
```

```
tccgagaggt cggaaagggg cctgtatggc ctgggattat acacacaccg gagcgaaaga    3360
acgcaccggg gtttatacag tgagcgcggc ctatacggct tgtattccga gcgtggatta    3420
tacggcctct actcagaacg gggtttatac gggctgtacg ccttagcagc gagtcccgct    3480
tcccctcatg aggtcgctct gttggaaact catcgtggga ttaactctga gcggcctcga    3540
gctttggcga ctcacaggct ggaatccgaa cgtctagaga gtgaacggcc tcgaggcttg    3600
tacgggttgg cccgagggc gctcgctacg caccgtctag agagtgagag atgctacagt    3660
gcccgagggg cgctagcctc agagcgaggt ataaactcag aacgcgtcgc tctgtcagaa    3720
agaacctacc ggatggagac agcctcgaat actagaccaa cttaccgagg cataaatggg    3780
attaatctct actcaccgag gggactttac ctttactcag cgctcgctcc ccgtctatat    3840
tccgcacgag ggacgagacc gcatgaaact taccgtgcat ctccgaccca ccgaagcgaa    3900
aggctataca gcgttgcgtt ggcccttgct tcggagcggg ggctatatgt agcactacct    3960
agagctttgg ccgcgagagg tccccacgag tccgaacggg gtctctattc agagagggga    4020
ctttactctg aacggggact gtatacccac agggcgtctc ctacttacag gtccgaacgg    4080
ctagagaccc accgacacga agccagtaac agtgagaggt tagaagggct tgcgttggca    4140
ggtcttgcgt cacctgccct ggcggctcta gctacgcatc gtacttatag aacgtatcga    4200
tgctattcag gcattaacgg tataaatacg aggccaagtg agaggagcga agagcgtca    4260 aacccgcgct tagaaacgca tcgccctcac gaaggattgt atggacttta tggactttat    4320
actcatcgat tatatagtgt ggcgttaggc ctacatgagc tttattcgca attgactcta    4380
tgtgggatat gctccagcgc tacaaccttg aagtcaggct tcctggatgt cagcatctga    4440
ctttggccag cacctgtccc gcggatttgt tccagtccaa ctacagcgac ccaccctaac    4500
agagatgacc aacacaacca acgcggccgc cgctaccgga cttacatcta ccacaaatac    4560
accccaagtt tctgcctttg tcaataactg ggataacttg ggcatgtggt ggttctccat    4620
agcgcttatg tttgtatgcc ttattattat gtggctcatc tgctgcctaa agcgcaaacg    4680
cgcccgacca cccatctata gtcccatcat tgtgctacac ccaaacaatg atggaatcca    4740
tagattggac ggactgaaac acatgttctt ttctcttaca gtatgattaa atgagacatg    4800
attcctcgag tttttatatt actgacccctt gttgcgcttt tttgtgcgtg ctccacattg    4860
gctgcggttt ctcacatcga agtagactgc attccagcct tcacagtcta tttgctttac    4920
ggatttgtca ccctcacgct catctgcagc ctcatcactg tggtcatcgc ctttatccag    4980
tgcattgact gggtctgtgt gcgctttgca tatctcagac accatcccca gtacagggac    5040
aggactatag ctgagcttct tagaattctt taattatgaa atttactgtg acttttctgc    5100
tgattatttg caccctatct gcgttttgtt ccccgacctc caagcctcaa agacatatat    5160
catgcagatt cactcgtata tggaatattc caagttgcta caatgaaaaa agcgatcttt    5220
ccgaagcctg gttatatgca atcatctctg ttatggtgtt ctgcagtacc atcttagccc    5280
tagctatata tccctacctt gacattggct ggaaacgaat agatgccatg aaccacccaa    5340
ctttccccgc gcccgctatg cttccactgc aacaagttgt tgccggcggc tttgtcccag    5400
ccaatcagcc tcgccccact tctcccaccc ccactgaaat cagctacttt aatctaacag    5460
gaggagatga ctgacaccct agatctagaa atggacggaa ttattacaga gcagcgcctg    5520
ctagaaagac gcagggcagc ggccgagcaa cagcgcatga atcaagagct ccaagacatg    5580
gttaacttgc accagtgcaa aaggggtatc ttttgtctgg taaagcaggc caaagtcacc    5640
```

-continued

| | |
|---|---|
| tacgacagta ataccaccgg acaccgcctt agctacaagt tgccaaccaa gcgtcagaaa | 5700 |
| ttggtggtca tggtgggaga aaagcccatt accataactc agcactcggt agaaaccgaa | 5760 |
| ggctgcattc actcaccttg tcaaggacct gaggatctct gcacccttat taagaccctg | 5820 |
| tgcggtctca aagatcttat tccctttaac taataaaaaa aaataataaa gcatcactta | 5880 |
| cttaaaatca gttagcaaat ttctgtccag tttattcagc agcacctcct tgccctcctc | 5940 |
| ccagctctgg tattgcagct tcctcctggc tgcaaacttt ctccacaatc taaatggaat | 6000 |
| gtcagtttcc tcctgttcct gtccatccgc acccactatc ttcatgttgt tgcagatgaa | 6060 |
| gcgcgcaaga ccgtctgaag ataccttcaa ccccgtgtat ccatatgaca cggaaaccgg | 6120 |
| tcctccaact gtgccttttc ttactcctcc ctttgtatcc cccaatgggt ttcaagagag | 6180 |
| tcccctggg gtactctctt tgcgcctatc cgaacctcta gttacctcca atggcatgct | 6240 |
| tgcgctcaaa atgggcaacg gcctctctct ggacgaggcc ggcaacctta cctcccaaaa | 6300 |
| tgtaaccact gtgagcccac ctctcaaaaa aaccaagtca aacataaacc tggaaatatc | 6360 |
| tgcacccctc acagttacct cagaagccct aactgtggct gccgccgcac ctctaatggt | 6420 |
| cgcgggcaac acactcacca tgcaatcaca ggccccgcta accgtgcacg actccaaact | 6480 |
| tagcattgcc acccaaggac ccctcacagt gtcagaagga aagctagccc tgcaaacatc | 6540 |
| aggcccctc accaccaccg atagcagtac ccttactatc actgcctcac cccctctaac | 6600 |
| tactgccact ggtagcttgg gcattgactt gaaagagccc atttatacac aaaatgaaa | 6660 |
| actaggacta aagtacgggg ctcctttgca tgtaacagac gacctaaaca ctttgaccgt | 6720 |
| agcaactggt ccaggtgtga ctattaataa tacttccttg caaactaaag ttactggagc | 6780 |
| cttgggtttt gattcacaag gcaatatgca acttaatgta gcaggaggac taaggattga | 6840 |
| ttctcaaaac agacgcctta tacttgatgt tagttatccg tttgatgctc aaaaccaact | 6900 |
| aaatctaaga ctaggacagg ccctctcttt tataaactca gcccacaact tggatattaa | 6960 |
| ctacaacaaa ggcctttact tgtttacagc ttcaaacaat tccaaaaagc ttgaggttaa | 7020 |
| cctaagcact gccaagggggt tgatgtttga cgctacagcc atagccatta atgcaggaga | 7080 |
| tgggcttgaa tttggttcac ctaatgcacc aaacacaaat cccctcaaaa caaaaattgg | 7140 |
| ccatggccta gaatttgatt caaacaaggc tatggttcct aaaactaggaa ctggccttag | 7200 |
| ttttgacagc acaggtgcca ttacagtagg aaacaaaaat aatgataagc taaccccta | 7258 |

<210> SEQ ID NO 5
<211> LENGTH: 3712
<212> TYPE: DNA
<213> ORGANISM: adenovirus

<400> SEQUENCE: 5

| | |
|---|---|
| tggacaggtc caaaaccaga agccaactgc ataattgaat acgggaaaca aaacccagat | 60 |
| agcaaactaa ctttaatcct tgtaaaaaat ggaggaattg ttaatggata tgtaacgcta | 120 |
| atgggagcct cagactacgt taacacctta tttaaaaaca aaaatgtctc cattaatgta | 180 |
| gaactatact ttgatgccac tggtcatata ttaccagact catcttctct taaaacagat | 240 |
| ctagaactaa aatacaagca aaccgctgac tttagtgcaa gaggttttat gccaagtact | 300 |
| acagcgtatc catttgtcct tcctaatgcg ggaacacata atgaaaatta tattttggt | 360 |
| caatgctact acaaagcaag cgatggtgcc ctttttccgt tggaagttac tgttatgctt | 420 |
| aataaacgcc tgccagatag tcgcacatcc tatgttatga ctttttttatg gtccttgaat | 480 |
| gctggtctag ctccagaaac tactcaggca accctcataa cctcccccatt tacctttttcc | 540 |

```
tatattagag aagatgactg aagaatcgtt tgtgttatgt ttcaacgtgt ttattttca    600 attgcagaaa atttcaagtc atttttcatt cagtagtata gccccaccac cacatagctt    660
atacagatca ccgtacctta atcaaactca cagaaccta gtattcaacc tgccacctcc    720
ctcccaacac acagagtaca cagtcctttc tccccggctg ccttaaaaa gcatcatatc    780 atgggtaaca gacatattct taggtgttat attccacacg gtttcctgtc gagccaaacg    840
ctcatcagtg atattaataa actccccggg cagctcactt aagttcatgt cgctgtccag    900
ctgctgagcc acaggctgct gtccaacttg cggttgctta acgggcggcg aaggagaagt    960
ccacgcctac atgggggtag agtcataatc gtgcatcagg ataggcggt ggtgctgcag    1020 cagcgcgcga ataaactgct gccgccgccg ctccgtcctg caggaataca acatggcagt    1080
ggtctcctca gcgatgattc gcaccgcccg cagcataagg cgccttgtcc tccgggcaca    1140
gcagcgcacc ctgatctcac ttaaatcagc acagtaactg cagcacagca ccacaatatt    1200
gttcaaaatc ccacagtgca aggcgctgta tccaaagctc atggcgggga ccacagaacc    1260
cacgtggcca tcataccaca agcgcaggta gattaagtgg cgacccctca taaacacgct    1320
ggacataaac attacctctt ttggcatgtt gtaattcacc acctcccggt accatataaa    1380
cctctgatta aacatggcgc catccaccac catcctaaac cagctggcca aaacctgccc    1440
gccggctata cactgcaggg aaccgggact ggaacaatga cagtggagag cccaggactc    1500
gtaaccatgg atcatcatgc tcgtcatgat atcaatgttg gcacaacaca ggcacacgtg    1560
catacacttc ctcaggatta caagctcctc ccgcgttaga accatatccc agggaacaac    1620
ccattcctga atcagcgtaa atcccacact gcagggaaga cctcgcacgt aactcacgtt    1680
gtgcattgtc aaagtgttac attcgggcag cagcggatga tcctccagta tggtagcgcg    1740
ggtttctgtc tcaaaaggag gtagacgatc cctactgtac ggagtgcgcc gagacaaccg    1800
agatcgtgtt ggtcgtagtg tcatgccaaa tggaacgccg gacgtagtca tatttcctga    1860
agcaaaacca ggtgcgggcg tgacaaacag atctgcgtct ccggtctcgc cgcttagatc    1920
gctctgtgta gtagttgtag tatatccact ctctcaaagc atccaggcgc ccctggctt    1980 cgggttctat gtaaactcct tcatgcgccg ctgccctgat aacatccacc accgcagaat    2040
aagccacacc cagccaacct acacattcgt tctgcgagtc acacacggga ggagcgggaa    2100
gagctggaag aaccatgttt tttttttat tccaaagat tatccaaaac ctcaaaatga    2160
agatctatta agtgaacgcg ctcccctccg gtggcgtggt caaactctac agccaaagaa    2220
cagataatgg catttgtaag atgttgcaca atggcttcca aaaggcaaac ggccctcacg    2280
tccaagtgga cgtaaaggct aaaccttca gggtgaatct cctctataaa cattccagca    2340
ccttcaacca tgcccaaata attctcatct cgccaccttc tcaatatatc tctaagcaaa    2400
tcccgaatat aagtccggc cattgtaaaa atctgctcca gagcgccctc caccttcagc    2460
ctcaagcagc gaatcatgat tgcaaaaatt caggttcctc acagacctgt ataagattca    2520
aaagcggaac attaacaaaa ataccgcgat cccgtaggtc ccttcgcagg gccagctgaa    2580
cataatcgtg caggtctgca cggaccagcg cggccacttc cccgccagga accatgacaa    2640
aagaacccac actgattatg acacgcatac tcggagctat gctaaccagc gtagcccga    2700 tgtaagcttg ttgcatgggc ggcgatataa aatgcaaggt gctgctcaaa aaatcaggca    2760
aagcctcgcg caaaaagaa agcacatcgt agtcatgctc atgcagataa aggcaggtaa    2820
gctccggaac caccacagaa aaagacacca ttttctctc aaacatgtct gcgggtttct    2880
```

```
gcataaacac aaaataaaat aacaaaaaaa catttaaaca ttagaagcct gtcttacaac      2940
aggaaaaaca acccttataa gcataagacg gactacggcc atgccggcgt gaccgtaaaa      3000
aaactggtca ccgtgattaa aaagcaccac cgacagctcc tcggtcatgt ccggagtcat      3060
aatgtaagac tcggtaaaca catcaggttg attcacatcg gtcagtgcta aaaagcgacc      3120
gaaatagccc gggggaatac atacccgcag gcgtagagac aacattacag ccccccatagg     3180 aggtataaca aaattaatag gagagaaaaa cacataaaca cctgaaaaac cctcctgcct      3240
aggcaaaata gcaccctccc gctccagaac aacatacagc gcttccacag cggcagccat      3300
aacagtcagc cttaccagta aaaagaaaa  cctattaaaa aaacaccact cgacacggca      3360
ccagctcaat cagtcacagt gtaaaaaagg gccaagtgca gagcgagtat atataggact     3420
aaaaaatgac gtaacggtta aagtccacaa aaaacaccca gaaaaccgca cgcgaaccta     3480
cgcccagaaa cgaaagccaa aaaacccaca acttcctcaa atcgtcactt ccgttttccc     3540
acgttacgtc acttcccatt ttaagaaaac tacaattccc aacacataca agttactccg     3600
ccctaaaacc tacgtcaccc gccccgttcc cacgccccgc gccacgtcac aaactccacc     3660
ccctcattat catattggct tcaatccaaa ataaggtata ttattgatga tg             3712

<210> SEQ ID NO 6
<211> LENGTH: 3880
<212> TYPE: DNA
<213> ORGANISM: adenovirus

<400> SEQUENCE: 6
gcccctctcc ctcccccccc cctaacgtta ctggccgaag ccgcttggaa taaggccggt       60
gtgcgtttgt ctatatgtta ttttccacca tattgccgtc ttttggcaat gtgagggccc      120
ggaaacctgg ccctgtcttc ttgacgagca ttcctagggg tctttcccct ctcgccaaag      180
gaatgcaagg tctgttgaat gtcgtgaagg aagcagttcc tctggaagct tcttgaagac      240
aaacaacgtc tgtagcgacc ctttgcaggc agcggaaccc cccacctggc gacaggtgcc      300
tctgcggcca aaagccacgt gtataagata cacctgcaaa ggcggcacaa ccccagtgcc      360
acgttgtgag ttggatagtt gtggaaagag tcaaatggct ctcctcaagc gtattcaaca      420
aggggctgaa ggatgcccag aaggtacccc attgtatggg atctgatctg ggcctcggt      480 gcacatgctt tacatgtgtt tagtcgaggt taaaaaaacg tctaggcccc ccgaaccacg      540
gggacgtggt tttcctttga aaaacacgat gataatatgg ccacaaccat gtacaggatg      600
caactcctgt cttgcattgc actaagtctt gcacttgtca caaacagtgc acctacttca      660
agttctacaa agaaaacaca gctacaactg gagcatttac tgctggattt acagatgatt      720
ttgaatggaa ttaataatta caagaatccc aaactcacca ggatgctcac atttaagttt      780
tacatgccca agaaggccac agaactgaaa catcttcagt gtctagaaga gaactcaaa      840 cctctggagg aagtgctaaa tttagctcaa agcaaaaact ttcacttaag acccagggac      900
ttaatcagca atatcaacgt aatagttctg gaactaaagg gatctgaaac aacattcatg      960
tgtgaatatg ctgatgagac agcaaccatt gtagaatttc tgaacagatg gattaccttt     1020
tgtcaaagca tcatctcaac actgacttga gtcagcatct gactttggcc agcacctgtc     1080
ccgcggattt gttccagtcc aactacagcg acccacccta acagagatga ccaacacaac     1140
caacgcggcc gccgctaccg gacttacatc taccacaaat acacccccaag tttctgcctt     1200 tgtcaataac tgggataact tgggcatgtg gtggttctcc atagcgctta tgtttgtatg     1260
ccttattatt atgtggctca tctgctgcct aaagcgcaaa cgcgcccgac cacccatcta     1320
```

```
tagtcccatc attgtgctac acccaaacaa tgatggaatc catagattgg acggactgaa    1380
acacatgttc ttttctctta cagtatgatt aaatgagaca tgattcctcg agtttttata    1440
ttactgaccc ttgttgcgct tttttgtgcg tgctccacat tggctgcggt ttctcacatc    1500
gaagtagact gcattccagc cttcacagtc tatttgcttt acggatttgt caccctcacg    1560
ctcatctgca gcctcatcac tgtggtcatc gcctttatcc agtgcattga ctgggtctgt    1620
gtgcgctttg catatctcag acaccatccc cagtacaggg acaggactat agctgagctt    1680
cttagaattc tttaattatg aaatttactg tgacttttct gctgattatt gcaccctat    1740 ctgcgttttg ttccccgacc tccaagcctc aaagacatat atcatgcaga ttcactcgta    1800
tatggaatat tccaagttgc tacaatgaaa aaagcgatct ttccgaagcc tggttatatg    1860
caatcatctc tgttatggtg ttctgcagta ccatcttagc cctagctata tatccctacc    1920
ttgacattgg ctggaaacga atagatgcca tgaaccaccc aactttcccc gcgcccgcta    1980
tgcttccact gcaacaagtt gttgccggcg ctttgtccc agccaatcag cctcgcccca    2040
cttctcccac ccccactgaa atcagctact ttaatctaac aggaggagat gactgacacc    2100
ctagatctag aaatggacgg aattattaca gagcagcgcc tgctagaaag acgcagggca    2160
gcggccgagc aacagcgcat gaatcaagag ctccaagaca tggttaactt gcaccagtgc    2220
aaaaggggta tcttttgtct ggtaaagcag gccaaagtca cctacgacag taataccacc    2280
ggacaccgcc ttagctacaa gttgccaacc aagcgtcaga aattggtggt catggtggga    2340
gaaaagccca ttaccataac tcagcactcg gtagaaaccg aaggctgcat tcactcacct    2400
tgtcaaggac ctgaggatct ctgcacccTT attaagaccc tgtgcggtct caaagatctt    2460
attccctttA actaataaaa aaaataata aagcatcact tacttaaaat cagttagcaa    2520
atttctgtcc agtttattca gcagcacctc cttgccctcc tcccagctct ggtattgcag    2580
cttcctcctg gctgcaaact ttctccacaa tctaaatgga atgtcagttt cctcctgttc    2640
ctgtccatcc gcacccacta tcttcatgtt gttgcagatg aagcgcgcaa gaccgtctga    2700
agataccttc aaccccgtgt atccatatga cacggaaacc ggtcctccaa ctgtgccttt    2760
tcttactcct ccctttgtat cccccaatgg gtttcaagag agtcccCCTG gggtactctc    2820
tttgcgccta tccgaacctc tagttacctc caatggcatg cttgcgctca aaatgggcaa    2880
cggcctctct ctggacgagg ccggcaacct tacctcccaa aatgtaacca ctgtgagccc    2940
acctctcaaa aaaccaagt caaacataaa cctggaaata tctgcacccc tcacagttac    3000
ctcagaagcc ctaactgtgg ctgccgccgc acctctaatg tcgcgggca acacactcac    3060 catgcaatca caggccccgc taaccgtgca cgactccaaa cttagcattg ccacccaagg    3120 accccctcaca gtgtcagaag gaaagctagc cctgcaaaca tcaggccccc tcaccaccac    3180
cgatagcagt acccttacta tcactgcctc accccctcta actactgcca ctggtagctt    3240
gggcattgac ttgaaagagc ccattttatac acaaaatgga aaactaggac taaagtacgg    3300
ggctcctttg catgtaacag acgacctaaa cactttgacc gtagcaactg gtccaggtgt    3360
gactattaat aatacttcct tgcaaactaa agttactgga gccttgggtt ttgattcaca    3420
aggcaatatg caacttaatg tagcaggagg actaaggatt gattctcaaa acagacgcct    3480
tatacttgat gttagttatc cgtttgatgc tcaaaaccaa ctaaatctaa gactaggaca    3540 gggcccctctt tttataaact cagcccacaa cttggatatt aactacaaca aaggccttta    3600
cttgtttaca gcttcaaaca attccaaaaa gcttgaggtt aacctaagca ctgccaaggg    3660
```

<210> SEQ ID NO 7
<211> LENGTH: 4120
<212> TYPE: DNA
<213> ORGANISM: adenovirus

<400> SEQUENCE: 7

```
gttgatgttt gacgctacag ccatagccat taatgcagga gatgggcttg aatttggttc    3720
acctaatgca ccaaacacaa atcccctcaa aacaaaaatt ggccatggcc tagaatttga    3780
ttcaaacaag gctatggttc ctaaactagg aactggcctt agttttgaca gcacaggtgc    3840
cattacagta ggaaacaaaa ataatgataa gctaacccta                          3880
gcccctctcc ctccccccc cctaacgtta ctggccgaag ccgcttggaa taaggccggt       60
gtgcgtttgt ctatatgtta ttttccacca tattgccgtc ttttggcaat gtgagggccc     120
ggaaacctgg ccctgtcttc ttgacgagca ttcctagggg tctttcccct ctcgccaaag     180
gaatgcaagg tctgttgaat gtcgtgaagg aagcagttcc tctggaagct tcttgaagac     240
aaacaacgtc tgtagcgacc ctttgcaggc agcggaaccc cccacctggc gacaggtgcc     300
tctgcggcca aaagccacgt gtataagata cacctgcaaa ggcggcacaa ccccagtgcc     360
acgttgtgag ttggatagtt gtggaaagag tcaaatggct ctcctcaagc gtattcaaca     420
aggggctgaa ggatgcccag aaggtacccc attgtatggg atctgatctg ggcctcggt      480 gcacatgctt tacatgtgtt tagtcgaggt taaaaaacg tctaggcccc cgaaccacg       540 gggacgtggt tttcctttga aaaacacgat gataatatgg ccacaaccat gagcactgaa     600
agcatgatcc gggacgtgga gctggccgag gaggcgctcc caagaagac aggggggccc      660 cagggctcca ggcggtgctt gttcctcagc ctcttctcct tcctgatcgt ggcaggcgcc     720
accacgctct tctgcctgct gcactttgga gtgatcggcc cccagaggga gagttcccc      780 agggacctct ctctaatcag ccctctggcc caggcagtca gatcatcttc tcgaaccccg     840
agtgacaagc ctgtagccca tgttgtagca aaccctcaag ctgaggggca gctccagtgg     900
ctgaaccgcc gggccaatgc cctcctggcc aatggcgtgg agctgagaga taaccagctg     960
gtggtgccat cagagggcct gtacctcatc tactcccagg tcctcttcaa gggccaaggc    1020 tgccccttcca cccatgtgct cctcacccac accatcagcc gcatcgccgt ctcctaccag    1080
accaaggtca acctcctctc tgccatcaag agccctgcc agaggagac cccagagggg       1140 gctgaggcca agccctggta tgagcccatc tatctgggag gggtcttcca gctggagaag    1200
ggtgaccgac tcagcgctga gatcaatcgg cccgactatc tcgactttgc cgagtctggg    1260
caggtctact ttgggatcat tgccctgtga gtcagcatct gactttggcc agcacctgtc    1320
ccgcggattt gttccagtcc aactacagcg acccacccta acagagatga ccaacacaac    1380
caacgcggcc gccgctaccg gacttacatc taccacaaat acaccccaag tttctgcctt    1440
tgtcaataac tgggataact tgggcatgtg gtggttctcc atagcgctta tgtttgtatg    1500
ccttattatt atgtggctca tctgctgcct aaagcgcaaa cgcgcccgac cacccatcta    1560
tagtcccatc attgtgctac acccaaacaa tgatggaatc catagattgg acggactgaa    1620
acacatgttc ttttctctta cagtatgatt aaatgagaca tgattcctcg agtttttata    1680
ttactgaccc ttgttgcgct ttttttgtgcg tgctccacat tggctgcggt ttctcacatc    1740
gaagtagact gcattccagc cttcacagtc tatttgcttt acggatttgt cacctctcacg   1800 ctcatctgca gcctcatcac tgtggtcatc gcctttatcc agtgcattga ctgggtctgt    1860
gtgcgctttg catatctcag acaccatccc cagtacaggg acaggactat agctgagctt    1920
```

```
cttagaattc tttaattatg aaatttactg tgacttttct gctgattatt tgcaccctat   1980
ctgcgttttg ttccccgacc tccaagcctc aaagacatat atcatgcaga ttcactcgta   2040
tatggaatat tccaagttgc tacaatgaaa aaagcgatct ttccgaagcc tggttatatg   2100
caatcatctc tgttatggtg ttctgcagta ccatcttagc cctagctata tatccctacc   2160
ttgacattgg ctggaaacga atagatgcca tgaaccaccc aactttcccc gcgcccgcta   2220
tgcttccact gcaacaagtt gttgccggcg ctttgtccc agccaatcag cctcgcccca    2280
cttctcccac ccccactgaa atcagctact ttaatctaac aggaggagat gactgacacc   2340
ctagatctag aaatggacgg aattattaca gagcagcgcc tgctagaaag acgcagggca   2400
gcggccgagc aacagcgcat gaatcaagag ctccaagaca tggttaactt gcaccagtgc   2460 aaaagggta tcttttgtct ggtaaagcag gccaaagtca cctacgacag taataccacc     2520
ggacaccgcc ttagctacaa gttgccaacc aagcgtcaga aattggtggt catggtggga   2580
gaaaagccca ttaccataac tcagcactcg gtagaaaccg aaggctgcat tcactcacct   2640
tgtcaaggac ctgaggatct ctgcacccct attaagaccc tgtgcggtct caaagatctt   2700 attccccttta actaataaaa aaaaataata aagcatcact tacttaaaat cagttagcaa    2760
atttctgtcc agtttattca gcagcacctc cttgccctcc tcccagctct ggtattgcag   2820
cttcctcctg gctgcaaact ttctccacaa tctaaatgga atgtcagttt cctcctgttc   2880
ctgtccatcc gcacccacta tcttcatgtt gttgcagatg aagcgcgcaa gaccgtctga   2940
agataccttc aaccccgtgt atccatatga cacggaaacc ggtcctccaa ctgtgccttt   3000
tcttactcct ccctttgtat cccccaatgg gtttcaagag agtcccctg gggtactctc     3060 tttgcgccta tccgaacctc tagttacctc caatggcatg cttgcgctca aaatgggcaa   3120
cggcctctct ctggacgagg ccggcaacct tacctcccaa aatgtaacca ctgtgagccc   3180
acctctcaaa aaaaccaagt caaacataaa cctggaaata tctgcacccc tcacagttac   3240
ctcagaagcc ctaactgtgg ctgccgccgc acctctaatg gtcgcgggca acacactcac   3300
catgcaatca caggcccgc taaccgtgca cgactccaaa cttagcattg ccacccaagg    3360 accccctcaca gtgtcagaag gaaagctagc cctgcaaaca tcaggccccc tcaccaccac   3420
cgatagcagt accttacta tcactgcctc accccctcta actactgcca ctggtagctt     3480
gggcattgac ttgaaagagc ccatttatac acaaaatgaa aaactaggac taaagtacgg   3540
ggctcctttg catgtaacag acgacctaaa cactttgacc gtagcaactg gtccaggtgt   3600
gactattaat aatacttcct tgcaaaactaa agttactgga gccttgggtt ttgattcaca   3660
aggcaatatg caacttaatg tagcaggagg actaaggatt gattctcaaa acagacgcct   3720
tatacttgat gttagttatc cgtttgatgc tcaaaaccaa ctaaatctaa gactaggaca   3780
gggccctctt tttataaact cagcccacaa cttggatatt aactacaaca aaggcccttta   3840 cttgtttaca gcttcaaaca attccaaaaa gcttgaggtt aacctaagca ctgccaaggg   3900
gttgatgttt gacgctacag ccatagccat taatgcagga gatgggcttg aatttggttc   3960
acctaatgca ccaaacacaa atcccctcaa aacaaaaatt ggccatggcc tagaatttga   4020
ttcaaacaag gctatggttc ctaaactagg aactggcctt agttttgaca gcacaggtgc   4080
cattacagta ggaaacaaaa ataatgataa gctaaccta                          4120
```

`<210>` SEQ ID NO 8
`<211>` LENGTH: 4954
`<212>` TYPE: DNA

<213> ORGANISM: adenovirus

<400> SEQUENCE: 8

```
atggactgga tctggagaat cttattcctt gtcggggctg ctaccggcgc acatatggcc      60
caggtccagc ttgttcaatc tggagctgaa gttaagagac cgggcgctag tgtgcaagta     120
tcctgccgag ccagcggata ctcgattaac acgtattaca tgcagtgggt tagacaggct     180
ccggggggcgg gactagaatg gatgggtgta ataaatccct caggggttac tagttacgcc     240
caaaagtttc aaggacgtgt cacgctgact aacgacacga gcactaacac cgtgtatatg     300
cagctgaaca gtttgacgag cgccgacaca gcagtttatt attgtgctcg ttgggcgctg     360
tgggggact tcggaatgga tgtgtgggc aaaggtactt tggtgaccgt tagcagcggg     420
ggaggaggtt ctggaggcgg cggatctggt ggagggggt ccgacatcca aatgacacag     480
tctccgagta ccttgagtgc gtcaatcgga gatcgcgtca ccatcacgtg cagagcaagc     540
gagggcatat accactggct cgcatggtat caacaaaagc ctgggaaagc gccaaagctc     600
cttatataca aggcctcctc gctggcgtct ggggcgccca gtagatttttc cggtagtgga     660
tccggtactg attttacgct taccatcagc agcttacagc cagacgattt cgctacttac     720
tattgtcagc agtactccaa ctacccactc acattcggag gaggtactaa gcttgaaatt     780
aaacgccagg tgcaactcca gaatcgggt ggagggcttg tccagccagg cggctcaatg     840
aaactttcct gtgttgctag cggtttcact ttttcgaatt actggatgaa ctgggtgcgc     900
cagtcgcctg aaaagggttt agaatgggtc gccgagatac ggctaaaaag taacaattat     960
gcgacacact acgcagaatc ggtcaaaggc cggtttacta tatcaaggga cgactctaaa    1020
agctcggtat acttacaaat gaacaactta cgtgcagagg atacaggcat ttattactgt    1080
acaggcgtcg gattcgcgta ctggggccag gggaccaccg taactgtcag cggaggaggt    1140
ggttctggag ggggggtag tggtggtggt ggttcagaca tcgtcgtcac ccaagaatcc    1200
gcactcacga ccagtccagg agaaaccgtt actctcactt gtagatcgtc tactggcgcg    1260
gtgacgacgt cgaattatgc gaactgggtt caggagaagc cggatcacct tttcacaggg    1320
ttaataggag gtacgaataa ccgtgccccc ggggttcccg cgagattcag cggatcattg    1380
ataggcgata aggctgcctt gacaatcacg ggagcccaga ctgaggacga agcaatatac    1440
ttctgcgcgt tgtggtacag caaccattgg gtgtttggag ggggaacgaa actgaccgta    1500
ctaggttccg agggtggcgg tggctctgac atcaaactgt ccggggctga gctagctaga    1560
ccaggtgcat ctgtcaagat gtcgtgtaaa acgagcggat acaccttcac ccgatataca    1620
atgcattggg taaacagag acccggtcag ggtctagagt ggataggcta cataaacccg    1680
tccagagggt acacaaatta taatcagaag ttcaaagaca agcgactct gacaacagat    1740
aaatcgagct ccaccgcgta tatgcagttg agtagcttaa catcggagga ctctgcagtc    1800
tactattgcg caagatacta cgacgatcat tactgtctgg actactgggg aggtaccacc    1860
ctgactgtct caagtggtgg cggggggtcg ggaggcggcg gttctggggg gggggttct    1920
gacatcctta cttctcctgc tattatgtct gcctctccag gcgaaaaggt tactatgacg    1980
tgtagggcgt caagtagtgt tagttacatg aattggtatc aacaaaaatc aggcacatct    2040
cccaagcgct ggatttatga cacctcgaaa gtcgcgtccg gcgtcccgta tcggttctct    2100
ggcagcgggt cgggtactag ttacgtcagc atctgacttt ggccagcacc tgtcccgcgg    2160
atttgttcca gtccaactac agcgaccac cctaacagag atgaccaaca caaccaacgc    2220
ggccgccgct accggactta catctaccac aaatacaccc caagtttctg cctttgtcaa    2280
```

-continued

```
taactgggat aacttgggca tgtggtggtt ctccatagcg cttatgtttg tatgccttat    2340
tattatgtgg ctcatctgct gcctaaagcg caaacgcgcc cgaccaccca tctatagtcc    2400
catcattgtg ctacacccaa acaatgatgg aatccataga ttggacggac tgaaacacat    2460
gttcttttct cttacagtat gattaaatga gacatgattc ctcgagtttt tatattactg    2520
acccttgttg cgcttttttg tgcgtgctcc acattggctg cggtttctca catcgaagta    2580
gactgcattc cagccttcac agtctatttg ctttacggat ttgtcaccct cacgctcatc    2640
tgcagcctca tcactgtggt catcgccttt atccagtgca ttgactgggt ctgtgtgcgc    2700
tttgcatatc tcagacacca tccccagtac agggacagga ctatagctga gcttcttaga    2760
attctttaat tatgaaattt actgtgactt ttctgctgat tatttgcacc ctatctgcgt    2820
tttgttcccc gacctccaag cctcaaagac atatatcatg cagattcact cgtatatgga    2880
atattccaag ttgctacaat gaaaaagcg atctttccga agcctggtta tatgcaatca    2940
tctctgttat ggtgttctgc agtaccatct tagccctagc tatatatccc taccttgaca    3000
ttggctggaa acgaatagat gccatgaacc acccaacttt ccccgcgccc gctatgcttc    3060
cactgcaaca agttgttgcc ggcggctttg tcccagccaa tcagcctcgc cccacttctc    3120
ccacccccac tgaaatcagc tactttaatc taacaggagg agatgactga caccctagat    3180
ctagaaatgg acgaattat tacagagcag cgcctgctag aaagacgcag ggcagcggcc    3240
gagcaacagc gcatgaatca agagctccaa gacatggtta acttgcacca gtgcaaaagg    3300
ggtatctttt gtctggtaaa gcaggccaaa gtcacctacg acagtaatac caccggacac    3360
cgccttagct acaagttgcc aaccaagcgt cagaaattgg tggtcatggt gggagaaaag    3420
cccattacca taactcagca ctcggtagaa accgaaggct gcattcactc accttgtcaa    3480
ggacctgagg atctctgcac ccttattaag accctgtgcg gtctcaaaga tcttattccc    3540
tttaactaat aaaaaaaaat aataaagcat cacttactta aaatcagtta gcaaatttct    3600
gtccagttta ttcagcagca cctccttgcc ctcctcccag ctctggtatt gcagcttcct    3660
cctggctgca aactttctcc acaatctaaa tggaatgtca gtttcctcct gttcctgtcc    3720
atccgcaccc actatcttca tgttgttgca gatgaagcgc gcaagaccgt ctgaagatac    3780
cttcaacccc gtgtatccat atgacacgga aaccggtcct ccaactgtgc cttttcttac    3840
tcctcccttt gtatccccca atgggtttca agagagtccc cctggggtac tctctttgcg    3900
cctatccgaa cctctagtta cctccaatgg catgcttgcg ctcaaaatgg caacggcct    3960 ctctctggac gaggccggca accttacctc ccaaaatgta accactgtga gcccacctct    4020
caaaaaaacc aagtcaaaca taaacctgga aatatctgca cccctcacag ttacctcaga    4080
agccctaact gtggctgccg ccgcacctct aatggtcgcg ggcaacacac tcaccatgca    4140
atcacaggcc ccgctaaccg tgcacgactc caaacttagc attgccaccc aaggacccct    4200
cacagtgtca gaaggaaagc tagccctgca aacatcaggc cccctcacca ccaccgatag    4260
cagtaccctt actatcactg cctcaccccc tctaactact gccactggta gcttgggcat    4320
tgacttgaaa gagcccattt atacacaaaa tggaaaacta ggactaaagt acggggctcc    4380
tttgcatgta acagacgacc taaacacttt gaccgtagca actggtccag gtgtgactat    4440
taataatact tccttgcaaa ctaaagttac tggagccttg gttttgatt cacaaggcaa    4500 tatgcaactt aatgtagcag gaggactaag gattgattct caaacagac gccttatact    4560 tgatgttagt tatccgtttg atgctcaaaa ccaactaaat ctaagactag gacagggccc    4620
```

| | |
|---|---|
| tctttttata aactcagccc acaacttgga tattaactac aacaaaggcc tttacttgtt | 4680 |
| tacagcttca acaattcca aaaagcttga ggttaaccta agcactgcca aggggttgat | 4740 |
| gtttgacgct acagccatag ccattaatgc aggagatggg cttgaatttg gttcacctaa | 4800 |
| tgcaccaaac acaaatcccc tcaaaacaaa aattggccat ggcctagaat ttgattcaaa | 4860 |
| caaggctatg gttcctaaac taggaactgg ccttagtttt gacagcacag gtgccattac | 4920 |
| agtaggaaac aaaaataatg ataagctaac ccta | 4954 |

```
<210> SEQ ID NO 9
<211> LENGTH: 4945
<212> TYPE: DNA
<213> ORGANISM: adenovirus

<400> SEQUENCE: 9
```

| | |
|---|---|
| atggactgga tctggagaat cttattcctt gtcggggctg ctaccggcgc acatatggcc | 60 |
| caggtccagc ttgttcaatc tggagctgaa gttaagagac cgggcgctag tgtgcaagta | 120 |
| tcctgccgag ccagcggata ctcgattaac acgtattaca tgcagtgggt tagacaggct | 180 |
| ccggggggcgg gactagaatg gatgggtgta ataaatccct caggggttac tagttacgcc | 240 |
| caaaagtttc aaggacgtgt cacgctgact aacgacacga gcactaacac cgtgtatatg | 300 |
| cagctgaaca gtttgacgag cgccgacaca gcagtttatt attgtgctcg ttgggcgctg | 360 |
| tggggggact tcggaatgga tgtgtggggc aaaggtactt tggtgaccgt tagcagcggg | 420 |
| ggaggaggtt ctggaggcgg cggatctggt ggagggggggt ccgacatcca aatgacacag | 480 |
| tctccgagta ccttgagtgc gtcaatcgga gatcgcgtca ccatcacgtg cagagcaagc | 540 |
| gagggcatat accactggct cgcatggtat caacaaaagc ctgggaaagc gccaaagctc | 600 |
| cttatataca aggcctcctc gctggcgtct ggggcgccca gtagattttc cggtagtgga | 660 |
| tccggtactg attttacgct taccatcagc agcttacagc cagacgattt cgctacttac | 720 |
| tattgtcagc agtactccaa ctacccactc acattcggag gaggtactaa gcttgaaatt | 780 |
| aaacgccaag tacaactaca ggagagcggg cctggtctcg tcaaaccttc ccagacccta | 840 |
| agcttgactt gtactgtatc tggcggtagc ataaacaaca ataattacta ctggacctgg | 900 |
| atccgacagc atccaggcaa agggctagag tggatagggt acatatatta ttctggctcc | 960 |
| acgttttaca accttctct taagagcaga gtaacaattt cggtggacac gtctaagaca | 1020 |
| cagttttccc tcaaattgag ttccgttact gccgctgata ctgcggtata ttattgtgct | 1080 |
| agggaagaca ctatgaccgg tcttgatgtg tggggtcaag gcacggttac agtctcaagt | 1140 |
| ggaggaggtg gttctggagg ggggggtagt ggtggtggtg gttcagatat acaaatgact | 1200 |
| cagtctccat cttcactttc agcatccgtg ggggataggg tgactatcac atgcagagcg | 1260 |
| tcacagtcaa tcaacaatta cctcaattgg taccaacaaa aacctggaaa ggcacccact | 1320 |
| cttttgattt atgctgccag tagtttgcaa tcgggagttc cttccaggtt tagtggctca | 1380 |
| agatctggaa ctgatttcac attgactata tcaagtttgc agcctgaaga cttcgctgct | 1440 |
| tatttctgcc aacagactta tagcaacccc accttcggac agggaactaa ggtcgaagtg | 1500 |
| aaaggtggcg gtggctctga catcaaactg tccggggctg agctagctag accaggtgca | 1560 |
| tctgtcaaga tgtcgtgtaa aacgagcgga tacaccttca cccgatatac aatgcattgg | 1620 |
| gtaaaacaga gacccggtca gggtctagag tggataggct acataaaccc gtccagaggg | 1680 |
| tacacaaatt ataatcagaa gttcaaagac aaagcgactc tgacaacaga taatcgagc | 1740 |
| tccaccgcgt atatgcagtt gagtagctta acatcggagg actctgcagt ctactattgc | 1800 |

```
gcaagatact acgacgatca ttactgtctg gactactggg gaggtaccac cctgactgtc    1860
tcaagtggtg gcggggggtc gggaggcggc ggttctgggg gggggggttc tgacatcctt    1920
acttctcctg ctattatgtc tgcctctcca ggcgaaaagg ttactatgac gtgtagggcg    1980
tcaagtagtg ttagttacat gaattggtat caacaaaaat caggcacatc tcccaagcgc    2040
tggatttatg acacctcgaa agtcgcgtcc ggcgtcccgt atcggttctc tggcagcggg    2100
tcgggtacta gttacgtcag catctgactt tggccagcac ctgtcccgcg gatttgttcc    2160
agtccaacta cagcgaccca ccctaacaga gatgaccaac acaaccaacg cggccgccgc    2220
taccggactt acatctacca caaatacacc ccaagtttct gcctttgtca ataactggga    2280
taacttgggc atgtggtggt tctccatagc gcttatgttt gtatgcctta ttattatgtg    2340
gctcatctgc tgcctaaagc gcaaacgcgc ccgaccaccc atctatagtc ccatcattgt    2400
gctacaccca acaatgatg gaatccatag attggacgga ctgaaacaca tgttctttttc    2460 tcttacagta tgattaaatg agacatgatt cctcgagttt ttatattact gacccttgtt    2520 gcgcttttt gtgcgtgctc cacattggct gcggtttctc acatcgaagt agactgcatt    2580
ccagccttca cagtctattt gctttacgga tttgtcaccc tcacgctcat ctgcagcctc    2640
atcactgtgg tcatcgcctt tatccagtgc attgactggg tctgtgtgcg ctttgcatat    2700
ctcagacacc atccccagta cagggacagg actatagctg agcttcttag aattctttaa    2760
ttatgaaatt tactgtgact tttctgctga ttatttgcac cctatctgcg ttttgttccc    2820
cgacctccaa gcctcaaaga catatatcat gcagattcac tcgtatatgg aatattccaa    2880
gttgctacaa tgaaaaaagc gatctttccg aagcctggtt atatgcaatc atctctgtta    2940
tggtgttctg cagtaccatc ttagccctag ctatatatcc ctaccttgac attggctgga    3000
aacgaataga tgccatgaac cacccaactt tccccgcgcc cgctatgctt ccactgcaac    3060
aagttgttgc cggcggcttt gtcccagcca atcagcctcg ccccacttct cccacccca    3120 ctgaaatcag ctactttaat ctaacaggag gagatgactg acaccctaga tctagaaatg    3180
gacggaatta ttacagagca gcgcctgcta gaaagacgca gggcagcggc cgagcaacag    3240
cgcatgaatc aagagctcca agacatggtt aacttgcacc agtgcaaaag gggtatcttt    3300
tgtctggtaa agcaggccaa agtcacctac gacagtaata ccaccggaca ccgccttagc    3360
tacaagttgc caaccaagcg tcagaaattg gtggtcatgg tgggagaaaa gcccattacc    3420
ataactcagc actcggtaga aaccgaaggc tgcattcact caccttgtca aggacctgag    3480
gatctctgca cccttattaa gaccctgtgc ggtctcaaag atcttattcc ctttaactaa    3540
taaaaaaaaa taataaagca tcacttactt aaaatcagtt agcaaatttc tgtccagttt    3600
attcagcagc acctccttgc cctcctccca gctctggtat tgcagcttcc tcctggctgc    3660
aaactttctc cacaatctaa atggaatgtc agtttcctcc tgttcctgtc catccgcacc    3720
cactatcttc atgttgttgc agatgaagcg cgcaagaccg tctgaagata ccttcaaccc    3780
cgtgtatcca tatgacacgg aaaccggtcc tccaactgtg ccttttctta ctcctccctt    3840
tgtatccccc aatgggtttc aagagagtcc ccctggggta ctctctttgc gcctatccga    3900
acctctagtt acctccaatg gcatgcttgc gctcaaaatg gcaacggcc tctctctgga    3960 cgaggccggc aaccttacct cccaaaatgt aaccactgtg agcccacctc tcaaaaaaac    4020
caagtcaaac ataaacctgg aaatatctgc accctcaca gttacctcag aagccctaac    4080
tgtggctgcc gccgcacctc taatggtcgc gggcaacaca ctcaccatgc aatcacaggc    4140
```

-continued

```
cccgctaacc gtgcacgact ccaaacttag cattgccacc caaggacccc tcacagtgtc    4200
agaaggaaag ctagccctgc aaacatcagg cccccctcacc accaccgata gcagtacccct    4260 tactatcact gcctcacccc ctctaactac tgccactggt agcttgggca ttgacttgaa    4320
agagcccatt tatacacaaa atggaaaact aggactaaag tacggggctc ctttgcatgt    4380
aacagacgac ctaaacactt tgaccgtagc aactggtcca ggtgtgacta ttaataatac    4440
ttccttgcaa actaaagtta ctggagcctt gggttttgat tcacaaggca atatgcaact    4500
taatgtagca ggaggactaa ggattgattc tcaaaacaga cgccttatac ttgatgttag    4560
ttatccgttt gatgctcaaa accaactaaa tctaagacta ggacagggcc ctcttttat    4620 aaactcagcc cacaacttgg atattaacta caacaaaggc ctttacttgt ttacagcttc    4680
aaacaattcc aaaaagcttg aggttaacct aagcactgcc aaggggttga tgtttgacgc    4740
tacagccata gccattaatg caggagatgg gcttgaattt ggttcaccta atgcaccaaa    4800
cacaaatccc ctcaaaacaa aaattggcca tggcctagaa tttgattcaa acaaggctat    4860
ggttcctaaa ctaggaactg gccttagttt tgacagcaca ggtgccatta cagtaggaaa    4920
caaaaataat gataagctaa cccta                                          4945
```

ONCOLYTIC ADENOVIRUSES CODING FOR BI-SPECIFIC ANTIBODIES

FIELD OF THE INVENTION

The present invention relates to the fields of life sciences and medicine. Specifically, the invention relates to cancer therapies of humans. More specifically, the present invention relates to an oncolytic adenoviral vector encoding a bispecific monoclonal antibody. Furthermore, the present invention relates to methods and uses utilizing the oncolytic adenoviral vectors, also together with adoptive cell therapies.

BACKGROUND OF THE INVENTION

Novel therapies are constantly developed for cancer treatment. Adoptive cell therapies (ACT) are a potent approach for treating cancer but also for treating other diseases such as infections and graft versus host disease. Adoptive cell transfer is the passive transplantation of ex vivo grown cells, most commonly immune-derived cells, into a host with the goal of transferring the immunologic functionality and characteristics of the transplant. Adoptive cell transfer can be autologous, as is common in adoptive T-cell therapies, or allogeneic as typical for treatment of infections or graft-versus-host disease. Clinically, common embodiments of this approach include transfer of either immune-promoting or tolerogenic cells such as lymphocytes to patients to either enhance immunity against viruses and cancer or to promote tolerance in the setting of autoimmune disease, such as type I diabetes or rheumatoid arthritis.

The adoptive transfer of autologous tumor infiltrating lymphocytes (TILs) or genetically re-directed peripheral blood mononuclear cells has been used to successfully treat patients with melanoma as well as patients with CD19-expressing hematologic malignancies. In ACT, the most commonly used cell types are T-cells, sometimes sorted for CD8+, but other variations include CD4+ cells, NK-cells, delta-gamma T-cells, regulatory T-cells and peripheral blood mononuclear cells. Cells can be unmodified such as in TIL therapy or genetically modified. In TIL therapy unsorted polyclonal cells are used. There are two common ways to achieve genetic targeting of T-cells to tumor specific targets. One is transfer of a T-cell receptor with known specificity (TCR therapy) and with matched human leukocyte antigen (HLA, known as major histocompatibility complex in rodents) type. The other is modification of cells with artificial molecules such as chimeric antigen receptors (CAR). This approach is not dependent on HLA and is more flexible with regard to targeting cell surface molecules. For example, single chain antibodies can be used and CARs can also incorporate costimulatory domains. However, the targets of CAR cells need to be on the membrane of target cells, while TCR modifications can utilize intracellular targets. In TCR and CAR therapy, T-cells are obtained from peripheral blood of the patient.

Despite of the development of adoptive cell therapies, the clinical results of adoptive T-cell therapy on non-melanoma solid tumors, constituting more than 90% of human cancers, and 95% of cancer mortality, has been disappointing. The main reason for this is that the tumor microenvironment is highly immunosuppressive, which inactivates and anergizes the T-cell graft, inhibits local propagation of the graft, and hinders trafficking of the adoptively transferred T-cells to the tumor. Currently there are no effective tools for resolving said issues.

T-cell engagers have been used for cancer treatment. The main classes are trifunctional antibody, chemically linked Fab and bi-specific T-cell engager (BiTE), the latter being most advanced clinically (Baeuerle P A, Reinhardt C. Cancer Res. 2009 Jun. 15; 69(12):4941-4). While several BiTEs have been studied preclinically, and two (blinatumomab, an anti-CD19 BiTE, and solitomab, and anti-EpCAM Bite) have been in clinical trials, a number of problems have emerged. A major issue is on-target-off-tumor toxicity, which has resulted in a high adverse event rate including a toxic death rate of 12% in blinatumomab clinical trials (Topp M S et al. 2011, J Clin Oncol. June 20; 29(18):2493-8). Another issue is insufficient concentrations of the BiTE at the target (the tumor), which is especially problematic in the context of solid tumors whose bulk forms an obstacle to BiTE penetration and concentration. This probably explains why no formal responses (reductions in tumor size fulfilling RECIST criteria) have been seen in trials with solitomab. The best responses were transient stable disease which was achieved in 38% of patients (Walter M et al. 2012, J Clin Oncol 30, (suppl; abstr 2504)). Still a further problem with BiTEs is the short half-life in humans, which has necessitated continuous infusion, which is not a practical solution for routine use.

Oncolytic viral vectors armed with a T-cell engager have been suggested for cancer treatment. WO 2014138314 A1 (PCT/US2014/020935) and Yu et al. (2014, Mol Ther 22(1): 102-11) describe oncolytic vaccinia viruses coding for an anti-EphA2 BiTe. With regard to vectored delivery of BiTEs, single-chain molecules, including dual-single-chain constructs such as BiTEs, are not automatically secreted from mammalian cells. In fact, the poor secretion of single-chain molecules and construct such as BiTEs has formed an obstacle in their gene therapy use. Antibodies are normally produced by B-cell lineage plasma cells and thus it is no surprise their production and release from epithelial tumor cells is problematic.

With regard to efficacy of oncolytic viral vectors, either alone or together with other therapies, room is left for improvement. Increased specificity and sufficient tumor killing ability of therapies in general are warranted.

The present invention provides efficient tools and methods for cancer therapeutics by utilizing specific viral vectors, e.g. with adoptive cell therapies.

BRIEF DESCRIPTION OF THE INVENTION

An object of the present invention is to provide simple methods and tools for overcoming the above problems of inefficient, unsafe and unpredictable cancer therapies. In one embodiment, the invention provides novel methods and means for cell therapy. The objects of the invention are achieved by specific viral vectors, methods and arrangements, which are characterized by what is stated in the independent claims. The specific embodiments of the invention are disclosed in the dependent claims.

The present invention proposes use of specific oncolytic adenoviruses to resolve the issues of highly immunosuppressive tumor microenvironment, which inactivates and anergizes the T-cell graft, inhibits local propagation of the graft, and hinders trafficking of the adoptively transferred T-cells to the tumor. The invention is based on the surprising realization that oncolytic adenoviruses coding for bi-specific T-cell engagers (BiTE) can resolve said issues (FIG. 1). In particular, data related to the present invention indicates that adenovirus can induce danger signals in tumors of mice and in humans, as exemplified by interferon gamma production (FIG. 2), which leads to reduction in TIM3 (TIM3 is a key indicator of tumor immunosuppression) expression (FIG. 3). Importantly, even if adenovirus alone is able to produce danger signals at the tumor, this is not sufficient to recruit T-cells to the tumor (FIG. 4). Thus, for optimal enhancement of adoptive cell therapy, arming of oncolytic adenovirus with BiTE is required (FIG. 1).

Of note, we have human data showing that TIM3 expression, and the ability of oncolytic adenovirus to downregulate TIM3, correlates with patient survival. This is potent data indicating that the danger signaling caused by adenovirus results in down-regulation of tumor immunosuppression, which correlates with clinical benefits in patients (FIG. 10). Importantly, not all oncolytic viruses are alike, and in fact vaccinia virus is not able to produce danger signals in tumors, and is therefore not comparable with adenovirus for tumor immunotherapy via local production of BiTE (FIG. 5-6).

Issues of systemic toxicity and poor local efficacy as well as the short half-life of BiTEs in humans are resolved by the present invention, namely by local production of the BiTE by an adenoviral vector at the tumor, a feature which is advantageous especially in the context of solid tumors (FIG. 9).

Also, the present invention resolves the problem of poor secretion of single-chain BiTE molecules in a surprising manner: when using an oncolytic adenovirus, which replicates only in tumor cells, and the last step of replication is lysis of the cell, the BiTE is released into the tumor microenvironment (FIG. 8). In other words, the present invention resolves the problem of BiTE secretion in a surprising manner, by utilizing oncolysis as the release device. According to the present invention secretion of BiTEs is not required, and in fact not preferred as a further approach is for restricting BiTE expression to the tumor (only tumor cells are lysed by the virus).

Production of the BiTE at the tumor can recruit the adoptive T-cell graft to the tumor (FIG. 1). Binding to the cell surface molecule receptor (e.g. CD3 receptor) activates cells of the graft at the tumor. Moreover, adenoviral oncolysis causes danger signals which counteract tumor immunosuppression. Together, these components achieve an anti-immunosuppressive effect which could not be achieved with any component alone. Of note, adenovirus is unique among oncolytic viruses with regard to its ability to induce anti-immunosuppressive danger signals, through binding to pathogen associated pattern recognition receptors. Moreover, adenovirus has outstanding effects on T-cells, while many other oncolytic viruses such as vaccinia virus are rather stealthy in this regard. In other words, vaccinia cannot be used for enhancing adoptive cell therapy. Finally, the present specification represents data showing that vaccinia is not a good platform for enhancing adoptive cell therapy, while adenovirus is the optimal device for counteracting tumor immunosuppression.

Anti-viral immunity has been considered restrictive for virotherapy approaches including oncolytic adenoviruses. One embodiment of anti-viral immunity is anti-viral T-cells. However, the present invention surprisingly reveals that when an oncolytic adenovirus is used for production of a BiTE at the tumor, anti-viral T-cells can be retargeted against the tumor. This effect amplifies during treatment, as replication of the oncolytic virus results in further anti-viral T-cells, which then are also targeted towards the tumor through the BiTE produced by the virus (FIG. 7).

In one embodiment, the present invention relates to enhancement of T-cell therapy with an oncolytic adenovirus coding for a BiTE. Oncolytic adenovirus is the optimal platform for using a BiTe for enhancing T-cell therapy, because of the unexpected synergy between the anti-immunosuppressive effects of oncolysis and BiTE expression at the tumor.

The present specification describes construction of recombinant adenoviral vectors, methods related to the adenoviral vectors, and their different uses. Furthermore, the adenoviral vectors of the present invention coding for T-cell engagers may be combined with adoptive cell therapeutics for cancer treatment.

Advantages of the present invention are achieved by a method of treating malignancy, comprising administering an effective amount of an adenoviral vector of the present invention (e.g. alone or together with TILs) to a patient afflicted with cancer to cause regression or stabilization of the cancer.

The present invention relates to an oncolytic adenoviral vector comprising
 a deletion of a nucleic acid sequence in the E3 region, and
 a nucleic acid sequence encoding a bispecific monoclonal antibody in the place of the deleted nucleic acid sequence in E3 region.

The present invention also relates to an oncolytic adenoviral vector comprising
 a deletion of a nucleic acid sequence in the E3 region, and
 a nucleic acid sequence encoding a bispecific monoclonal antibody in the place of the deleted nucleic acid sequence in E3 region,
 wherein the bispecific monoclonal antibody comprises a single chain variable fragment (scFv) specific for a cell surface molecule and a scFv specific for a tumor antigen.

Also, the present invention relates to a pharmaceutical composition comprising an oncolytic adenoviral vector comprising a deletion of a nucleic acid sequence in the E3 region, and a nucleic acid sequence encoding a bispecific monoclonal antibody in the place of the deleted nucleic acid sequence in E3 region.

Furthermore, the present invention relates to a combination of an oncolytic adenoviral vector comprising a deletion of a nucleic acid sequence in the E3 region and a nucleic acid sequence encoding a bispecific monoclonal antibody in the place of the deleted nucleic acid sequence in E3 region, and an adoptive cell therapeutic composition.

Furthermore, the present invention relates to a combination of an oncolytic adenoviral vector of the invention and an adoptive cell therapeutic composition for use in treatment of cancer.

Furthermore, the present invention relates to an oncolytic adenoviral vector of the invention together with an adoptive cell therapeutic composition for use in treatment of cancer.

Furthermore, the present invention relates to an oncolytic adenoviral vector of the invention for use in treatment of cancer together with an adoptive cell therapeutic composition.

Still, the present invention relates to a method of treating cancer in a subject, wherein the method comprises administration of an oncolytic adenoviral vector of the invention to a subject.

Still, the present invention relates to an oncolytic adenoviral vector comprising a deletion in the E3 region and a nucleic acid sequence encoding a bispecific monoclonal antibody in the place of the deleted region of E3, for use in increasing the efficacy of adoptive cell therapy in a subject.

Still, the present invention relates to a method of increasing the efficacy of adoptive cell therapy in a subject by administering an oncolytic adenoviral vector comprising a deletion in the E3 region and a nucleic acid sequence encoding a bispecific monoclonal antibody in the place of the deleted region of E3, to a subject in need thereof, wherein the subject has been administered or is to be administered with adoptive cell therapy.

Also, the present invention relates to a use of an oncolytic adenoviral vector of the present invention in the manufacture of a medicament for treating cancer in a subject.

Also, the present invention relates to a use of an oncolytic adenoviral vector of the invention in the manufacture of a medicament for increasing the efficacy of adoptive cell therapy in a subject.

The advantages of the arrangements of the present invention include but are not limited to enhanced therapeutic effect and reduced side effects. Severe adverse events, even deaths are prevented, because enhancements in efficacy, and the anti-suppressive effects of our approach, may reduce the need for preconditioning chemotherapy and/or radiation used in the prior art methods to "make room" for transferred cells and reduce tumor immunosuppression.

BRIEF DESCRIPTION OF THE DRAWINGS

In the following the invention will be described in greater detail by means of specific embodiments with reference to the attached drawings, in which

FIGS. 13 (A and B) reveal in vitro lytic activity of Ad 5/3-E2F-d24-E3 virus in combination with human CD3 specific EpCAM targeted BiTE (Anti-human EpCam, Cat#CABT-33295MH) and PBMCs against colon carcinoma cell line SW480.

Arming the virus with a molecule able to induce anti-tumor immunity (for example BITe) is necessary for inducing protective immunity (=a sign of memory response against tumor epitopes).

Figure 17:
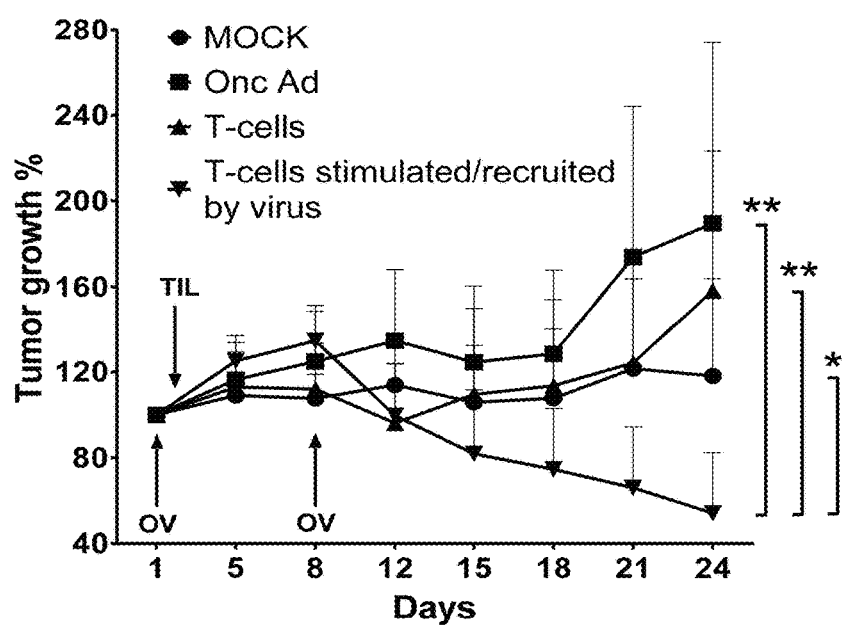

FIG. 17 shows in vivo efficacy of armed or unarmed oncolytic adenovirus, with or without T-cell therapy. Established HapT1 tumors were injected intratumorally with oncolytic adenovirus Ad5/3-E2F-d24 ($1\times10^7$ VP/tumor) on Days 1 and 8. On Day 2, HapT1 tumor infiltrating lymphocytes grown ex vivo ($1.5\times10^6$ TIL/tumor) were administered intratumorally. Error bars, SE. *p<0.05, **p<0.01. The best anti-tumor efficacy was seen when tumors were treated with an oncolytic virus and TILs were also given.

Figure 18:
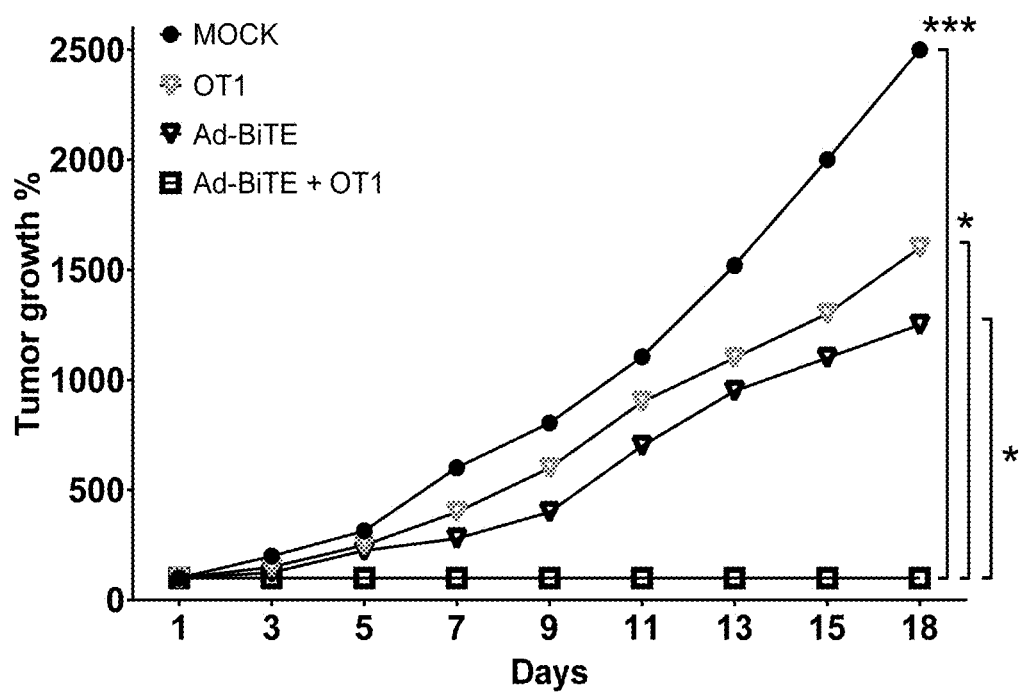

FIG. 18 shows hypothetical results from in vivo antitumor efficacy experiment combining Ad-BiTE and OT1 T-cell transfer in immunocompetent mice bearing B16-OVA tumors. Subcutaneously implanted B16-OVA tumors (0.25× 10e6 cells/tumor) will be treated with a single intraperitoneal injection of CD8-enriched OT1 T-cells, intratumoral injection of Ad-BiTE (1×10e9 VP/tumor) or both. Virus injections will be repeated every 7 days.

Figure 19:
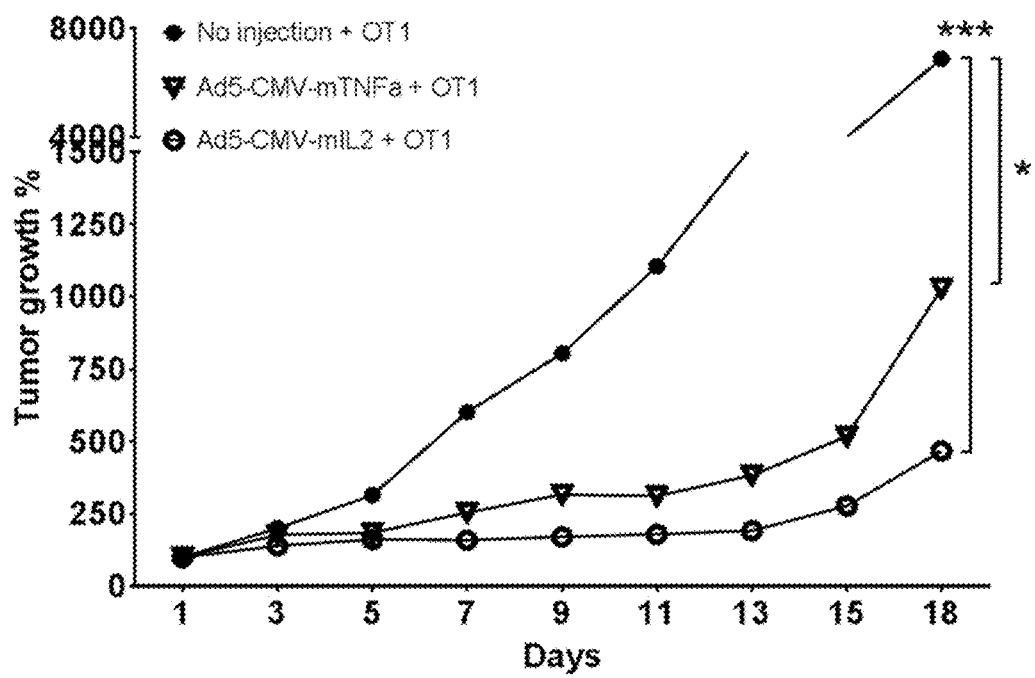

FIG. 19 shows that adenoviral delivery of cytokines IL2 and TNFa enhance efficacy of adoptive cell therapy, providing the rationale for including cytokines in oncolytic adenovirus coding for BiTE. B16-OVA tumor-bearing C57 mice were treated intratumorally with 1×10e9 viral particles of armed adenoviruses and intraperitoneally with 1.5×10e6 CD8-enriched OT-1 T-cells on Day 1. Virus treatments continued every 7 days.

Figure 20:
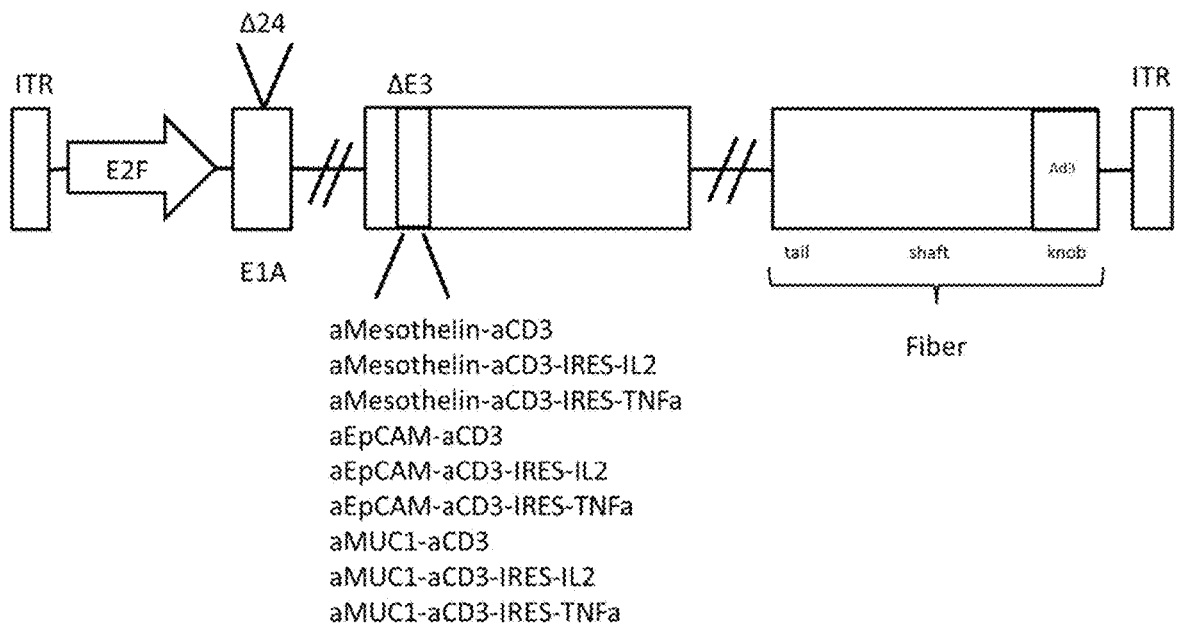

FIG. 20 shows construct design of the present invention.

Figure 21:
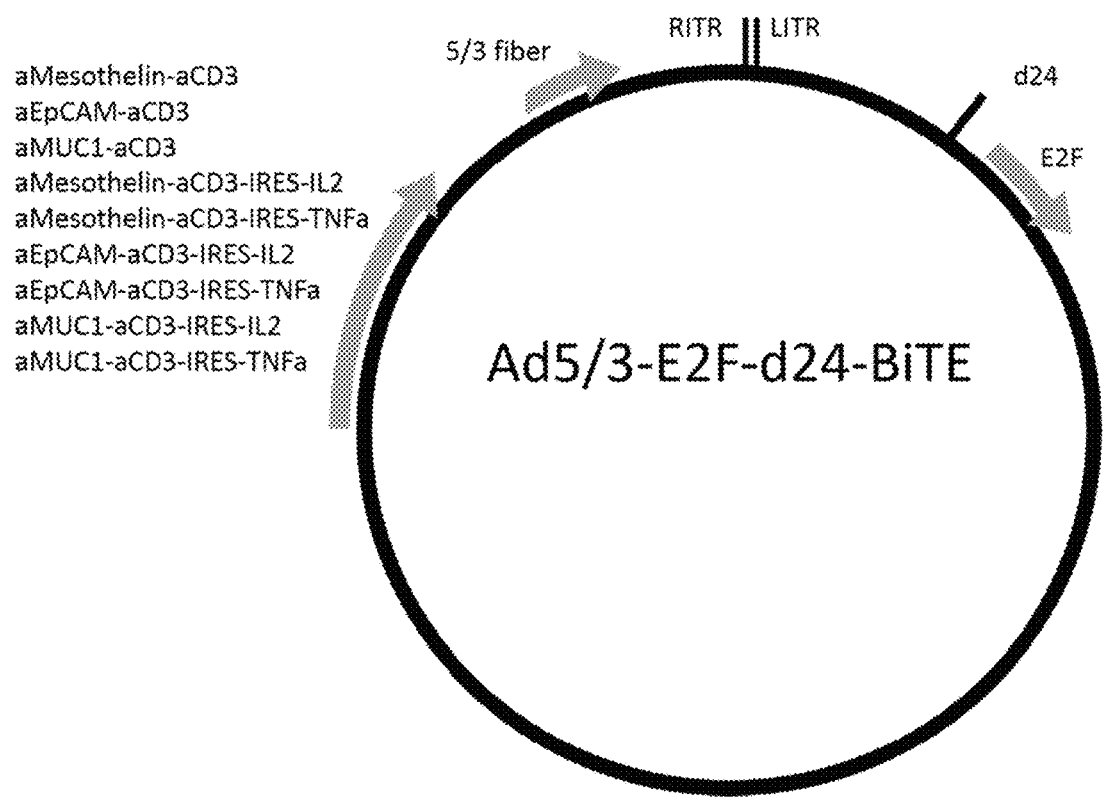

FIG. 21 shows a construct map of the present invention.

DETAILED DESCRIPTION OF THE INVENTION

Viral Vectors

The oncolytic adenoviral vectors used in the present invention can be any adenoviral vectors suitable for treating a human or animal. As used herein "an oncolytic adenoviral vector" refers to an adenoviral vector capable of infecting and killing cancer cells by selective replication in tumor versus normal cells.

In one embodiment of the invention, the adenoviral vectors are vectors of human viruses. In one embodiment the adenoviral vectors are selected from the group consisting of Ad5, Ad3 and Ad5/3 vectors. As used herein, expression "adenovirus serotype 5 (Ad5) nucleic acid backbone" refers to the genome of Ad5. Similarly "adenovirus serotype 3 (Ad3) nucleic acid backbone" refers to the genome of Ad3. "Ad5/3 vector" refers to a chimeric vector comprising or having parts of both Ad5 and Ad3 vectors. In a specific embodiment a backbone of the adenoviral vector is an adenovirus serotype 5 (Ad5) or serotype 3 (Ad3) nucleic acid backbone with specific mutations. E.g. fiber areas of the vector can be modified. In one embodiment the backbone is Ad5 nucleic acid backbone further comprising an Ad3 fiber knob. In other words the construct has the fiber knob from Ad3 while the remainder or the most of the remainder of the genome is from Ad5. (See e.g. FIG. 20)

The adenoviral vectors may be modified in any way known in the art, e.g. by deleting, inserting, mutating or modifying any viral areas. The vectors are made tumor specific with regard to replication. For example, the adenoviral vector may comprise modifications in E1, E3 and/or E4 such as insertion of tumor specific promoters (e.g. to drive E1), deletions of areas (e.g. the constant region 2 of E1 as used in "D24", E3/gp19k, E3/6.7k) and insertion of transgenes.

One approach for generation of a tumor specific oncolytic adenovirus is engineering a 24 base pair deletion (D24) affecting the constant region 2 (CR2) of E1. In wild type adenovirus CR2 is responsible for binding the cellular Rb tumor suppressor/cell cycle regulator protein for induction of the synthesis (S) phase i.e. DNA synthesis or replication phase. The interaction between pRb and E1A requires amino acids 121 to 127 of the E1A protein conserved region, which are deleted in the present invention. The vector of the present invention comprises a deletion of nucleotides corresponding to amino acids 122-129 of the vector according to Heise C. et al. (2000, Nature Med 6, 1134-1139). Viruses with the D24 are known to have a reduced ability to overcome the G1-S checkpoint and replicate efficiently only in cells where this interaction is not necessary, e.g. in tumor cells defective in the Rb-p16 pathway, which includes most if not all human tumors. In one embodiment of the invention the vector comprises a 24 bp deletion (D24) in the Rb binding constant region 2 of adenoviral E1 (See FIG. 20)

It is also possible to replace E1A endogenous viral promoter for example by a tumor specific promoter. In a specific embodiment of the invention e.g. E2F1 (e.g. in Ad5 based vector) or hTERT (e.g. in Ad3 based vector) promoter is utilized in the place of E1A endogenous viral promoter. On one embodiment the vector comprises E2F1 promoter for tumor specific expression of E1A.

The E3 region is nonessential for viral replication in vitro, but the E3 proteins have an important role in the regulation of host immune response i.e. in the inhibition of both innate and specific immune responses. In one embodiment of the invention the deletion of a nucleic acid sequence in the E3 region of the oncolytic adenoviral vector is a deletion of viral gp19k and 6.7k reading frames. The gp19k/6.7K deletion in E3 refers to a deletion of 965 base pairs from the adenoviral E3A region. In a resulting adenoviral construct, both gp19k and 6.7K genes are deleted (Kanerva A et al. 2005, Gene Therapy 12, 87-94). The gp19k gene product is known to bind and sequester major histocompatibility complex I (MHC1, known as HLA1 in humans) molecules in the endoplasmic reticulum, and to prevent the recognition of infected cells by cytotoxic T-lymphocytes. Since many tumors are deficient in HLA1/MHC1, deletion of gp19k increases tumor selectivity of viruses (virus is cleared faster than wild type virus from normal cells but there is no difference in tumor cells). 6.7K proteins are expressed on cellular surfaces and they take part in downregulating TNF-related apoptosis inducing ligand (TRAIL) receptor 2. (See FIG. 20)

Both of deletions gp19k and 6.7K provide a surprising advantage with regard to a specific embodiment of the invention. Since we are attempting to regain expression of HLA/MHC for presentation of tumor epitopes to the adoptively transferred T-cells, expression of the gp19k protein is counterproductive and in fact the upregulation of HLA/MHC requires deletion of gp19k. With regard to 6.7k, since one specific embodiment of our invention is production of TNFalpha from the virus, and one of its anti-tumor activities is a direct anti-tumor proapoptotic effect (on both transduced and non-transduced bystander cells), the presence of 6.7k is counterproductive.

In one embodiment of the invention, one or more transgenes are placed into a gp19k/6.7k deleted E3 region, under the E3 promoter. This restricts transgene expression to tumor cells that allow replication of the virus and subsequent activation of the E3 promoter. In a specific embodiment a nucleic acid sequence encoding a bipartite molecule comprising a single chain variable fragment (scFv) specific for a cell surface molecule and a scFv specific for a tumor antigen is inserted into the place of the deleted nucleic acid sequence of viral gp19k and 6.7k reading frames. In another embodiment of the invention E3 gp19k/6.7k is kept in the vector but one or many other E3 areas have been deleted (e.g. E3 9-kDa, E3 10.2 kDa, E3 15.2 kDa and/or E3 15.3 kDa).

E3 promoter may be any exogenous (e.g. CMV or E2F promoter) or endogenous promoter known in the art, specifically the endogenous E3 promoter. Although the E3 promoter is chiefly activated by replication, some expression occurs when E1 is expressed. As the selectivity of D24 type viruses occurs post E1 expression (when E1 is unable to bind Rb), these viruses do express E1 also in transduced normal cells. Thus, it is of critical importance to regulate also E1 expression to restrict E3 promoter mediated transgene expression to tumor cells.

Specific embodiments of the invention include oncolytic adenoviral vectors (e.g. Ad5 or Ad3 vectors) whose replication is restricted to the p16/Rb pathway by dual selectivity devices: an E2F (e.g. E2F1) tumor specific promoter placed in front of the adenoviral E1A gene which has been mutated in constant region 2, so that the resulting E1A protein is unable to bind Rb in cells. Furthermore, the fiber is modified by 5/3 chimerism to allow efficient entry into tumor cell. And still, the BiTE transgene, optionally with other transgenes, is placed into the E3 region, which has been deleted for gp19k and 6.7k open reading frames. This arming approach links transgene expression to virus replication without the need for heterologous promoters. L(left)- and/or R(right)-ITR sequences may also be comprised in the vector in specific embodiments. The inverted terminal repeat (ITR) sequences enable efficient multiplication of the viral genome and give ability to form a hairpin among other properties.

In a specific embodiment of the invention the oncolytic adenoviral vector comprises:

1) E2F1 promoter for tumor specific expression of E1A
2) a 24 bp deletion (D24) in the Rb binding constant region 2 of adenoviral E1;
3) a nucleic acid sequence deletion of viral gp19k and 6.7k reading frames; and
4) a nucleic acid sequence encoding a bipartite molecule comprising a single chain variable fragment (scFv) specific for a cell surface molecule and a scFv specific for a tumor antigen in the place of the deleted nucleic acid sequence as defined in point 3). (See FIG. 20)

A bispecific monoclonal antibody (BsMAb, BsAb) is an artificial protein that is composed of fragments of two different monoclonal antibodies and consequently is able to bind two different types of antigens. In other words, bispecific antibodies combine two or more antigen-recognizing elements into a single construct, which is able to bind to two or more targets.

Examples of bispecific monoclonal antibodies include BsMAbs, which are engineered to simultaneously bind to a cytotoxic cell (using a receptor such as CD3) and a target like a tumor cell to be destroyed. First-generation BsMAb, called trifunctional antibody, has been developed. It consists of two heavy and two light chains, one each from two different antibodies. The two Fab regions (the arms) are directed against two antigens. The Fc region (the foot) is made up from the two heavy chains and forms the third binding site; hence the name. Other types of bispecific antibodies include chemically linked Fabs, consisting only of the Fab regions, and various types of bivalent and trivalent single-chain variable fragments (scFvs) (i.e. fusion proteins mimicking the variable domains of two antibodies). In a specific embodiment of the invention, the bispecific monoclonal antibody is selected from the group consisting of trifunctional antibodies and bivalent and trivalent single-chain variable fragments (scFvs). In one embodiment of the invention the bispecific monoclonal antibody is a bivalent single-chain variable fragment. The group of bivalent single-chain variable fragments comprises bi-specific T-cell engagers (BiTEs) and mAb2's (i.e. antibodies engineered to contain an Fcab antigen-binding fragment instead of the Fc constant region).

Bi-specific T-cell engagers (BiTEs) are a class of artificial bispecific monoclonal antibodies. They direct a host's immune system, more specifically the T cells' cytotoxic activity, against cancer cells. BiTEs are fusion proteins consisting of two single-chain variable fragments (scFvs) of different antibodies, or amino acid sequences from four different genes, on a single peptide chain of about 55 kilodaltons. One of the scFvs binds to T cells via a cell surface molecule (e.g. the CD3 receptor), and the other to a tumor cell via a tumor specific molecule.

In a specific embodiment the bispecific monoclonal antibody is a bipartite molecule comprising a single chain variable fragment (scFv) specific for a cell surface molecule and a scFv specific for a tumor antigen. As used herein "specific for a cell surface molecule" refers to an ability to bind a specific type cell surface molecule. Also as used herein "specific for a tumor antigen" refers to an ability to bind a specific type tumor antigen.

In one embodiment of the invention the cell surface molecule is on immunological effector cells. As used herein "an immunological effector cell" refers to a cell selected from the group consisting of T-cells, CD8+ cells, CD4+ cells, NK-cells, delta-gamma T-cells, regulatory T-cells, and peripheral blood mononuclear cells. In a specific embodiment, the effector cells are T-cells i.e. T lymphocytes. In one embodiment the cell surface molecule may be selected from CD3, CD8 and CD4.

In one embodiment the tumor antigen is selected from Table 1 or from the group consisting of mesothelin, EpCAM1 and MUC1.

In one embodiment the cell surface molecule is CD3 and the tumor antigen is selected from Table 1 or from mesothelin, EpCAM1 or MUC1. In another embodiment the cell surface molecule is CD8 and the tumor antigen is selected from Table 1 or from mesothelin, EpCAM1 or MUC1. In further embodiment the cell surface molecule is CD4 and the tumor antigen is selected from Table 1 or from mesothelin, EpCAM1 or MUC1. In a very specific embodiment, the tumor antigen is mesothelin and the cell surface molecule is CD3; the tumor antigen is EpCAM1 and the cell surface molecule is CD3; or the tumor antigen is MUC1 and the cell surface molecule is CD3. Indeed, regarding the BiTe transgenes, specific examples include anti-mesothelin-linker-anti-CD3, anti-EpCAM1-linker-anti-CD3 and anti-MUC1-linker-anti-CD3.

TABLE 1

Examples of tumor antigens suitable for the present invention
(http://cvc.dfci.harvard.edu/cvccgi/tadb/nomenclature.pl).
Antigen Name

| ERBB2 | SSX2 | KRAS | TERT |
| BIRC5 | SSX4 | PRAME | MGAT5 |

TABLE 1-continued

Examples of tumor antigens suitable for the present invention
(http://cvc.dfci.harvard.edu/cvccgi/tadb/nomenclature.pl).
Antigen Name

| | | | |
|---|---|---|---|
| CEACAM5 | KRAS | NRAS | CEL |
| WDR46 | PRAME | ACTN4 | F4.2 |
| BAGE | NRAS | CTNNB1 | CAN |
| CSAG2 | ACTN4 | CASP8 | ETV6 |
| DCT | CTNNB1 | CDC27 | BIRC7 |
| MAGED4 | CASP8 | CDK4 | CSF1 |
| GAGE1 | CDC27 | EEF2 | OGT |
| GAGE2 | CDK4 | FN1 | MUC1 |
| GAGE3 | EEF2 | HSPA1B | MUC2 |
| GAGE4 | FN1 | LPGAT1 | MUM1 |
| GAGE5 | HSPA1B | ME1 | CTAG1 |
| GAGE6 | LPGAT1 | HHAT | CTAG2 |
| GAGE7 | ME1 | TRAPPC1 | CAMEL |
| GAGE8 | HHAT | MUM3 | MRPL28 |
| IL13RA2 | TRAPPC1 | MYO1B | FOLH1 |
| MAGEA1 | MUM3 | PAPOLG | RAGE |
| MAGEA2 | MYO1B | OS9 | SFMBT1 |
| MAGEA3 | PAPOLG | PTPRK | KAAG1 |
| MAGEA4 | OS9 | TPI1 | SART1 |
| MAGEA6 | PTPRK | ADFP | TSPYL1 |
| MAGEA9 | TPI1 | AFP | SART3 |
| MAGEA10 | ADFP | AIM2 | SOX10 |
| MAGEA12 | AFP | ANXA2 | TRG |
| MAGEB1 | AIM2 | ART4 | WT1 |
| MAGEB2 | ANXA2 | CLCA2 | TACSTD1 (EPCAM) |
| MAGEC2 | ART4 | CPSF1 | SILV |
| TP53 | CLCA2 | PPIB | SCGB2A2 |
| TYR | CPSF1 | EPHA2 | MC1R |
| TYRP1 | PPIB | EPHA3 | MLANA |
| SAGE1 | SSX2 | FGF5 | GPR143 |
| SYCP1 | SSX4 | CA9 | OCA2 |
| KLK3 | UBXD5 | SIRT2 | SPA17 |
| SUPT7L | EFTUD2 | SNRPD1 | KLK4 |
| ARTC1 | GPNMB | HERV-K-MEL | ANKRD30A |
| BRAF | NFYC | CXorf61 | RAB38 |
| CASP5 | PRDX5 | CCDC110 | CCND1 |
| CDKN2A | ZUBR1 | VENTXP1 | CYP1B1 |
| MDM2 | NPM1 | LRP1 | CCNB1 |
| MMP2 | ALK | ADAM17 | PAX3-FKHR |
| ZNF395 | PML1 | JUP | PAX3 |
| RNF43 | RARA | DDR1 | FOXO1 |
| SCRN1 | SYT | ITPR2 | XBP1 |
| STEAP1 | SSX1 | HMOX1 | SYND1 |
| 707-AP | MSLN | TPM4 | ETV5 |
| TGFBR2 | UBE2V1 | BAAT | HSPA1A |
| PXDNL | HNRPL | DNAJC8 | HMHA1 |
| AKAP13 | WHSC2 | TAPBP | TRIM68 |
| PRTN3 | EIF4EBP1 | LGALS3BP | |
| PSCA | WNK2 | PAGE4 | |
| RHAMM | OAS3 | PAK2 | |
| ACPP | BCL-2 | CDKN1A | |
| ACRBP | MCL1 | PTHLH | |
| LCK | CTSH | SOX2 | |
| RCVRN | ABCC3 | SOX11 | |
| RPS2 | BST2 | TRPM8 | |
| RPL10A | MFGE8 | TYMS | |
| SLC45A3 | TPBG | ATIC | |
| BCL2L1 | FMOD | PGK1 | |
| DKK1 | XAGE1 | SOX4 | |
| ENAH | RPSA | TOR3A | |
| CSPG4 | COTL1 | TRGC2 | |
| RGS5 | CALR3 | BTBD2 | |
| BCR | PA2G4 | SLBP | |
| BCR-ABL | EZH2 | EGFR | |
| ABL-BCR | FMNL1 | IER3 | |
| DEK | HPSE | TTK | |
| DEK-CAN | APC | LY6K | |
| ETV6-AML1 | UBE2A | IGF2BP3 | |
| LDLR-FUT | BCAP31 | GPC3 | |
| NPM1-ALK1 | TOP2A | SLC35A4 | |
| PML-RARA | TOP2B | HSMD | |
| SYT-SSX1 | ITGB8 | H3F3A | |
| SYT-SSX2 | RPA1 | ALDH1A1 | |
| FLT3 | ABI2 | MFI2 | |
| ABL1 | CCNI | MMP14 | |
| AML1 | CDC2 | SDCBP | |
| LDLR | SEPT2 | PARP12 | |
| FUT1 | STAT1 | MET | |

In one embodiment the vector of the invention encodes a bispecific monoclonal antibody but also may comprise other transgenes. In a specific embodiment the oncolytic adenoviral vector codes for two or more transgenes. Particular embodiments of the present invention include adenoviral vectors encoding bispecific T-cell engager and at least one cytokine. Cytokines used in the present invention can be selected from any known cytokines in the art. In a specific embodiment of the invention the cytokine is IL-2, TNFalpha or CD40L. Indeed, in addition to a bispecific monoclonal antibody the oncolytic adenoviral vector may further comprise e.g. IL-2, TNFalpha and/or CD40L transgene(s).

Cytokines participate in immune response by acting through various mechanisms including recruitment of T-cells towards the tumor. The nucleotide sequence encoding a cytokine transgene may be from any animal such as a human, ape, rat, mouse, hamster, dog or cat, but specifically it is encoded by a human sequence. The nucleotide sequence encoding the transgene may be modified in order to improve its effects, or unmodified i.e. of a wild type.

Furthermore, the combination of adenoviral vectors encoding both a BiTE and at least one cytokine, with adoptive cell therapeutics provides more effective results on wider targets than could have been assumed.

The other cytokines function by attracting and activating the T cells and reducing tumor immunosuppression, while IL-2 induces the propagation of the T-cell graft. Thus, IL-2 is produced locally at the tumor where it is needed, instead of injected systemically as is typically done in T-cell therapy, which can cause side effects, and therefore a major problem of the prior art therapies (i.e. toxicity of systemic IL-2) can be prevented by this embodiment. Indeed, severe adverse events, even deaths are prevented, because separate addition of IL2 used in the prior art methods to propagate and sustain transferred cells after transferring them into a patient is not needed if the virus produces it while replicating in the tumor. Local production at the tumor can also enhance the sought-after effects of IL-2 (stimulation and propagation of the graft) while reducing systemic exposure which is the cause of adverse events. The present invention provides selective treatments, with less toxicity or damage to healthy tissues.

The danger signaling provided by replication of the oncolytic virus, and activation of pathogen associated molecular pattern recognition receptors by viral DNA, together with the action of the transgene(s) may reduce tumor immunosuppression to such degree that preconditioning therapy can be omitted. Consequently, and major issue in prior art, toxicity due to preconditioning chemotherapy and radiation can be avoided.

In one embodiment of the invention the virus vector comprises an internal ribosomal entry site (IRES) or optionally a ribosome shunt site 2A between the two transgenes. Thus, IRES or a ribosome shunt site 2A may be between any transgenes, such as a bispecific monoclonal antibody and any cytokine. As used herein "IRES" refers to a nucleotide sequence that enables initiation of the translation in the middle of a messenger RNA sequence in protein synthesis. IRES can be from any virus, but in one embodiment of the invention IRES is from encephalomyocarditis virus (EMCV). As used herein "a ribosome shunt site 2A" refers to a translation initiation site in which ribosomes physically bypass parts of the 5' untranslated region to reach the initiation codon. Both the IRES and the A2 enable viruses to produce two transgenes from one promoter (the E3 promoter). IRES may be used for example in the following places in adenoviral constructs (FIG. 20): aMesothelin-aCD3-IRES-IL2 (see SEQ ID NOs: 1, 2, 3, 5, 6, 9); aMesothelin-aCD3-IRES-TNFa (see SEQ ID NOs: 1, 2, 3, 5, 6, 7); aEpCAM-aCD3-IRES-IL2 (see SEQ ID NOs: 1, 2, 3, 4, 5, 6); aEpCAM-aCD3-IRES-TNFa (see SEQ ID NOs: 1, 2, 3, 4, 5, 7); aMUC1-aCD3-IRES-IL2 (see SEQ ID NOs: 1, 2, 3, 5, 6, 8); aMUC1-aCD3-IRES-TNFa (see SEQ ID NOs: 1, 2, 3, 5, 7, 8). Nucleotide sequences are from the adenoviral constructs of the invention and are presented in Table 2.

Schematics of the general layouts of the virus genomes, which may be used, for example, in the present invention, are shown in FIG. 20 (Ad5/3-E2F-D24-transgene). Nucleotide sequences of the viral vectors comprising transgenes aMesothelin-aCD3 (e.g. aMesothelin-aCD3-IRES-IL2 see SEQ ID NOs: 1, 2, 3, 5, 6, 9; aMesothelin-aCD3-IRES-TNFa see SEQ ID NOs: 1, 2, 3, 5, 6, 7), aEpCAM-aCD3 (e.g. aEpCAM-aCD3-IRES-IL2 see SEQ ID NOs: 1, 2, 3, 4, 5, 6; aEpCAM-aCD3-IRES-TNFa see SEQ ID NOs: 1, 2, 3, 4, 5, 7), aMUC1-aCD3 (e.g. aMUC1-aCD3-IRES-IL2 see SEQ ID NOs: 1, 2, 3, 5, 6, 8; aMUC1-aCD3-IRES-TNFa see SEQ ID NOs: 1, 2, 3, 5, 7, 8) were constructed according to the sequences listed in Table 2. General methods for constructing adenoviral vectors are well known to a person skilled in the art and are described e.g. in Koski et al. 2010, Hemminki et al. 2015. These methods may also be utilized for constructing adenoviral vectors of the present invention.

In addition to other advantages described above, further advantages of the present invention utilizing viral vectors comprising at least one cytokine transgene are: i) cytokines and virus per se cause a danger signal which recruits T cells and other immune cells to tumors, ii) cytokines induce T cell proliferation both at the tumor and in local lymphoid organs, iii) cytokines and virus per se are able to induce T cells (both the adoptive T-cell graft and natural, innate anti-tumor T-cells) to propagate at the tumor, iv) cytokine and/or virus induce the upregulation of antigen-presenting molecules (HLA) on cancer cells, rendering them sensitive to recognition and killing by T cells, and v) cytokines and virus replication favorably alter tumor microenvironment by reducing immunosuppression and cellular anergy.

The viral vectors utilized in the present inventions may also comprise other modifications than described above. Any additional components or modifications may optionally be used but are not obligatory for the present invention.

Insertion of exogenous elements may enhance effects of vectors in target cells. The use of exogenous tissue or tumor-specific promoters is common in recombinant vectors and they can also be utilized in the present invention.

Adoptive Cell Therapy

Figure 1:
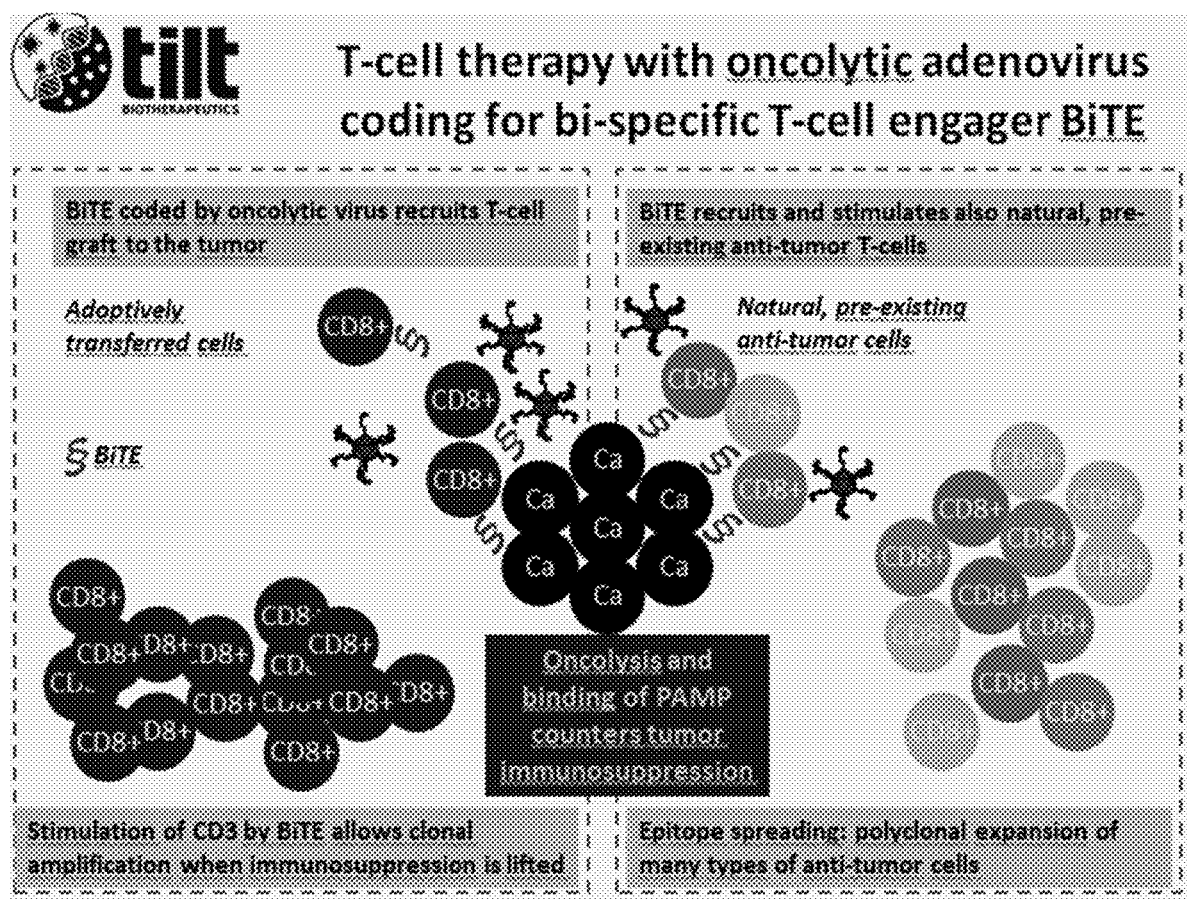
FIG. 1 shows the mechanism of action of T-cell therapy with oncolytic adenovirus coding for bi-specific T-cell engager BiTE.

One approach of the present invention is the development of a treatment for patients with cancer using the transfer of immune lymphocytes that are capable of reacting with and destroying the cancer. Isolated tumor infiltrating lymphocytes are grown in culture to large numbers and infused into the patient. In the present invention adenoviral vectors encoding at least a bispecific monoclonal antibody may be utilized for increasing the effect of lymphocytes. As used herein "increasing the efficacy of adoptive cell therapy" refers to a situation, wherein the adenoviral vector of the invention is able to cause a stronger therapeutic effect in a subject when used together with an adoptive cell therapeutic composition compared to the therapeutic effect of the adoptive cell therapeutic composition alone. FIG. 1 refers to the mechanism of increasing the efficacy by illustrating T-cell therapy with oncolytic adenovirus coding for bi-specific T-cell engager BiTE. A specific embodiment of the invention is a method of treating cancer in a subject, wherein the method comprises administration of an oncolytic adenoviral vector of the invention to a subject, said method further comprising administration of adoptive cell therapeutic composition to the subject. Adoptive cell therapeutic composition and the vectors of the invention are administered separately. Separate administrations of an adoptive cell therapeutic composition and adenoviral vectors may be preceded by myeloablating or non-myeloablating preconditioning chemotherapy and/or radiation. The adoptive cell therapy treatment is intended to reduce or eliminate cancer in the patient.

A specific embodiment of the invention relates to therapies with adenoviral vectors and an adoptive cell therapeutic composition, e.g. tumor infiltrating lymphocytes, TCR modified lymphocytes or CAR modified lymphocytes. T-cell therapies in particular, but also any other adoptive therapies such as NK cell therapies or other cell therapies may be utilized in the present invention. Indeed, according to the present invention the adoptive cell therapeutic composition may comprise unmodified cells such as in TIL therapy or genetically modified cells. There are two common ways to achieve genetic targeting of T-cells to tumor specific targets. One is transfer of a T-cell receptor with known specificity (TCR therapy) and with matched human leukocyte antigen (HLA, known as major histocompatibility complex in rodents) type. The other is modification of cells with artificial molecules such as chimeric antigen receptors (CAR). This approach is not dependent on HLA and is more flexible with regard to targeting molecules. For example, single chain antibodies can be used and CARs can also incorporate costimulatory domains. However, the targets of CAR cells need to be on the membrane of target cells, while TCR modifications can utilize intracellular targets.

As used herein "adoptive cell therapeutic composition" refers to any composition comprising cells suitable for adoptive cell transfer. In one embodiment of the invention the adoptive cell therapeutic composition comprises a cell type selected from a group consisting of a tumor infiltrating lymphocyte (TIL), TCR (i.e. heterologous T-cell receptor) modified lymphocytes and CAR (i.e. chimeric antigen receptor) modified lymphocytes. In another embodiment of the invention, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one specific embodiment of the invention the adoptive cell therapeutic composition comprises T cells. As used herein "tumor-infiltrating lymphocytes" or TILs refer to white blood cells that have left the bloodstream and migrated into a tumor. Lymphocytes can be divided into three groups including B cells, T cells and natural killer cells. In another specific embodiment of the invention the adoptive cell therapeutic composition comprises T-cells which have been modified with target-specific chimeric antigen receptors or specifically selected T-cell receptors. As used herein "T-cells"

refers to CD3+ cells, including CD4+ helper cells, CD8+ cytotoxic T-cells and γδ T cells.

In addition to suitable cells, adoptive cell therapeutic composition used in the present invention may comprise any other agents such as pharmaceutically acceptable carriers, buffers, excipients, adjuvants, additives, antiseptics, filling, stabilising and/or thickening agents, and/or any components normally found in corresponding products. Selection of suitable ingredients and appropriate manufacturing methods for formulating the compositions belongs to general knowledge of a man skilled in the art.

The adoptive cell therapeutic composition may be in any form, such as solid, semisolid or liquid form, suitable for administration. A formulation can be selected from a group consisting of, but not limited to, solutions, emulsions, suspensions, tablets, pellets and capsules. The compositions are not limited to a certain formulation, instead the composition can be formulated into any known pharmaceutically acceptable formulation. The pharmaceutical compositions may be produced by any conventional processes known in the art.

A combination of an oncolytic adenoviral vector of the invention and an adoptive cell therapeutic composition refers to use of an oncolytic adenoviral vector and an adoptive cell therapeutic composition together but as separate compositions. It is clear to a person skilled in the art that an oncolytic adenoviral vector of the present invention and an adoptive cell therapeutic composition are not used as one composition. Indeed, adenoviral vectors are not used for modifying the adoptive cells but for modifying the target tumor, so that the tumor is more amenable to the desired effects of the cellular transplant. In particular, the present invention enhances recruitment of the adoptive transplant to the tumor, and increases its activity there. In a specific embodiment of the invention oncolytic adenoviral vectors and an adoptive cell therapeutic composition of a combination are for simultaneous or sequential, in any order, administration to a subject.

Cancer

The recombinant vectors of the present invention are replication competent in tumor cells. In one embodiment of the invention the vectors are replication competent in cells, which have defects in the Rb-pathway, specifically Rb-p16 pathway. These defective cells include all tumor cells in animals and humans. As used herein "defects in the Rb-pathway" refers to mutations and/or epigenetic changes in any genes or proteins of the pathway. Due to these defects, tumor cells overexpress E2F and thus, binding of Rb by E1A CR2, that is normally needed for effective replication, is unnecessary. Further selectivity of the adenoviral vector of the present invention is mediated by the E2F promoter, which only activates in the presence of free E2F, as seen in Rb/p16 pathway defective cells. In the absence of free E2F, no transcription of E1A occurs and the virus does not replicate. Inclusion of the E2F1 promoter is important to prevent expression of E1A in normal tissues, which can cause toxicity both directly and indirectly through allowing transgene expression from the E3 promoter.

The present invention relates to approaches for treating cancer in a subject. In one embodiment of the invention, the subject is a human or an animal, specifically an animal or human patient, more specifically a human or an animal suffering from cancer.

The approach of the present invention can be used to treat any cancers or tumors, including both malignant and benign tumors, both primary tumors and metastases may be targets of the approach. In one embodiment of the invention the cancer features tumor infiltrating lymphocytes. The tools of the present invention are particularly appealing for treatment of metastatic solid tumors featuring tumor infiltrating lymphocytes. In another embodiment the T-cell graft has been modified by a tumor or tissue specific T-cell receptor of chimeric antigen receptor.

As used herein, the term "treatment" or "treating" refers to administration of at least oncolytic adenoviral vectors or at least oncolytic adenoviral vectors and adoptive cell therapeutic composition to a subject, preferably a mammal or human subject, for purposes which include not only complete cure but also prophylaxis, amelioration, or alleviation of disorders or symptoms related to a cancer or tumor. Therapeutic effect may be assessed by monitoring the symptoms of a patient, tumor markers e.g. in blood or for example a size of a tumor or the length of survival of the patient In one embodiment of the invention the cancer is selected from a group consisting of nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

Before classifying a human or animal patient as suitable for the therapy of the present invention, the clinician may examine a patient. Based on the results deviating from the normal and revealing a tumor or cancer, the clinician may suggest treatment of the present invention for a patient.

Pharmaceutical Composition

A pharmaceutical composition of the invention comprises at least one type of viral vectors of the invention. In one embodiment a pharmaceutical composition of the invention comprises an oncolytic adenoviral vector comprising a deletion of a nucleic acid sequence in the E3 region, and a nucleic acid sequence encoding a bispecific monoclonal antibody in the place of the deleted nucleic acid sequence in E3 region, wherein the bispecific monoclonal antibody comprises a single chain variable fragment (scFv) specific for a cell surface molecule and a scFv specific for a tumor antigen. Furthermore, the composition may comprise at least two, three or four different vectors. In addition to the vector, a pharmaceutical composition may also comprise other therapeutically effective agents, any other agents such as pharmaceutically acceptable carriers, buffers, excipients, adjuvants, additives, antiseptics, filling, stabilising and/or thickening agents, and/or any components normally found in corresponding products. Selection of suitable ingredients and appropriate manufacturing methods for formulating the compositions belongs to general knowledge of a man skilled in the art.

The pharmaceutical composition may be in any form, such as solid, semisolid or liquid form, suitable for administration. A formulation can be selected from a group consisting of, but not limited to, solutions, emulsions, suspensions, tablets, pellets and capsules. The compositions of the current invention are not limited to a certain formulation, instead the composition can be formulated into any known pharmaceutically acceptable formulation. The pharmaceutical compositions may be produced by any conventional processes known in the art.

In one embodiment of the invention, the viral vector or pharmaceutical composition acts as an in situ vehicle for recruitment of T-cells, enhancing their therapeutic effect and allowing their propagation at the tumor.

A pharmaceutical kit of the present invention may comprises oncolytic adenoviral vectors encoding bispecific monoclonal antibodies or an adoptive cell therapeutic composition and oncolytic adenoviral vectors coding for bispecific monoclonal antibodies. In a specific embodiment the adoptive cell therapeutic composition is formulated in a first formulation and the oncolytic adenoviral vectors are formulated in a second formulation. In another embodiment of the invention the first and the second formulations are for simultaneous or sequential, in any order, administration to a subject.

Administration

The adenoviral vector or pharmaceutical composition of the invention may be administered to any eukaryotic subject selected from a group consisting of plants, animals and human beings. In a specific embodiment of the invention, the subject is a human or an animal. An animal may be selected from a group consisting of pets, domestic animals and production animals.

Any conventional method may be used for administration of the vector or composition to a subject. The route of administration depends on the formulation or form of the composition, the disease, location of tumors, the patient, comorbidities and other factors.

In one embodiment of the invention both adenoviral vectors and adoptive cell therapeutic composition are administered to a subject. The administration(s) of adoptive cell therapeutic composition and oncolytic adenoviral vectors coding for at least one bispecific monoclonal antibody to a subject may be conducted simultaneously or consecutively, in any order. In one embodiment of the invention the oncolytic viral vectors and an adoptive cell therapeutic composition are administered separately. As used herein "separate administration" or "separate" refers to a situation, wherein adoptive cell therapeutic composition and oncolytic adenoviral vectors are two different products or compositions distinct from each other.

Only one administration of adenoviral vectors of the invention or single administrations of an adoptive cell therapeutic composition and oncolytic adenoviral vectors may have therapeutic effects. There may be any period between the administrations of oncolytic adenoviruses or between the administrations of oncolytic adenoviruses and adoptive cell therapeutic composition depending for example on the patient and type, degree or location of cancer. In one embodiment of the invention there is a time period of one minute to four weeks, specifically 1 to 10 days, more specifically 1 to five days, between the consecutive administration of adoptive cell therapeutic composition and oncolytic adenoviral vectors coding for a bispecific monoclonal antibody. Several administrations of adoptive cell therapeutic composition and oncolytic adenoviral vectors are also possible. The numbers of administration times of adoptive cell therapeutic composition and oncolytic adenoviral vectors may also be different during the treatment period. Oncolytic adenoviral vectors or pharmaceutical or adoptive cell compositions may be administered for example from 1 to 10 times in the first 2 weeks, 4 weeks, monthly or during the treatment period. In one embodiment of the invention, administration of vectors or any compositions is done three to seven times in the first 2 weeks, then at 4 weeks and then monthly. In a specific embodiment of the invention, administration is done four times in the first 2 weeks, then at 4 weeks and then monthly. The length of the treatment period may vary, and for example may last from two to 12 months or more.

In a specific embodiment of the invention an adoptive cell therapeutic composition and oncolytic adenoviral vectors are administered on the same day and thereafter oncolytic adenoviral vectors are administered every week, two weeks, three weeks or every month during a treatment period which may last for example from one to 6 or 12 months or more.

In one embodiment of the invention, the administration of oncolytic virus is conducted through an intratumoral, intra-arterial, intravenous, intrapleural, intravesicular, intracavitary or peritoneal injection, or an oral administration. Any combination of administrations is also possible. The approach can give systemic efficacy despite local injection. Adoptive cell therapeutic composition may be administered intravenously or intratumorally. In one embodiment the administration of the adoptive cell therapeutic composition and/or oncolytic viral vectors coding for at least one bispecific monoclonal antibody is conducted through an intratumoral, intra-arterial, intravenous, intrapleural, intravesicular, intracavitary or peritoneal injection, or an oral administration. In a specific embodiment of the invention TILs or T cells are administered intravenously and viral vectors intratumorally and/or intravenously. Of note, virus is delivered to the tumor separately from administration of T-cells; virus is not used to modify the T-cell graft ex vivo. In essence, the virus modifies the tumor in such a way that the T-cell graft can work better.

The effective dose of vectors depends on at least the subject in need of the treatment, tumor type, location of the tumor and stage of the tumor. The dose may vary for example from about $1\times10^8$ viral particles (VP) to about $1\times10^{14}$ VP, specifically from about $5\times10^9$ VP to about $1\times10^{13}$ VP and more specifically from about $8\times10^9$ VP to about $1\times10^{12}$ VP. In one embodiment oncolytic adenoviral vectors coding for a bispecific monoclonal antibody are administered in an amount of $1\times10^{10}$-$1\times10^{14}$ virus particles. In another embodiment of the invention the dose is in the range of about $5\times10^{10}$-$5\times10^{11}$ VP.

The amount of cells transferred will also depend on the patient, but typical amounts range from $1\times10^9$-$1\times10^{12}$ cells per injection. The number of injections also varies but typical embodiments include 1 or 2 rounds of treatment several (e.g. 2-4) weeks apart.

Any other treatment or combination of treatments may be used in addition to the therapies of the present invention. In a specific embodiment the method or use of the invention further comprises administration of concurrent or sequential radiotherapy, monoclonal antibodies, chemotherapy or other anti-cancer drugs or interventions (including surgery) to a subject.

The terms "treat" or "increase", as well as words stemming therefrom, as used herein, do not necessarily imply 100% or complete treatment or increase. Rather, there are varying degrees of which one of ordinary skill in the art recognizes as having a potential benefit or therapeutic effect. In this respect, the present inventive methods can provide any amount of increase in the efficacy of T-cell therapy or any degree of treatment or prevention of a disease.

Figure 7:
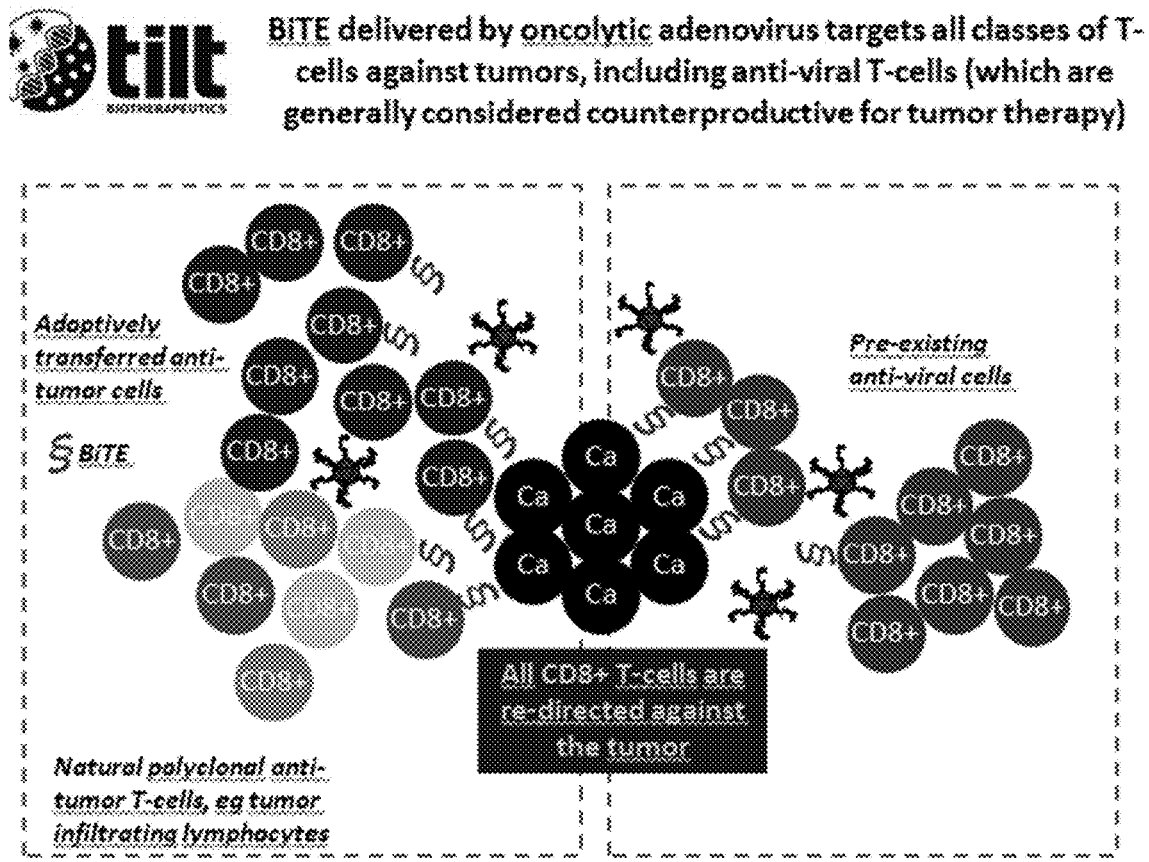
FIG. 7 reveals that BiTE delivered by oncolytic adenovirus targets all classes of T-cells against tumors, including anti-viral T-cells. In many patients, anti-viral T-cells are much more numerous than anti-tumor T-cells (Kanerva A et al. Clin Cancer Res. 2013 May 15; 19(10):2734-44). They are generally considered counterproductive in the context of tumor therapy, because a) they consume a major part of a finite amount of immune response available, and b) they can limit replication of the oncolytic virus. In contrast, our invention surprisingly takes advantage of pre-existing and induced anti-adenoviral T-cell immunity as anti-viral T-cell are targeted towards tumors (FIG. 7). As TILs of adenovirus-treated tumors contain both anti-tumor and anti-viral T-cells, CD3-scFV of BiTe will activate these T-cells regardless of their endogenous specificity (MHC I-independently). Consequently, tumor-specific killing by these T-cells is achieved by scFV specific for tumor cell surface antigen (such as mesothelin, EpCAM1, MUC1) and no off-tumor/off-target reactivity is expected to be seen. Thus, this approach redirects all CD8+ TILs (=anti-tumoral and anti-viral) into anti-tumor T-cells via binding of virus-produced BiTe.

FIGS. 1 and 7 illustrate the methods and mechanisms of the present invention.

It will be obvious to a person skilled in the art that, as the technology advances, the inventive concept can be implemented in various ways. The invention and its embodiments are not limited to the examples described above but may vary within the scope of the claims.

EXAMPLES

Materials & Methods

B16-OVA animal model: ovalbumin-expressing B16 cells (B16-OVA) were maintained in RPMI, 10% FBS, 5 mg/ml G418, 20 mM L-Glutamine, 1× Pen/Strep solution (GIBCO). 4-7-week-old C57BL/6 immunocompetent female mice were implanted subcutaneously with $2.5 \times 10^5$ B16-OVA cells in 50 ul RPMI, 0% FBS, in the right flank, one tumor per mouse. Roughly ten days post tumor implantation (when tumors became injectable, ~3 mm minimum diameter), mice were divided into groups and treated in some experiments on six consecutive days with intratumoral injections of either 50 ul PBS or $1 \times 10^9$ viral particles (VPs) of oncolytic adenovirus in 50 ul PBS. In other experiments, three injections were given on days 0, 2 and 4. As murine cells are nonpermissive to human adenovirus, multiple intratumoral virus injections were used to mimic virus replication-induced inflammation, (Blair et al., 1989).

Adoptive transfer: On the first day of the i.t. treatment, the mice also received by adoptive transfer in the intraperitoneal cavity $5 \times 10^5$ to $2 \times 10^6$ overnight-rested CD8a-enriched and expanded splenocytes from 4-8-week-old C57BL/6-Tg (TcraTcrb)1100Mjb/J (OT-1) mice, genetically engineered to have only ovalbumin (OVA)-specific CD8 T-cell receptors, in 100 ul RPMI, 0% FBS. CD8a-enrichment was performed by mouse CD8a (Ly-2) MicroBeads 5 days prior to transfer, per manufacturer's instructions (Miltenyi Biotech, USA, cat. no 130-049-401). Enriched cells were expanded in numbers for five days in lymphocyte medium (RPMI, 10% FBS, 20 mM L-Glutamine, 1× Pen/Strep solution, 15 mM HEPES, 50 µM 2-mercaptoethanol, 1 mM Na pyruvate) in the presence of recombinant murine IL-2 (160 ng/ml) and soluble anti-mouse CD3c antibody (0.3 ug/ml, Abcam, clone 145-2C11).

Tissue processing for flow cytometry: Mice were euthanized and spleens, draining lymph nodes and tumors were harvested in 1 to 10 ml RPMI, 10% FBS, and blood was collected by terminal heart bleed into the pleural cavity and transferred by disposable syringe into EDTA-containing microcentrifuge tubes, and processed for analysis: solid tissues were roughly dissociated by scalpel and triturated in a 10 ml disposable sterile pipette tip in 5 to 10 ml ACK lysing buffer (150 mM $NH_4Cl$, 10 mM $KHCO_3$, 0.1 mM EDTA, pH 7.2) and incubated at room temperature (RT) for ~20 minutes, upon which cells were pelleted at 1200 rpm 5 min+4° C., following which cells were re-suspended in 1 to 10 ml RPMI, 10% FBS, depending on the estimated amount of cells, and passed through a 40 µm sterile filter to create a single-cell solution. In some experiments, tumor tissue was instead processed directly after scalpel cutting (before addition of ACK) in 1 ml total volume of protease-cocktail (RPMI supplemented with collagenase type A, H or P, Roche, at 1 mg/ml and benzonase, 125 units/ml final conc., Sigma, E1014-25KU) for 1-2 hours at 37° C., 5% $CO_2$, after which 10 ml ACK lysing buffer was added and cells were treated as above. 200 µl whole blood was pipetted into 5 ml ACK lysing buffer and treated as above. Cells were either incubated overnight at 37° C., 5% $CO_2$, or analyzed directly by immunostaining and flow cytometry.

Tissue processing for cytokine analysis: Mice were euthanized and ~2-10 $mm^3$ tumor pieces were frozen in 2 ml microcentrifuge tubes on dry ice and stored at −80° C. Tumor pieces were weighed and 200 µl ice-cold PBS added. Pieces were homogenized by Tissue Master 125 rotor, 1× protease inhibitor cocktail (Sigma) and 0.1% BSA final conc. was added and tubes were kept on ice. Tumor homogenate was spun at 2000 rpm 10 min+4° C. and the supernatant was analyzed with CBA Flex Set cytokine beads (BD, USA) on BD FACSArray, per manufacturer's instructions.

Experiments Supporting the Invention

The experiments were carried out according to the materials and methods chapter in this disclosure and according to the experimental section described in the publication WO2014170389 (A1) and in the previously published articles (Parviainen et al. 2014, Tahtinen et al. 2015, Tahtinen et al. 2015).

Figure 2:
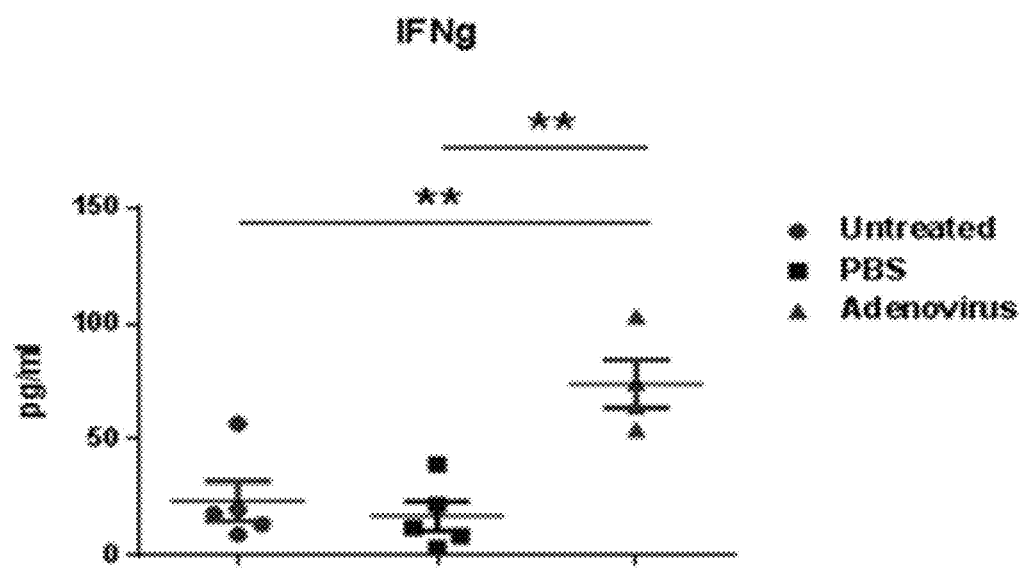
FIG. 2 shows that treatment with adenovirus induces danger signals in tumors. Treatment with 5/3 chimeric adenovirus (Ad5 based vector having fiber knob from Ad3) induces danger signals in B16.OVA tumors as demonstrated by interferon gamma expression. Binding of adenoviral pathogen-associated molecular patterns (PAMP) to toll-like receptors (TLR) on host cells can induce secretion of interferon-γ, which leads to rapid activation of innate and adaptive immune responses. Consequently, adenovirus can be used to generate an immunogenic tumor phenotype that is effectively recognized by the immune system.

Experiment 1 (Treatment with Adenovirus Induces Danger Signals in Tumors):

Treatment with Ad5/3-d24-GMCSF 5/3 chimeric adenovirus induced danger signals in B16.OVA tumors. Binding of adenoviral pathogen-associated molecular patterns (PAMP) to toll-like receptors (TLR) on host cells induce secretion of interferon-γ, associated with immune cell activation and T-cell stimulation leading to rapid activation of innate and adaptive immune responses. Consequently, adenovirus can be used to generate an immunogenic tumor phenotype that is effectively recognized by the immune system. (FIG. 2)

Figure 3:
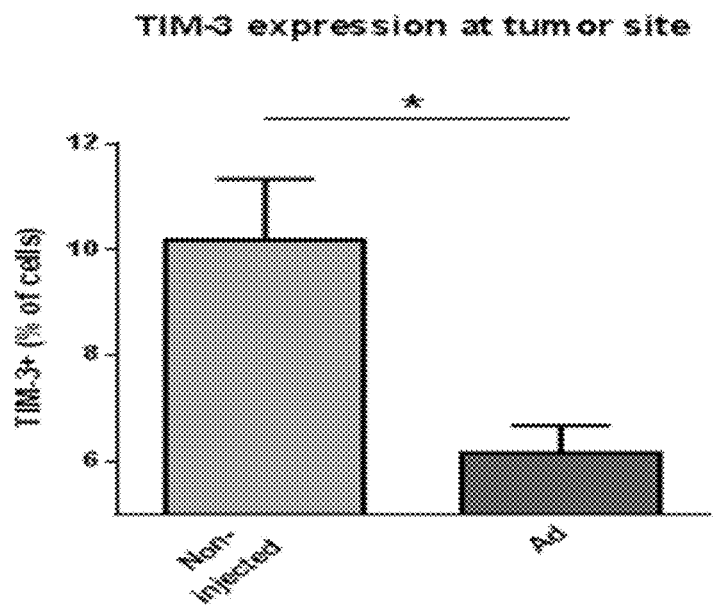
FIG. 3 shows that adenovirus has anti-immunosuppressive effects in the tumor microenvironment. 5/3 chimeric adenovirus has anti-immunosuppressive effects on B16.OVA tumor microenvironment. Tumors are highly resistant to immune attack and even high numbers of adoptively transferred tumor-specific OT-I T-cells cannot overcome tumor immunosuppression. However, if mice are simultaneously treated with 5/3 chimeric adenovirus, immunosuppressive molecules (such as TIM-3) are downregulated in the tumors.

Experiment 2 (Adenovirus has Anti-Immunosuppressive Effects in the Tumor Microenvironment):

5/3 chimeric adenovirus had anti-immunosuppressive effects on B16.OVA tumor microenvironment. Tumors were highly resistant to immune attack and even high numbers of tumor-specific OT-I T-cells did not overcome tumor immunosuppression. However, if mice were simultaneously treated with 5/3 chimeric adenovirus, immunosuppressive molecules (such as TIM-3) were downregulated in the tumors. (FIG. 3)

Figure 4:
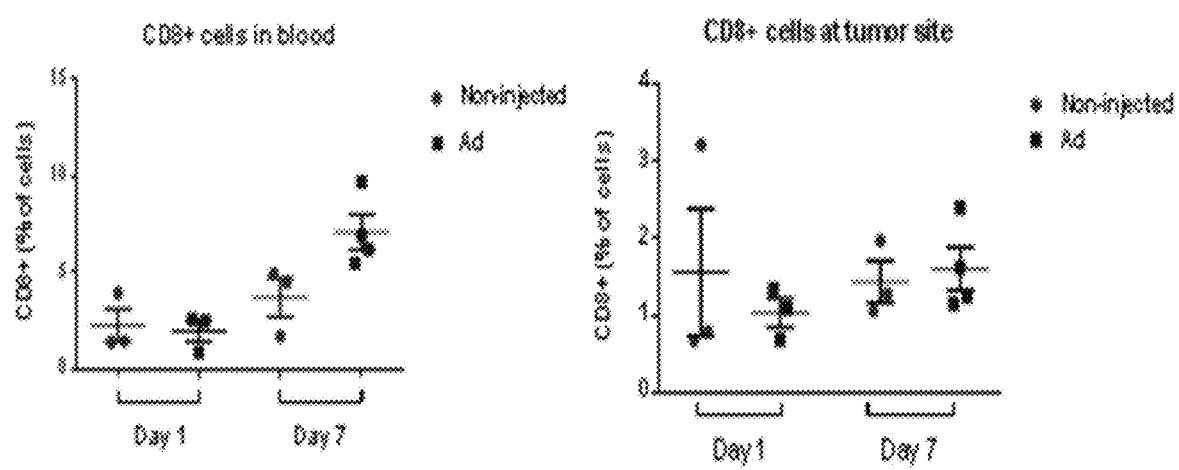
FIG. 4 reveals that lifting of immunosuppression alone is not sufficient to induce trafficking of T-cells to tumors: BiTEs are needed. Lifting of immunosuppression is not sufficient to induce trafficking of T-cells to B16.OVA tumors. Intratumoral injection of 5/3 chimeric adenovirus can induce CD8+ T-cells in peripheral blood but these cells cannot infiltrate the tumors efficiently. This poor tumor-trafficking of T-cells highlights the shortcomings of oncolytic adenovirus and adoptive T-cell therapies used as single agents, supporting the invention to enhance the trafficking of adoptively transferred T-cells by BiTe-expressing oncolytic adenovirus.

Experiment 3 (Lifting of Immunosuppression Alone is not Sufficient to Induce Trafficking of T-Cells to Tumors: BiTE are Needed):

Lifting of immunosuppression was not sufficient to induce trafficking of T-cells to B16.OVA tumors. Intratumoral injection of 5/3 chimeric adenovirus induced CD8+ T-cells in peripheral blood but these cells did not infiltrate the tumors efficiently. This poor tumor-trafficking of T-cells highlights the shortcomings of oncolytic adenovirus and adoptive T-cell therapies used as single agents, supporting the present invention to enhance the trafficking of adoptively transferred T-cells by BiTe-expressing oncolytic adenovirus. (FIG. 4)

Experiment 4 (Adenovirus is Superior to Vaccinia in Inducing Cellular Anti-Tumor Immunity; a Critical Feature for Enhancing Adoptive Cell Therapy)

Figure 5:
FIG. 5 reveals that adenovirus is superior to vaccinia in inducing cellular anti-tumor immunity; a critical feature for enhancing adoptive cell therapy. Comparison between adenovirus (Ad) and vaccinia virus (VV) immunogenicity. Levels of splenic and B16.OVA tumor-infiltrating CD8+ T-cells were higher in 5/3 chimeric adenovirus treated mice compared to mice treated with double-deleted oncolytic Western reserve vaccinia virus (this strain was used by Yu et al Mol Ther 2014). Thus, oncolytic adenovirus appears to be an ideal expression platform for BiTe due to its inherent immunogenicity, especially in context of adoptive T-cell therapy.
Figure 5:
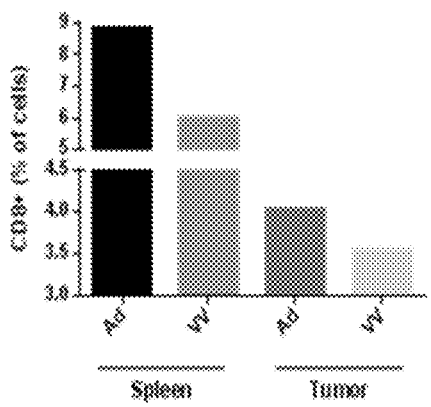

Comparison between adenovirus (Ad) and vaccinia virus (VV) immunogenicity. Levels of splenic and B16.OVA tumor-infiltrating CD8+ T-cells were higher in 5/3 chimeric adenovirus treated mice compared to mice treated with double-deleted oncolytic Western reserve vaccinia virus (this strain was used by Yu et al Mol Ther 2014). Thus, oncolytic adenovirus appears to be an ideal expression platform for BiTe due to its inherent immunogenicity, especially in context of adoptive T-cell therapy. (FIG. 5)

Experiment 5 (Adenovirus is More Effective than Vaccinia in Inducing AntiTumor Immunity)

Figure 6:
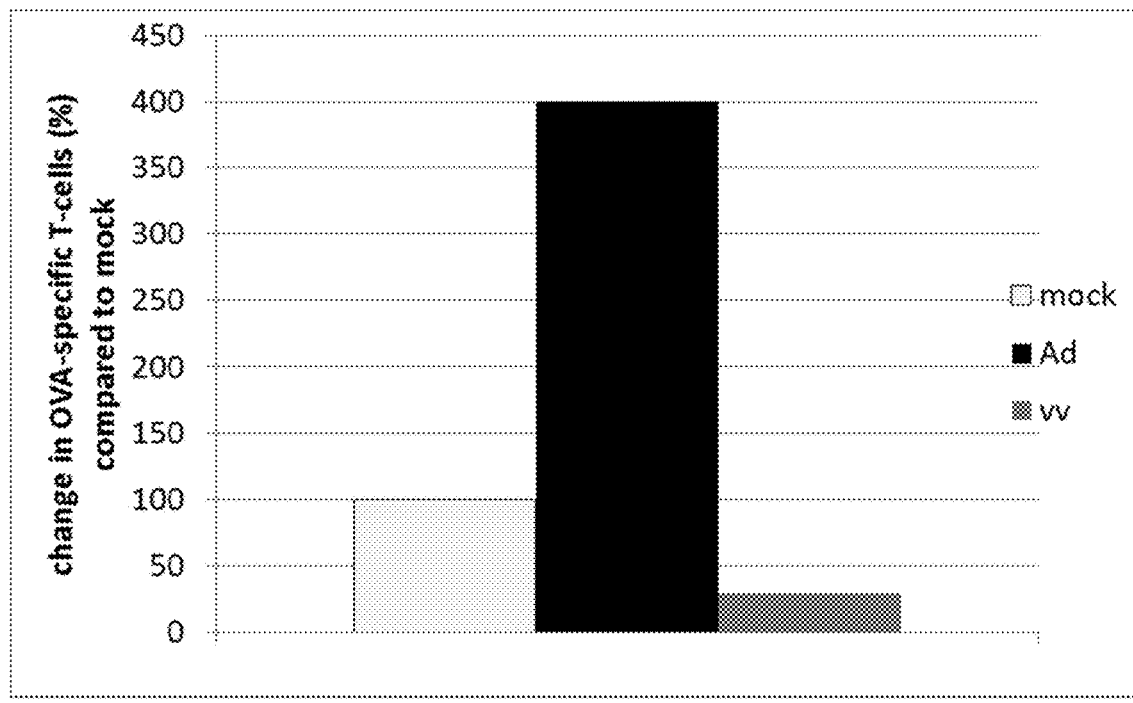
FIG. 6 shows that adenovirus is more effective than vaccinia in inducing anti-tumor immunity. Mice bearing syngeneic B16.OVA tumors were injected intratumorally with PBS, adenovirus or vaccinia virus. Tumor cell samples were stained with pentamer-APC detecting T-cell receptors specific for SIINFEKL residues of ovalbumin and assessed by flow cytometry (n=3). Data indicates change in anti-tumor T-cells following adenovirus or vaccinia virus injection; adenovirus is much more effective in inducing anti-tumor immunity while vaccinia was in fact immune suppressive in the context of anti-tumor T-cells.

Mice bearing syngeneic B16.OVA tumors were injected intratumorally with PBS, adenovirus or vaccinia virus. Tumors cell samples were stained with pentamer-APC detecting T-cell receptors specific for SIINFEKL residues of ovalbumin and assessed by flow cytometry (n=3). Data indicated change in anti-tumor T-cells following adenovirus or vaccinia virus injection; adenovirus was much more effective in inducing anti-tumor immunity. (FIG. 6)

Experiment 6 (BiTE Delivered by Oncolytic Adenovirus Targets all Classes of T-Cells Against Tumors, Including Anti-Viral T-Cells (which are Generally Considered Counterproductive for Tumor Therapy))

In addition, the present invention utilizes the extensive pre-existing Ad5 T-cell immunity in human populations that usually limits the clinical utility of adenoviral vectors. As TILs of adenovirus-treated tumors contain both anti-tumor and anti-viral T-cells, CD3-scFV of BiTe will activate these T-cells regardless of their endogenous specificity (MHC I-independently). Consequently, tumor-specific killing by these T-cells is achieved by scFV specific for tumor cell surface antigen (such as mesothelin, EpCAM1, MUC1) and no off-tumor/off-target reactivity is expected to be seen. Thus, this approach re-directs all CD8+ TILs (=anti-tumoral and anti-viral) into anti-tumor T-cells via binding of virus-produced BiTe. (FIG. 7)

Experiment 7 (Oncolytic Adenovirus, but not Non-Replicating Adenovirus, Coding for Functional Antibody Results in Efficient Antibody Production and Release from Cancer Cells)

Figure 8:
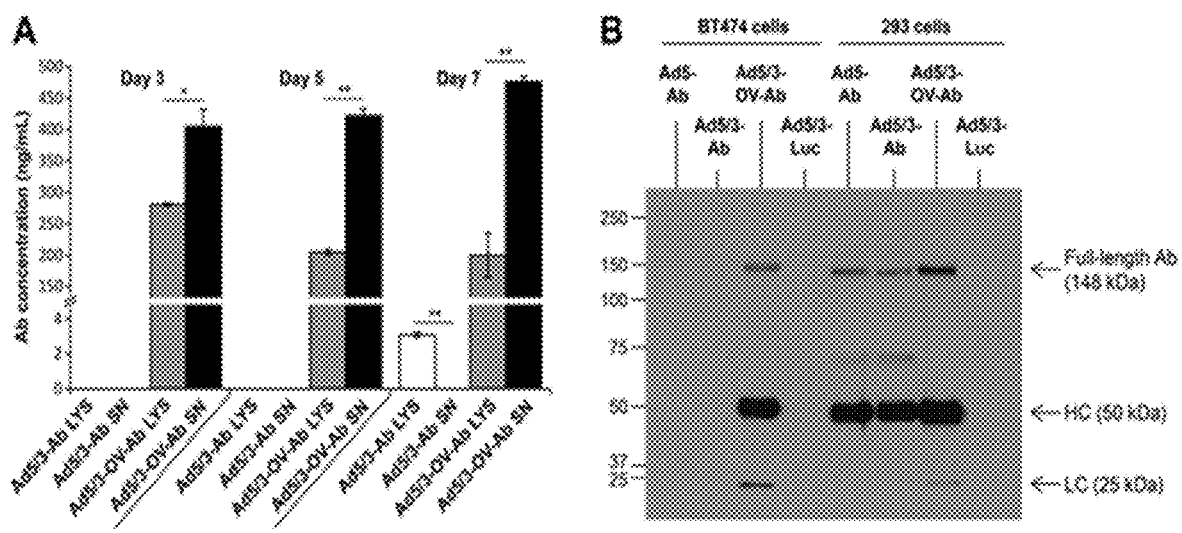
FIG. 8 shows that oncolytic adenovirus, but not non-replicating adenovirus, coding for functional antibody results in efficient antibody production and release from cancer cells. Cells were infected with indicated adenoviruses at 100 virus particles (VP)/cell, and several days later analyzed for antibody expression by human IgG ELISA (A) or Western blot (B). At each indicated time point after infection, (A) oncolytic virus Ad5/3-OV-Ab (grey and black bars) showed high production of functional antibody from ovarian cancer SKOV-3 cells: Antibody levels decreased in cell lysate (LYS) during progressive infection and cancer cell killing, and showed significant accumulation in the supernatant (SN). In contrast, non-replicating virus Ad5/3-Ab failed to produce detectable antibody in the supernatant, even though cell lysate showed evidence of antibody at day 7 post-infection (white bars). Of note, non-replicating Ad5/3-Ab virus treated cells were viable throughout the experiment, indicating the lack of active antibody secretion by cancer cells. (B) Supernatant of breast cancer BT-474 cells (left) and human embryonic 293 cells (right) was analyzed by Western blot 6 days after infection with indicated viruses. Under reducing conditions, heavy-chain (HC), light-chain (LC), and the full-length antibody produced by the oncolytic virus Ad5/3-OV-Ab were visualized in supernatant of both cell lines, whereas non-replicating Ad5-Ab and Ad5/3-Ab viruses failed to show antibody release from BT-474 cells that do not allow their replication. To confirm antibody expression by the non-replicating viruses, we used human embryonic 293 cells (right), which allow replication of also E1A-deleted adenoviruses, followed by cell lysis and release of the antibody, readily detected by Western blot. A non-replicating control virus Ad5/3-Luc coding for luciferase was used as a negative control. HC and LC were detected using polyclonal goat anti-human IgG and donkey anti-goat IgG-HRP antibodies, respectively. The antibody affinity was lower to the LC than to the HC resulting in a weaker signal. Bars represent the mean±SEM. **, P<0.01; *, P<0.05; all Student's T tests.

SKOV-3, BT-474 and 293 cells were infected with indicated adenoviruses at 100 virus particles (VP)/cell, and several days later analyzed for antibody expression by human IgG ELISA (A) or Western blot (B). At each indicated time point after infection, (A) oncolytic virus Ad5/3-d24-Trastuzumab (grey and black bars) showed high production of functional antibody from ovarian cancer SKOV-3 cells: Antibody levels decreased in cell lysate (LYS) during progressive infection and cancer cell killing, and showed significant accumulation in the supernatant (SN). (OV refers to Ad5/3-d24 and Ab refers to antibody Trastuzumab) In contrast, non-replicating virus Ad5/3-Ab failed to produce detectable antibody in the supernatant, even though cell lysate showed evidence of antibody at day 7 post-infection (white bars). Of note, non-replicating Ad5/3-Ab virus treated cells were viable throughout the experiment, indicating the lack of active antibody secretion by cancer cells. (B) Supernatant of breast cancer BT-474 cells (left) and human embryonic 293 cells (right) was analyzed by Western blot 6 days after infection with indicated viruses. Under reducing conditions, heavy-chain (HC), light-chain (LC), and the full-length antibody produced by the oncolytic virus Ad5/3-OV-Ab were visualized in supernatant of both cell lines, whereas non-replicating Ad5-Ab and Ad5/3-Ab viruses failed to show antibody release from BTB-474 cells that do not allow their replication. To confirm antibody expression by the non-replicating viruses, we used human embryonic 293 cells (right), which allow replication of also E1A-deleted adenoviruses, followed by cell lysis and release of the antibody, readily detected by Western blot. A non-replicating control virus Ad5/3-Luc coding for luciferase was used as a negative control. HC and LC were detected using polyclonal goat anti-human IgG and donkey anti-goat IgG-HRP antibodies, respectively. The antibody affinity was lower to the LC than to the HC resulting in a weaker signal. Bars represent the mean±SEM. **, P<0.01; *, P<0.05; all Student's T tests. (FIG. 8)

Experiment 8 (Oncolytic Adenovirus Coding for Antibody Shows Higher Intratumoral while Lower Systemic Antibody Levels than after Systemic Antibody Treatment)

Figure 9:
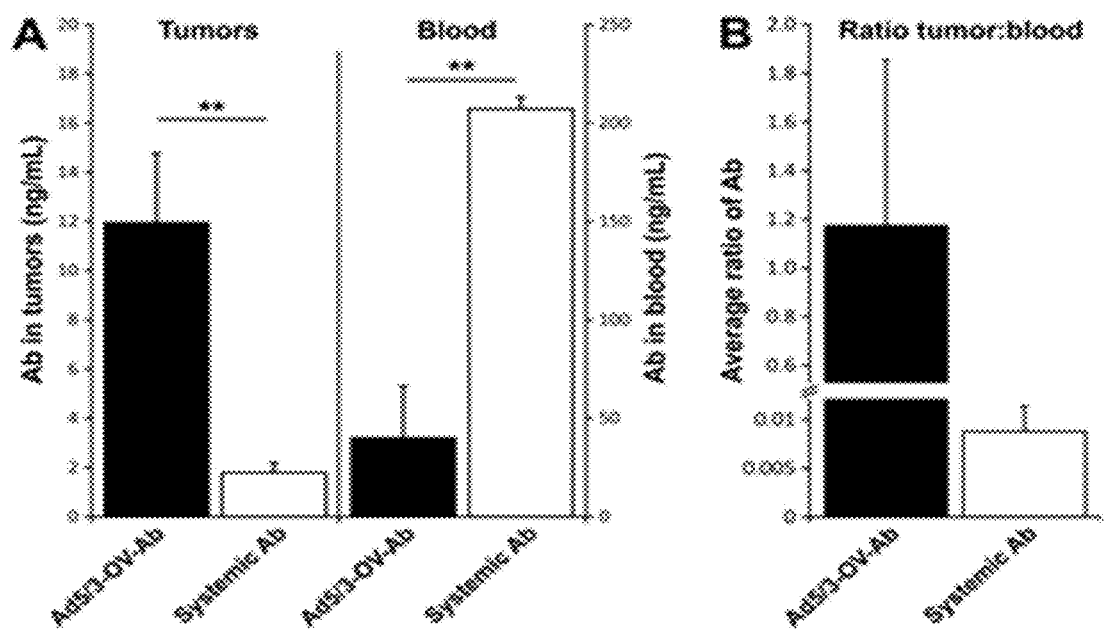
FIG. 9 shows that oncolytic adenovirus coding for antibody shows higher intratumoral while lower systemic antibody levels than after systemic antibody treatment. Subcutaneous N87 gastric cancer xenograft bearing nude/NMRI mice (n=5 per group) were treated with intratumoral injections of oncolytic Ad5/3-OV-Ab virus ($2 \times 10^8$ VP/tumor) or intraperitoneal injections of commercial antibody (Ab; 0.3 µg/g) on days 0, 4, 8, and 15. Health of the animals was monitored and tumors and blood samples were collected from mice sacrificed on days 32 and 40 (systemic Ab), day 46 (systemic Ab and Ad5/3-OV-Ab virus), and day 50 (Ad5/3-OV-Ab virus). A) Endpoint tumors and blood samples were measured by human IgG ELISA to assess the antibody concentration: Ad5/3-OV-Ab treated mice sacrificed on days 46 and 50 post-treatment showed still significantly higher antibody concentrations in tumors (P<0.001, left), while presenting much lower circulating levels (P<0.001, right), as compared to systemic Ab treated mice that were sacrificed earlier on days 32, 40 and 46. B) Antibody levels in tumor and blood samples of each individual animal were compared to assess the antibody distribution. The average ratio of antibody in tumor versus blood was above 1.0 in mice treated with Ad5/3-OV-Ab virus, whereas systemic Ab treatment resulted in very low ratio of less than 0.01. Thus, treatment with antibody expressing oncolytic virus can achieve improved intratumoral antibody concentration, while significantly reducing systemic exposure in animals. Notably, most of the virus-treated mice survived longer (up to 50 days) and therefore showed evidence of sustained local antibody production. Error bars represent the mean+SEM. **, P<0.01, Student's T test.

Subcutaneous N87 gastric cancer (Park et al. 1990) xenograft bearing nude/NMRI mice (n=5 per group) were treated with intratumoral injections of oncolytic Ad5/3-OV-Ab virus ($2 \times 10^8$ VP/tumor) or intraperitoneal injections of commercial antibody (Ab; 0.3 µg/g) on days 0, 4, 8, and 15. Health of the animals was monitored and tumors and blood samples were collected from mice sacrificed on days 32 and 40 (systemic Ab), day 46 (systemic Ab and Ad5/3-OV-Ab virus), and day 50 (Ad5/3-OV-Ab virus). A) Endpoint tumors and blood samples were measured by human IgG ELISA to assess the antibody concentration: Ad5/3-OV-Ab treated mice sacrificed on days 46 and 50 post-treatment showed still significantly higher antibody concentrations in tumors (P<0.001, left), while presenting much lower circulating levels (P<0.001, right), as compared to systemic Ab treated mice that were sacrificed earlier on days 32, 40 and 46. B) Antibody levels in tumor and blood samples of each individual animal were compared to assess the antibody distribution. The average ratio of antibody in tumor versus blood was above 1.0 in mice treated with Ad5/3-OV-Ab virus, whereas systemic Ab treatment resulted in very low ratio of less than 0.01. Thus, treatment with antibody expressing oncolytic virus can achieve improved intratumoral antibody concentration, while significantly reducing systemic exposure in animals. Notably, most of the virus-treated mice survived longer (up to 50 days) and therefore showed evidence of sustained local antibody production. Error bars represent the mean+SEM. , P<0.01, Student's T test. (FIG. 9**)

Experiment 9 (Expression of T-Cell Exhaustion Marker and Immunosuppressive Receptor TIM3 Decreases after Oncolytic Adenovirus Treatment and Correlates with Improved Survival)

Figure 10:
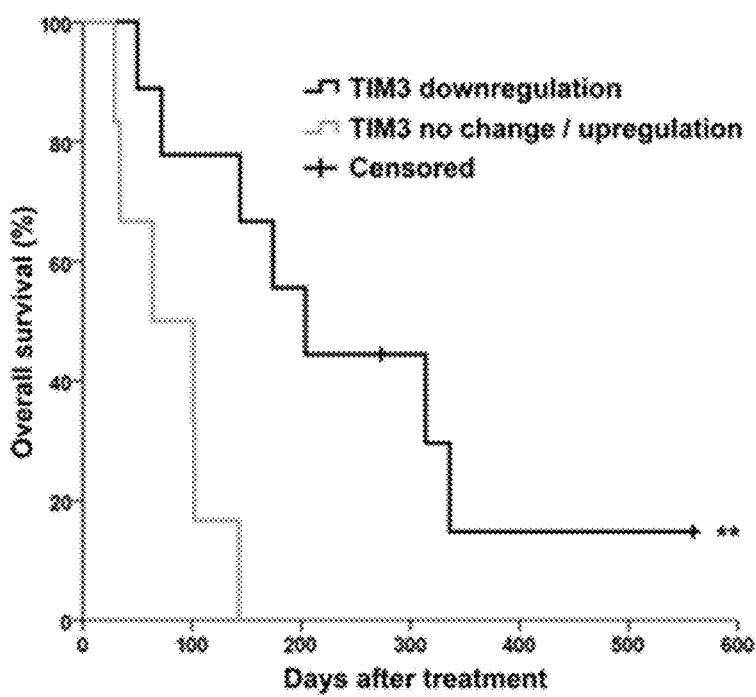
FIG. 10 shows that expression of T-cell exhaustion marker and immunosuppressive receptor TIM3 decreases after oncolytic adenovirus treatment and correlates with improved survival. 15 patients with advanced solid tumors were treated with oncolytic adenoviruses in the context of an Advanced Therapy Access Program. Baseline and post-treatment tumor biopsies were analyzed by RNA microarray (HumanHT-12 v4 Expression BeadChips array, Illumina), and gene expression levels were compared to identify differentially expressed genes. T-cell immunoglobulin mucin-3 (TIM3), which is an exhaustion marker and negative regulator of both innate and adaptive immune responses in tumors, was among the top differentially expressed genes: TIM3 showed major downregulation in 5 patients (change over 1.0, A[log 2]) and minor decrease in 4 patients (average change of 0.38, A[log 2]). Meanwhile, 6 patients failed to show downregulation of TIM3, out of which two patients showed upregulation post-treatment. When overall survival was compared between these groups, the patients with TIM3 downregulation (n=9) showed significantly improved survival (P=0.004, Log-rank test) over the patients with "TIM3 no change/upregulation" (n=6). Median survival was 204 days and 64 days in TIM3 down- and upregulation groups, respectively. Thus, two-thirds of oncolytic adenovirus treatments seemed to result in decrease of immunosuppressive receptor and exhaustion marker TIM3, which strongly correlated with prolonged overall survival.

15 patients with advanced solid tumors were treated with oncolytic adenoviruses in the context of an Advanced Therapy Access Program (Taipale et al. 2016). Baseline and post-treatment tumor biopsies were analyzed by RNA microarray (HumanHT-12 v4 Expression BeadChips array, Illumina), and gene expression levels were compared to identify differentially expressed genes. T-cell immunoglobulin mucin-3 (TIM3), which is an exhaustion marker and negative regulator of both innate and adaptive immune responses in tumors, was among the top differentially expressed genes: TIM3 showed major downregulation in 5 patients (change over 1.0, A[log 2]) and minor decrease in 4 patients (average change of 0.38, A[log 2]). Meanwhile, 6 patients failed to show downregulation of TIM3, out of which two patients showed upregulation post-treatment. When overall survival was compared between these groups, the patients with TIM3 downregulation (n=9) showed significantly improved survival (P=0.004, Log-rank test) over the patients with "TIM3 no change/upregulation" (n=6). Median survival was 204 days and 64 days in TIM3 down- and upregulation groups, respectively. Thus, two-thirds of oncolytic adenovirus treatments seemed to result in decrease of immunosuppressive receptor and exhaustion marker TIM3, which strongly correlated with prolonged overall survival. (FIG. 10)

Experiment 10 (Improved In Vitro Cell Killing with TIL and Oncolytic Adenovirus Combination)

Figure 11:
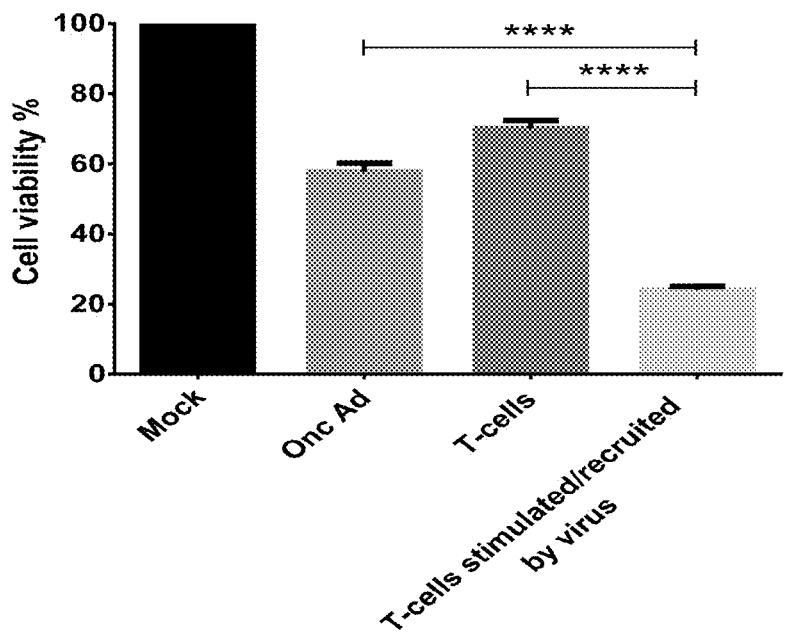
FIG. 11 shows improved in vitro cell killing with TIL and oncolytic adenovirus combination. HapT1 cells were infected with oncolytic adenovirus (100 VP/cell) for 3 days before adding HapT1 TIL. Target cell viability was determined 24 hours after TIL addition. Error bars, SE. ****p<0.0001. The best killing was seen when T-cells were stimulated with an oncolytic adenovirus.

HapT1 cells were infected with oncolytic adenovirus Ad5/3-d24 (100 VP/cell) for 3 days before adding HapT1 TIL. Target cell viability was determined 24 hours after TIL addition. Error bars, SE. ****p<0.0001. The best killing was seen when T-cells were stimulated with an oncolytic adenovirus. (FIG. 11)

Experiment 11 (in the Absence of BiTe Molecules, TILs Extracted from HapT1 Tumors Don't have an Additive Effect on Target Cell Killing when Combined with Oncolytic Adenoviruses)

Figure 12:
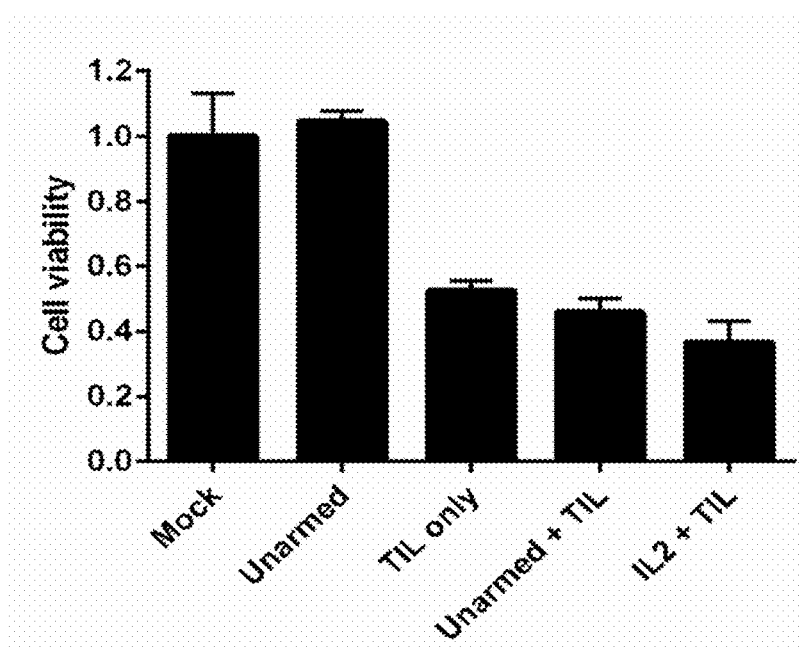
FIG. 12 show that in the absence of BiTe molecules, TILs extracted from HapT1 tumors don't have an additive effect on target cell killing when combined with oncolytic adenoviruses. HapT1 cells were plated on 96 well plate and incubated five days with oncolytic adenovirus Ad5/3-E2F-d24 only or armed with human IL-2. TILs extracted from established HapT1 tumors were added to cells 10:1 24 h before measuring the viability of the cells with MTS assay. Synergy was not observed between viruses and TILs.

HapT1 cells were plated on 96 well plate and incubated five days with oncolytic adenovirus Ad5/3-E2F-d24 only or armed with human IL-2. TILs extracted from established HapT1 tumors were added to cells 10:1 24 h before measuring the viability of the cells with MTS assay. Synergy was not observed between viruses and TILs. (FIG. 12)

Experiment 12 (Excellent Lytic Activity of a Combination Virus+BiTE+PBMCs)

Figure 13A:
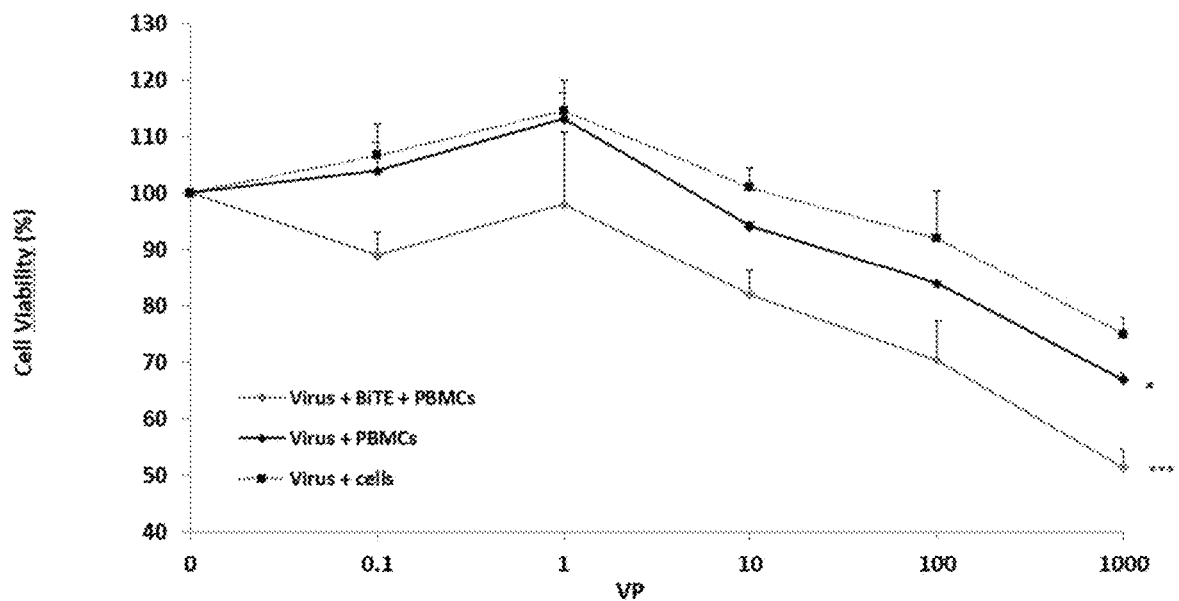
FIG. 13A: a) SW480 tumor cells were infected with increasing VPs (0.01, 0.1, 1, 10, 100, 1000 VP) of Ad 5/3-E2F-d24-E3 virus and with 10 ng of BiTE. Effector cells (PBMCs) were added at an effector to target ratio of 5:1. MTS assay was used to determine the cell viability at 48 hours post infection. Error bars indicate SEM of triplicate measurements. Virus+Cells Vs Virus+PBMCs *P=0.0184, Virus+Cells Vs Virus+PBMCs+BiTE *** P=0.001.
Figure 13B:
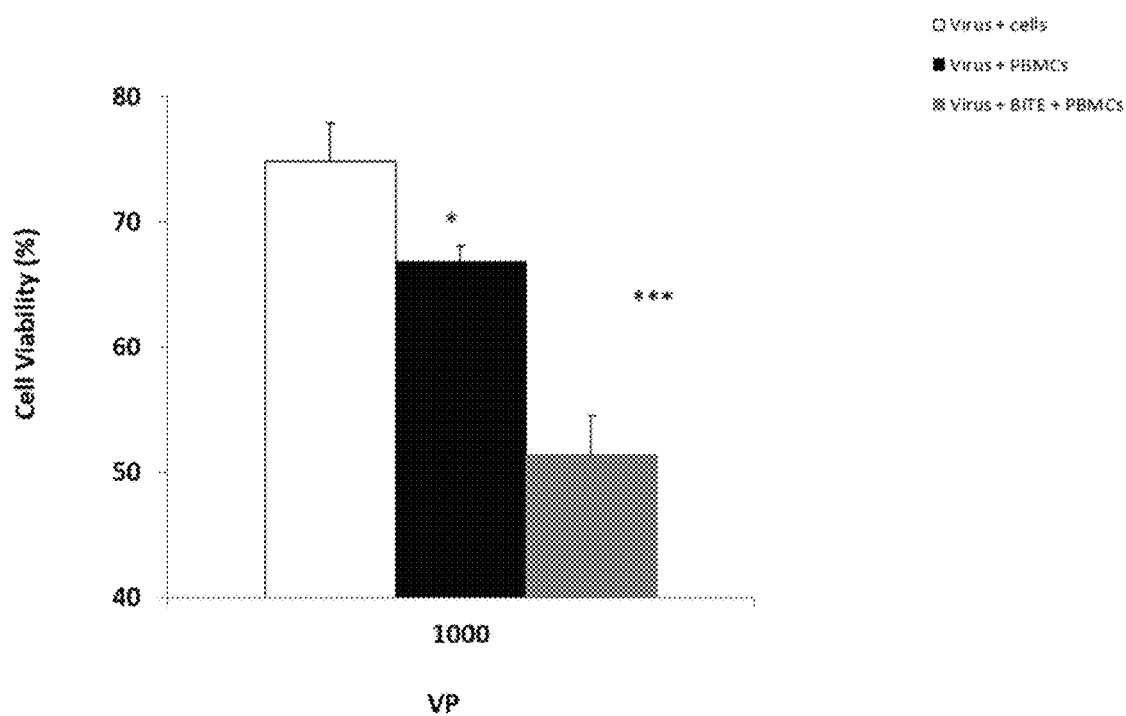
FIG. 13B: a) SW480 tumor cells were infected with 1000 VP of Ad 5/3-E2F-d24-E3 virus and with 10 ng of BiTE. Effector cells (PBMCs) were added at an effector to target ratio of 5:1. MTS assay was used to determine the cell viability at 48 hours post infection. Error bars indicate SEM of triplicate measurements. Virus+Cells Vs Virus+PBMCs *P=0.0184, Virus+Cells Vs Virus+BiTE+PBMCs ***P=0.001.

SW480 tumor cells were seeded on 96 well plate, 10 000 cells/well, and incubated for 24 h. The cells are infected with Ad 5/3-E2F-d24-E3 virus, 0.01, 0.1, 1, 10, 100 and 1000 viral particles per cell and 10 ng of human CD3 specific EpCAM targeted BiTE (Antihuman EpCam, Cat#CABT-33295MH) at least in three replicates, 50 ul/well in assay media (L-15, 2% FBS, 2 mM L-glutamine, 100 U/ml penicillin, and 100 µg/ml streptomycin). Effector cells (PBMCs) were added at an effector to target ratio of 5:1. Next day, 50 ul 10% L-15 was added to cells. 48 h after infection the infection media was replaced with 100 ul growth media containing 10% CellTiter 96 AQueous One Solution (Promega, Madison, Wis., USA) and incubated for two hours. The absorbance was read at 490 nm. Error bars indicate SEM of triplicate measurements. Virus+Cells Vs Virus+PBMCs *P=0.0184, Virus+Cells Vs Virus+PBMCs+BiTE *** P=0.001 (FIG. 13A). FIG. 13B: SW480 tumor cells were infected with 1000 VP of Ad 5/3-E2F-d24-E3 virus and with 10 ng of BiTE. Effector cells (PBMCs) were added at an effector to target ratio of 5:1. MTS assay was used to determine the cell viability at 48 hours post infection. Error bars indicate SEM of triplicate measurements. Virus+Cells Vs Virus+PBMCs *P=0.0184, Virus+Cells Vs Virus+BiTE+PBMCs ***P=0.001.

Fractional Product Method:

Fractional Product Method was used to assess synergy, this method is derived from a method originally developed by Webb (Webb J, 1963).

$$\text{Formula} = \frac{\text{Expected Values (Product of } Monotherapies\text{)} =}{\text{Observed Values (Virus} + PBMCs + BiTE\text{)}}$$

$$\frac{(\text{Virus} + \text{Cells})(\text{Virus} + PBMCs + \text{Cells})}{\text{Observed Values (Virus} + PBMCs + BiTE\text{)}}$$

0, 1 $VP$ = 1.245 = synergistic

1 $VP$ = 1.32 = synergistic

10 $VP$ = 1.2 = synergistic

100 $VP$ = 1.1 = synergistic

1000 $VP$ = 1.1 = synergistic

Key:
 Synergistic=Ratio greater than 1
 Additive Effect=equal to 1
 Antagonism=less than 1

Results:

These findings indicate that BiTE are synergistic with TILT's oncolytic adenovirus.

Experiment 13 (In Vitro Cell Viability Experiment Combining Ad-BiTE and OT1 T-Cells on B16-OVA Target Cells)

B16-OVA cells are plated on 96-well plates at 1×10e4 cells/well and infected with 100 VP/cell of Ad-BiTE, T-cells (2:1 effector to target ratio) or both. Cell viability is determined 24 hours later by MTS assay.

Experiment 14 (Adenovirus or Adenovirus Armed with IL2 is not Enough to Accumulate T-Cells at Tumors)

Figure 14:
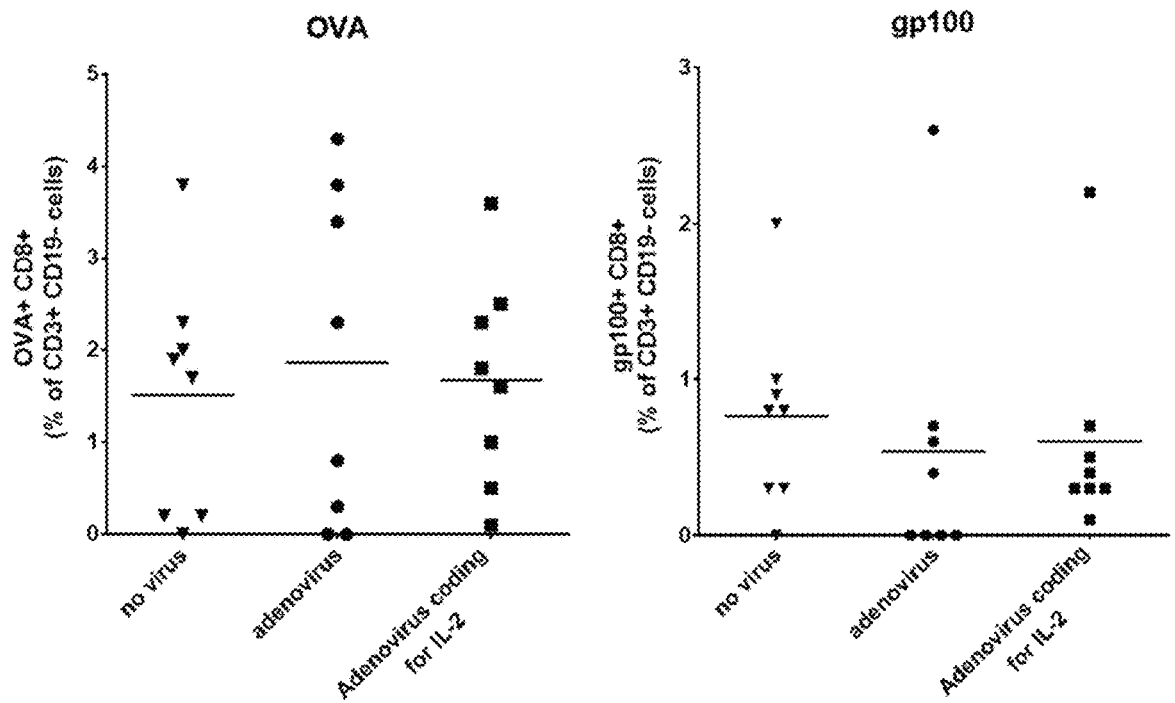
FIG. 14 shows that adenovirus or adenovirus armed with IL2 is not enough to accumulate T-cells at tumors. Adenovirus treatment combined with adoptive T-cell transfer results in suboptimal T-cell infiltration into B16.OVA melanoma tumors. Tumors collected 18 days after treatment start were flow cytometrically analyzed for ovalbumin-specific CD8+ T-cells (OVA) and gp100-specific CD8+ T-cells. OVA and gp100 are epitopes expressed on melanoma cells. Differences between different treatment groups were not statistically significant, and not different from T-cell therapy alone (no virus). Horizontal lines, mean values.

Adenovirus treatment was combined with adoptive T-cell transfer and resulted in suboptimal T-cell infiltration into B16.OVA melanoma tumors. Tumors collected 18 days after treatment start were flow cytometrically analyzed for ovalbumin-specific CD8+ T-cells (OVA) and gp100-specific CD8+ T-cells. OVA and gp100 are epitopes expressed on melanoma cells. Differences between different treatment groups were not statistically significant, and not different from T-cell therapy alone (no virus). Horizontal lines, mean values. (FIG. 14)

Experiment 15 (Oncolytic Adenoviruses are Unable to Recruit Cytotoxic CD8+ T Cells to Tumors)

Figure 15:
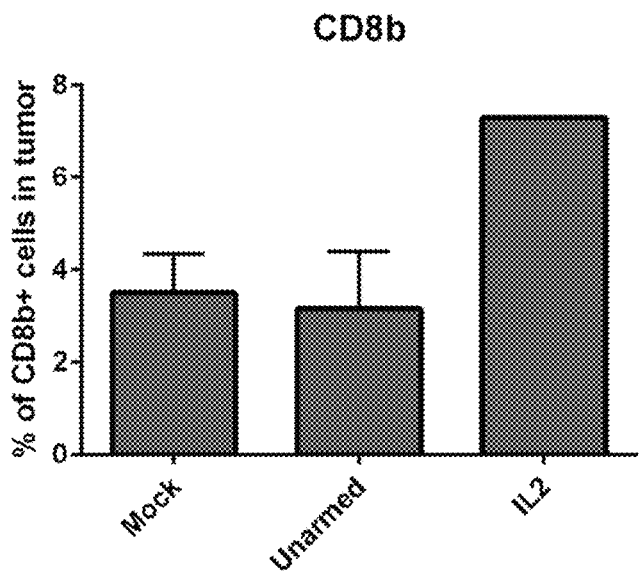
FIG. 15 reveals cytotoxic T cells in hamster pancreatic tumors. Oncolytic adenoviruses are unable to recruit cytotoxic CD8+ T cells to tumors. Subcutaneous hamster pancreatic tumors (HapT1) were treated with oncolytic adenoviruses Ad5/3-E2F-d24 alone or armed with human IL-2 five times in total during 19 days. On day 25 the animals were sacrificed and tumor cells labeled with cross-reactive anti-rat CD8b PE antibody. (Sample numbers: mock and unarmed n=5, IL2 n=1). Oncolytic adenovirus alone was not able to recruit Cd8 cells to the tumor. IL2 seemed more promising but the increase was not significant.

Subcutaneous hamster pancreatic tumors (HapT1) were treated with oncolytic adenoviruses Ad5/3-E2F-d24 alone or armed with human IL-2 five times in total during 19 days. On day 25 the animals were sacrificed and tumor cells labeled with cross-reactive anti-rat CD8b PE antibody. (Sample numbers: mock and unarmed n=5, IL2 n=1). Oncolytic adenovirus alone was not able to recruit Cd8 cells to the tumor. IL2 seemed more promising but the increase was not significant. (FIG. 15)

Experiment 16 (Rechallenge in Immunocompetent Hamsters)

Figure 16:
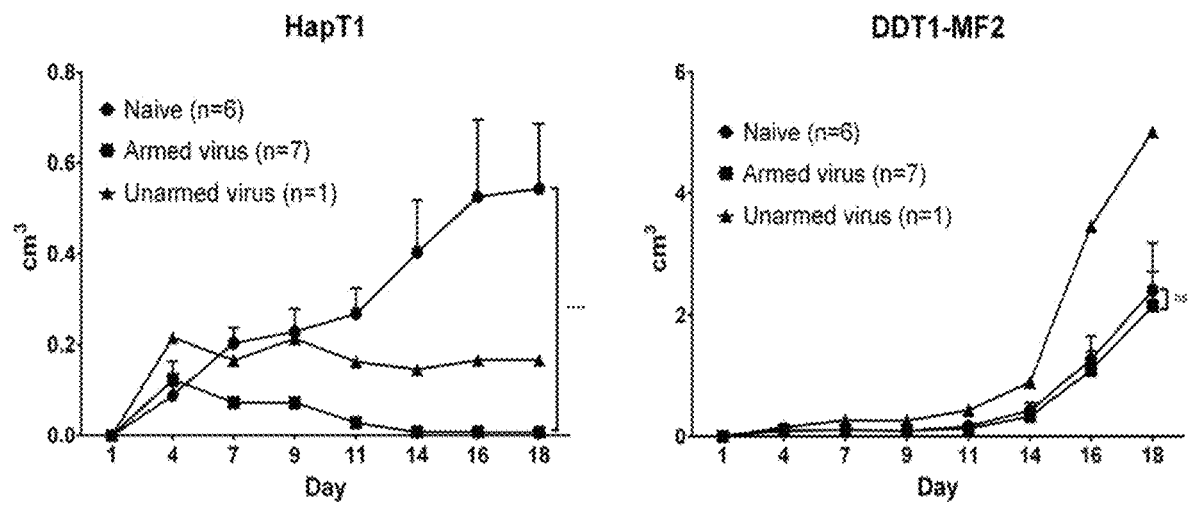
FIG. 16 shows results of rechallenge in immunocompetent hamsters. Hamsters previously cured with an unarmed oncolytic adenovirus Ad5/3-E2F-d24 or with adenovirus armed with a cytokine (TNFα, IL-2 or both) treatment resisted same tumor type (HapT1) but not different one (DDT1-MF2). Naïve animals which had not encountered either of the cell lines previously were used as a control.

Hamsters previously cured with an unarmed oncolytic adenovirus Ad5/3-E2F-d24 or with adenovirus armed with a cytokine (TNFα, IL-2 or both) treatment resisted same tumor type (HapT1) but not different one (DDT1-MF2). Naïve animals which had not encountered either of the cell lines previously were used as a control. Arming the virus with a molecule able to induce anti-tumor immunity (for example BITe) is necessary for inducing protective immunity (=a sign of memory response against tumor epitopes). (FIG. 16)

Experiment 17 (In Vivo Efficacy of Armed or Unarmed Oncolytic Adenovirus, with or without T-Cell Therapy)

Established HapT1 tumors were injected intratumorally with oncolytic adenovirus Ad5/3-d25 (1×10$^7$ VP/tumor) on Days 1 and 8. On Day 2, HapT1 tumor infiltrating lymphocytes grown ex vivo (1.5×10$^6$ TIL/tumor) were administered intratumorally. Error bars, SE. *p<0.05, **p<0.01. The best anti-tumor efficacy was seen when tumors were treated with an oncolytic virus (such as a BiTe coding virus) and TILs were also given. (FIG. 17)

Experiment 18 (Hypothetical Results from In Vivo Antitumor Efficacy Experiment Combining Ad-BiTE and OT1 T-Cell Transfer in Immunocompetent Mice Bearing B16-OVA Tumors)

Subcutaneously implanted B16-OVA tumors (0.25×10e6 cells/tumor) will be treated with a single intraperitoneal injection of CD8-enriched OT1 T-cells, intratumoral injection of Ad-BiTE (1×10e9 VP/tumor) or both. Virus injections will be repeated every 7 days. (FIG. 18)

Experiment 19 (Adenoviral Delivery of Cytokines IL2 and TNFa Enhance Efficacy of Adoptive Cell Therapy: Rationale for Including Cytokines in Oncolytic Adenovirus Coding for BiTE)

B16-OVA tumor-bearing C57 mice were treated intratumorally with 1×10e9 viral particles of armed adenoviruses and intraperitoneally with 1.5×10e6 CD8-enriched OT-1 T-cells on Day 1. Virus treatments continued every 7 days. (FIG. 19)

Experiment 20 (Novel Virus Constructs)

We generated new oncolytic Ad5/3 adenoviruses carrying the following backbone: Ad5/3-E2F-D24-transgene. Transgenes were in the area of deleted E3 gp19k/6.7k. Following transgenes were utilized in the vectors:

aMesothelin-aCD3
aEpCAM-aCD3
aMUC1-aCD3
aMesothelin-aCD3-IRES-IL2
aMesothelin-aCD3-IRES-TNFa
aEpCAM-aCD3-IRES-IL2
aEpCAM-aCD3-IRES-TNFa
aMUC1-aCD3-IRES-IL2
aMUC1-aCD3-IRES-TNFa (FIGS. 20 and 21)

The adenoviral vectors of FIG. 20 or construct maps of FIG. 21 comprise nucleotide sequences comprising e.g. transgenes aMesothelin-aCD3 (SEQ ID NO: 9), aEpCAM-aCD3 (SEQ ID NO: 4) or aMUC1-aCD3 (SEQ ID NO: 8), listed in Table 2. Nucleotide sequence of the viral vector of the present invention comprises or consists of e.g. SEQ ID NOs: 1, 2, 3, 5, 6, 9 (aMesothelin-aCD3-IRES-IL2); SEQ ID NOs: 1, 2, 3, 5, 6, 7 (aMesothelin-aCD3-IRES-TNFa); SEQ ID NOs: 1, 2, 3, 4, 5, 6 (aEpCAM-aCD3-IRES-IL2); SEQ ID NOs: 1, 2, 3, 4, 5, 7 (aEpCAM-aCD3-IRES-TNFa); SEQ ID NOs: 1, 2, 3, 5, 6, 8 (aMUC1-aCD3-IRES-IL2); SEQ ID NOs: 1, 2, 3, 5, 7, 8 (aMUC1-aCD3-IRES-TNFa). The adenoviral vectors were constructed according to the sequences listed in Table 2. General methods for constructing adenoviral vectors, also utilized for the present invention, are well known to a person skilled in the art and are described e.g. in Koski et al. 2010, Hemminki et al. 2015.

TABLE 2

Sequence listing.

| SEQ ID NO: | Name |
|---|---|
| 1 | LITR |
| 2 | E2F |
| 3 | D24 |
| 4 | Transgene EpCAM_CD3linker |
| 5 | 5/3 knob modification |
| 6 | Transgene IRES-IL2 |
| 7 | Transgene IRES-TNFa |
| 8 | Transgene MUC1_CD3linker |
| 9 | Transgene AntiMesothelin_CD3linker |

REFERENCES

Blair G E, Dixon S C, Griffiths S A, Zajdel M E. Restricted replication of human adenovirus type 5 in mouse cell lines. Virus Res. 1989 December; 14(4):339-46.

Ekkens M J, Shedlock D J, Jung E, Troy A, Pearce E L, Shen H, Pearce E J. Th1 and Th2 cells help CD8 T-cell responses. Infect Immun. 2007 May; 75(5):2291-6.

Hemminki, O., S. Parviainen, J. Juhila, R. Turkki, N. Linder, J. Lundin, M. Kankainen, A. Ristimaki, A. Koski, I. Liikanen, M. Oksanen, D. M. Nettelbeck, K. Kairemo, K. Partanen, T. Joensuu, A. Kanerva and A. Hemminki (2015). Immunological data from cancer patients treated with Ad5/3-E2F-Delta24-GMCSF suggests utility for tumor immunotherapy. Oncotarget 6(6): 4467-4481.

Kanerva A et al. 2005, Gene Therapy 12, 87-94.

Kanerva A et al. Clin Cancer Res. 2013 May 15; 19(10): 2734-44.

Koski, A., L. Kangasniemi, S. Escutenaire, S. Pesonen, V. Cerullo, I. Diaconu, P. Nokisalmi, M. Raki, M. Rajecki, K. Guse, T. Ranki, M. Oksanen, S. L. Holm, E. Haavisto, A. Karioja-Kallio, L. Laasonen, K. Partanen, M. Ugolini, A. Helminen, E. Karli, P. Hannuksela, S. Pesonen, T. Joensuu, A. Kanerva and A. Hemminki (2010). Treatment of cancer patients with a serotype 5/3 chimeric oncolytic adenovirus expressing GMCSF. Mol Ther 18(10): 1874-1884.

Kratky W, Reis e Sousa C, Oxenius A, Spörri R. Direct activation of antigen-presenting cells is required for CD8+ T-cell priming and tumor vaccination. Proc Natl Acad Sci USA. 2011 Oct. 18; 108(42):17414-9.

Lugade A A, Sorensen E W, Gerber S A, Moran J P, Frelinger J G, Lord E M. Radiation-induced IFN-gamma production within the tumor microenvironment influences antitumor immunity. J Immunol. 2008 Mar. 1; 180(5):3132-9.

Park, J. G., H. Frucht, R. V. LaRocca, D. P. Bliss, Jr., Y. Kurita, T. R. Chen, J. G. Henslee, J. B. Trepel, R. T. Jensen, B. E. Johnson and et al. (1990). Characteristics of cell lines established from human gastric carcinoma. Cancer Res 50(9): 2773-2780.

Parviainen, S., M. Ahonen, I. Diaconu, M. Hirvinen, A. Karttunen, M. Vaha-Koskela, A. Hemminki and V. Cerullo (2014). CD40 ligand and tdToma-to-armed vaccinia virus for induction of antitumor immune response and tumor imaging. Gene Ther 21(2): 195-204.

Propper D J, Chao D, Braybrooke J P, Bahl P, Thavasu P, Balkwill F, Turley H, Dobbs N, Gatter K, Talbot D C, Harris A L, Ganesan T S. Low-dose IFN-gamma induces tumor MHC expression in metastatic malignant melanoma. Clin Cancer Res. 2003 January; 9(1):84-92.

Schroder K, Hertzog P J, Ravasi T, Hume D A. Interferon-gamma: an overview of signals, mechanisms and functions. J Leukoc Biol. 2004 February; 75(2):163-89.

Street D, Kaufmann A M, Vaughan A, Fisher S G, Hunter M, Schreckenberger C, Potkul R K, Gissmann L, Qiao L. Interferon-gamma enhances susceptibility of cervical cancer cells to lysis by tumor-specific cytotoxic T cells. Gynecol Oncol. 1997 May; 65(2):265-72.

Tahtinen, S., S. Gronberg-Vaha-Koskela, D. Lumen, M. Merisalo-Soikkeli, M. Siurala, A. J. Airaksinen, M. Vaha-Koskela and A. Hemminki (2015). Adenovirus Improves the Efficacy of Adoptive T-cell Therapy by Recruiting Immune Cells to and Promoting Their Activity at the Tumor. Cancer Immunol Res 3(8): 915-925.

Tahtinen, S., S. Kaikkonen, M. Merisalo-Soikkeli, S. Gron-berg-Vaha-Koskela, A. Kanerva, S. Parviainen, M. Vaha-Koskela and A. Hemminki (2015). Favorable alteration of tumor microenvironment by immunomodulatory cytokines for efficient T-cell therapy in solid tumors. PLoS ONE 10(6): e0131242.

Taipale, K., I. Liikanen, J. Juhila, R. Turkki, S. Tahtinen, M. Kankainen, L. Vassilev, A. Ristimaki, A. Koski, A. Kanerva, I. Diaconu, V. Cerullo, M. Vaha-Koskela, M. Oksanen, N. Linder, T. Joensuu, J. Lundin and A. Hemminki (2016). Chronic Activation of Innate Immunity Correlates With Poor Prognosis in Cancer Patients Treated With Oncolytic Adenovirus. Mol Ther 24(1): 175-183.

Webb J. Effect of more than one inhibitor, antagonism, summation, and synergism. In: Webb J, ed. Enzyme and metabolic inhibitors. New York: Academic Press, 1963. 488-512.

Yu et al. 2014, Mol Ther 22(1):102-11.

The invention claimed is:

1. An oncolytic adenoviral vector comprising:
   i) an adenovirus serotype 5 (Ad5) nucleic acid backbone comprising a 5/3 chimeric fiber knob;
   ii) an E2F1 promoter for tumor specific expression of E1A;
   iii) a 24 bp deletion (D24) in the Rb binding constant region 2 of adenoviral E1;
   iv) a nucleic acid sequence deletion of viral gp19k and 6.7k reading frames; and
   v) a nucleic acid sequence encoding a bispecific monoclonal antibody in the place of the deleted gp19k and 6.7k nucleic acid sequence in the E3 region,
   wherein the bispecific monoclonal antibody comprises a single chain variable fragment (scFv) specific for a cell surface molecule on immunological effector cells and a scFv specific for a tumor antigen,
   wherein the tumor antigen is EpCAM1 or MUC 1 and the cell surface molecule is CD3, and
   wherein, in the presence of tumor cells, the bispecific monoclonal antibody is capable of counteracting tumor immunosuppression and promoting the recruitment of T cells to the tumor cells.

2. The oncolytic adenoviral vector according to claim 1, further comprising an IL-2, TNFalpha or CD40L transgene.

3. A pharmaceutical composition comprising an oncolytic adenoviral vector, wherein the oncolytic adenoviral vector comprises:
   i) an adenovirus serotype 5 (Ad5) nucleic acid backbone comprising a 5/3 chimeric fiber knob;
   ii) an E2F1 promoter for tumor specific expression of E1A;
   iii) a 24 bp deletion (D24) in the Rb binding constant region 2 of adenoviral E1;
   iv) a nucleic acid sequence deletion of viral gp19k and 6.7k reading frames; and
   v) a nucleic acid sequence encoding a bispecific monoclonal antibody in the place of the deleted gp19k and 6.7k nucleic acid sequence in the E3 region,
   wherein the bispecific monoclonal antibody comprises a single chain variable fragment (scFv) specific for a cell surface molecule on immunological effector cells and a scFv specific for a tumor antigen,
   wherein the tumor antigen is EpCAM1 or MUC 1 and the cell surface molecule is CD3, and
   wherein, in the presence of tumor cells, the bispecific monoclonal antibody is capable of counteracting tumor immunosuppression and promoting the recruitment of T cells to the tumor cells.

4. The oncolytic adenoviral vector according to claim 1, wherein the tumor antigen is MUC 1.

5. The oncolytic adenoviral vector according to claim 4, wherein the nucleic acid sequence further encodes for IL-2.

6. The oncolytic adenoviral vector according to claim 1, wherein the tumor antigen is EpCAM1.

* * * * *